United States Patent [19]

Bavetsias et al.

[11] Patent Number: 5,747,499
[45] Date of Patent: May 5, 1998

[54] ANTI-CANCER COMPOUNDS

[75] Inventors: Vassilios Bavetsias, Sutton; Francis Thomas Boyle, Cangleton, both of England; Laurent Francois Andre Hennequin, Reims Cedex, France; Jonathan Hugh Marriott, Sutton, England

[73] Assignee: British Technology Group Limited, London, England

[21] Appl. No.: 732,273

[22] PCT Filed: May 4, 1995

[86] PCT No.: PCT/GB95/01016

§ 371 Date: Oct. 29, 1996

§ 102(e) Date: Oct. 29, 1996

[87] PCT Pub. No.: WO95/30673

PCT Pub. Date: Nov. 16, 1995

[30] Foreign Application Priority Data

May 5, 1994 [GB] United Kingdom ............... 9408936

[51] Int. Cl.$^6$ ................. A61K 31/505; C07D 403/04
[52] U.S. Cl. ............................. 514/267; 544/249

[56] References Cited

U.S. PATENT DOCUMENTS

| 4,925,939 | 5/1990 | Watanabe | 544/251 |
|---|---|---|---|
| 5,077,404 | 12/1991 | Piper et al. | 544/250 |

FOREIGN PATENT DOCUMENTS

| 409125 | 1/1991 | European Pat. Off. . |
|---|---|---|
| 438261 | 7/1991 | European Pat. Off. . |
| 0 562 734 A1 | 9/1992 | European Pat. Off. . |
| 509643a | 10/1992 | European Pat. Off. . |
| 562734b | 9/1993 | European Pat. Off. . |
| 2 272 217 A | 5/1994 | United Kingdom . |
| A 272 217 | 5/1994 | United Kingdom . |
| WO 91/13890 | 9/1991 | WIPO . |
| WO 91/19700 | 12/1991 | WIPO . |
| WO 92/05153 | 4/1992 | WIPO . |
| WO 92/05173 | 4/1992 | WIPO . |
| WO 94/03439 | 2/1994 | WIPO . |
| WO 94/07869 | 4/1994 | WIPO . |
| WO 95/09158 | 4/1995 | WIPO . |

OTHER PUBLICATIONS

GB 227217A –see claim 1 and compounds with reg Nos 157701–19–4, 157701–18–3 and 157701–10–5.

W Pendergast et al. "Benzo[1] quinazoline Inhibitors of Thymidylate Synthase: Methyleneamino–linked Aroylglutamate Derivatives", J Med. Chem. 37, 838–844 (1994).

T.C. Stephens et al. "A novel non–polyglutamated thymidylate synthase (TS) inhibitor: in vivo anti–tumour efficacy and toxicity to normal murine tissues", Proceedings of the American Association for Cancer Research, 35, Abstract No. 1816, p. 305 (Mar. 1994).

F.T. Boyle et al."Design of a novel non–polyglutamatable quinazoline–based inhibitor of thymidylate synthase (TS)", Proceedings of the American Association for Cancer Research, 35, Abstract No. 1817, p. 305 (Mar. 1994).

A.L. Jackman et al. "A non–polyglutamatable quinazoline thymidylate synthase (TS)", Proceedings of the American Association for Cancer Research, 35, Abstract No. 1791, p. 301 (Mar. 1994).

L.A. Skelton et al. "Pyridyl quinazolines as inhibitors of thymidylate synthase (TS)", Proceedings of the American Association for Cancer Research, 35, Abstract No. 1792, p. 301 (Mar. 1994).

M.I. Walton et al."Pharmacokinetics of the potent, non–polyglutamatable thymidylate synthase inhibitors CB 30900 and ZD9331 in mice", Proceedings of the American Association for Cancer Research, 35, Abstract No. 1793, p. 301 (Mar. 1994).

W. Gibson et al. "Pharmacology and antitumour activity of sterically hindered dipeptide analogues of the folate–based thymidylate synthase (TS inhibitor, ICI 198583", Brit. J. Cancer, 69, Abstract No. P127, p. 57 (1994).

V. Bavetsias et al. "Synthesis and anti–tumour activity of linked sterically hindered dipeptide analogues of the folate––based thymidylate synthase (TS) inhibitor: ICI 198583", Brit. J. Cancer, 69, Abstract No. P126, p. 56 (1994).

*Primary Examiner*—Matthew V. Grumbling
*Attorney, Agent, or Firm*—Nixon & Vanderhye

[57] ABSTRACT

Cyclopentaquinazoline of the formula (I):

wherein $R^1$ is hydrogen, amino, $C_{1-4}$ alkyl, $C_{1-4}$ alkoxy, $C_{1-4}$ hydroxyalkyl or $C_{1-4}$ fluoroalkyl;

wherein $R^2$ is hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl;

$Ar^1$ is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy; and wherein $R^3$ is a group of the formula:

—$A^1$—$Ar^2$—$A^2$—$Y^1$ in which $A^1$, $A_2$, $Y^1$ and $Ar_2$ are defined in claim 1;

or a pharmaceutically acceptable salt or ester there of are of therapeutic value particularly in the treatment of cancer.

13 Claims, No Drawings

ANTI-CANCER COMPOUNDS

This invention relates to novel anti-cancer agents and more particularly it relates to cyclopentaquinazoline derivatives which possess anti-cancer activity.

One group of anti-cancer agents comprises antimetabolites having anti-folate activity, such as aminopterin and methotrexate. A newer compound of this type which showed considerable promise in clinical trials is known as CB3717 and is described and claimed in United Kingdom Patent No. 2 065 653B. Despite its promising activity against human breast, ovarian and liver cancer, however, CB3717 shows symptoms of toxicity in humans, particularly in relation to the liver and kidneys (Cancer Treatment Reports, 1986, 70, 1335). Such adverse side effects are reduced in compounds in which the 2-amino substituent of CB3717 is either missing or is replaced by one of various alternative substituents as described and claimed respectively in United Kingdom Patents Nos. 2 175 903 and 2 188 319.

Compounds of this type are believed to act as anti-cancer agents by inhibiting the enzyme thymidylate synthase which catalyses the methylation of deoxyuridine monophosphate to produce thymidine monophosphate which is required for DNA synthesis. The anti-cancer activity of CB3717 and like compounds may be assessed in vitro by determining their inhibitory effect on that enzyme, and in cell cultures by their inhibitory effect on cancer cell lines such as the mouse leukaemia cell line L1210, the mouse lymphoma cell line L5178Y TK-/- and the human breast cancer cell line MCF-7.

Antimetabolites such as aminopterin and methotrexate which are inhibitors of enzymes which utilise folic acid derivatives have also shown promise in the treatment of various allergic diseases such as allergic rhinitis, atopic dermatitis and psoriasis.

Antimetabolites such as methotrexate have also shown promise in the treatment of various inflammatory diseases such as inflammation of the joints, especially rheumatoid arthritis, osteoarthritis and gout, and inflammation of the gastrointestinal tract, especially inflammatory bowel disease, ulcerative colitis and gastritis (New England J. Med., 1985, 312, 818).

We have now found that certain cyclopentaquinazoline derivatives show a good level of activity both as regards their ability to inhibit thymidylate synthase and also as regards their anti-cancer activity against various cell lines.

Accordingly the present invention comprises a cyclopentaquinazoline of formula (I):

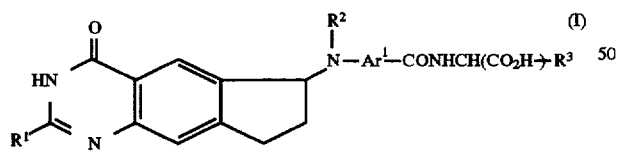

wherein $R^1$ is hydrogen, amino, $C_{1-4}$ alkyl, $C_{1-4}$ alkoxy, $C_{1-4}$ hydroxyalkyl or $C_{1-4}$ fluoroalkyl;

wherein $R^2$ is hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl;

$Ar^1$ is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy; and wherein $R^3$ is a group of the formula:

—$A^1$—$Ar^2$—$A^2$—$Y^1$ in which $A^1$ is a bond between the α-carbon atom of the group —CONHCH(CO$_2$H)— and $Ar^2$ or is a $C_{1-2}$ alkylene group;

$Ar^2$ is phenylene, tetrazoldiyl, thiophenediyl, thiazolediyl, pyridinediyl or pyrimidinediyl which in the case of phenylene may optionally bear one or two substituents on the ring selected from halogeno, nitro, $C_{1-4}$ alkyl and $C_{1-4}$ alkoxy;

$A^2$ is a $C_{1-3}$ alkylene or $C_{2-3}$ alkenylene group; and $Y^1$ is carboxy, tetrazol-5-yl, N—($C_{1-4}$ alkylsulphonyl) carbamoyl, N-(phenylsulphonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulphinyl or tetrazol-5-ylsulphonyl; or $Y^1$ is a group of the formula:

—CON(R)CH(Y$^2$)Y$^3$ in which R is hydrogen, $C_{1-4}$ alkyl, $C_{3-4}$ alkenyl or $C_{3-4}$ alkynyl;

$Y^2$ is carboxy, tetrazol-5-yl, N—($C_{1-4}$ alkylsulphonyl) carbamoyl, N-(phenylsulphonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulphinyl or tetrazol-5-ylsulphonyl; and $Y^3$ is the residue of a naturally occurring amino acid NH$_2$CH(CO$_2$H)Y$^3$; or $Y^3$ is a group of the formula:

—$A^4$—CO$_2$H in which $A^4$ is a $C_{2-6}$ alkylene group other than ethylene; wherein $R^3$ is a group of the formula:

—$A^5$—CON(R)CH(Y$^4$)Y$^5$ in which $A^5$ is a $C_{1-6}$ alkylene group and R is as defined above;

$Y^4$ is carboxy, tetrazol-5-yl, N—($C_{1-4}$ alkylsulphonyl) carbamoyl, N-(phenylsulphonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulphinyl or tetrazol-5-ylsulphonyl; and $Y^5$ is the residue of a naturally occurring amino acid NH$_2$CH(CO$_2$H)Y$^5$ provided that when R is hydrogen and $Y^4$ is carboxy it is not the residue of glutamic acid; or $Y^5$ is a group of the formula:

—$A^4$—CO$_2$H in which $A^4$ is as defined above; or $Y^5$ is a group of the formula:

—$A^6$—$Ar^3$—$A^7$—$Y^6$ in which $A^6$ is a bond between the α-carbon atom of the group —$A^5$—CON(R)CH(Y$^4$)— and $Ar^3$ or is a $C_{1-2}$ alkylene group;

$Ar^3$ is phenylene, tetrazoldiyl, thiophenediyl, thiazolediyl, pyridinediyl or pyrimidinediyl which in the case of phenylene may optionally bear one or two substituents on the ring selected from halogeno, nitro, $C_{1-4}$ alkyl and $C_{1-4}$ alkoxy;

$A^7$ is a $C_{1-3}$ alkylene or $C_{2-3}$ alkenylene group; and $Y^6$ is carboxy, tetrazol-5-yl, N—($C_{1-4}$ alkylsulphonyl)carbamoyl, N-(phenylsulphonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulphinyl or tetrazol-5-ylsulphonyl; or wherein $R^3$ is a group of the formula:

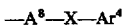

in which $A^8$ is a $C_{1-4}$ alkylene group;

X is sulphinyl, sulphonyl or methylene; and $Ar^4$ is 1,2,3-triazol-4-yl, 1,2,4-triazol-3-yl or, except when X is methylene, tetrazol-5-yl;

the compound (I) optionally being in the form of a pharmaceutically acceptable salt or ester.

In this specification the terms alkyl, alkenyl, alkynyl and alkylene include both straight and branched chain groups but references to individual alkyl or alkylene groups, such as "propyl", are specific for the straight chain group only. An analogous convention applies to other generic terms. Moreover, the numbering system used for the cyclopenta(g)quinazoline nucleus is the conventional one as shown below.

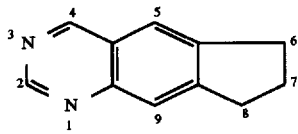

Amino-acid residues are designated herein in the standard manner (Pure and Applied Chemistry, 1974, 40, 317 and European Journal of Biochemistry, 1984, 138, 9). Thus, for example, γ-glutamyl denotes the radical $H_2NCH(CO_2H)CH_2CH_2CO$— or —$NHCH(CO_2H)CH_2CH_2CO$— according to the context, the carbon atoms in these radicals being numbered from the carbon atom of the α-carboxy group as position 1.

It will be observed that a cyclopentaquinazoline of the invention contains at least two asymmetric carbon atoms [present at the point of attachment of the group —$N(R^2)$— to the tricyclic ring system and at the α-carbon atom of the group —$CONHCH(CO_2H)$—] and can therefore exist in racemic and optically active forms. It is to be understood that this invention encompasses both racemic and optically active forms of the physiologically active cyclopentaquinazolines, it being a matter of common general knowledge how such optically active forms may be obtained by stereospecific synthesis or by separation of a mixture of isomeric compounds. It will be appreciated that one isomer may be of more interest than another due to the nature of the activity which it exhibits or due to superior physical properties, for example aqueous solubility.

It is also to be understood that a cyclopentaquinazoline of the formula (I) may exhibit the phenomenon of tautomerism and that the formulae shown in this specification represent only one of the possible tautomeric forms. Moreover, it will be appreciated that when, for example, $Y_1$, $Y^2$, $Y^4$ or $Y^6$ is a tetrazol-5-yl group, that group may be in the form of a 1 H-tetrazol-5-yl group or a 2H-tetrazol-5-yl group. It is to be understood therefore that the invention is not limited merely to any one tautomeric form which is illustrated.

It is also to be understood that certain cyclopentaquinazolines of the formula (I) can exist in solvated as well as unsolvated forms such as, for example, hydrated forms.

A suitable value for $R^1$ or $R^2$ when it is $C_{1-4}$ alkyl, or for a $C_{1-4}$ alkyl substituent which may be present on $Ar^1$, $Ar^2$ or $Ar^3$ or on a phenyl group-containing group $Y^1$, $Y^2$, $Y^4$ or $Y^6$ present in $R^3$, or for a group R present in $R^3$ when it is $C_{1-4}$ alkyl, is, for example, methyl, ethyl, propyl or isopropyl.

A suitable value for $R^1$ when it is $C_{1-4}$ alkoxy or for a $C_{1-4}$ alkoxy substituent which may be present on $Ar^1$, $Ar^2$ or $Ar^3$ or on a phenyl-containing group $Y^1$, $Y^2$, $Y^4$ or $Y^6$ is, for example, methoxy, ethoxy, propoxy, isopropoxy or butoxy.

A suitable value for a halogeno substituent which may be present on $Ar^1$, $Ar^2$ or $Ar^3$ or on a phenyl-containing group $Y^1$, $Y^2$, $Y^4$ or $Y^6$ is, for example, fluoro, chloro or bromo.

A suitable value for $R^1$ when it is $C_{1-4}$ hydroxyalkyl is, for example, hydroxymethyl, 1-hydroxyethyl, 2-hydroxyethyl or 3-hydroxypropyl; and when it is $C_{1-4}$ fluoroalkyl is, for example, fluoromethyl, difluoromethyl, trifluoromethyl or 2-fluoroethyl.

A suitable value for $R^2$ when it is $C_{3-4}$ alkenyl or for a group R present in $R^3$ when it is alkenyl, is, for example, prop-2-enyl, but-2-enyl, but-3-enyl or 2-methylprop-2-enyl; and when $R^2$ or R is $C_{3-4}$ alkynyl is, for example, prop-2-ynyl or but-3-ynyl.

A suitable value for $R^2$ when it is $C_{2-4}$ hydroxyalkyl is, for example, 2-hydroxyethyl or 3-hydroxypropyl; when it is $C_{2-4}$ halogenoalkyl is, for example, 2-fluoroethyl, 2-chloroethyl, 2-bromoethyl, 3-fluoropropyl, 3-chloropropyl or 3-bromopropyl; and when it is $C_{1-4}$ cyanoalkyl is, for example, cyanomethyl, 2-cyanoethyl or 3-cyanopropyl.

A suitable value for $Ar^1$, $Ar^2$ or $Ar^3$ when it is phenylene is, for example, 1,3- or 1,4-phenylene, especially 1,4-phenylene.

A suitable value for $Ar^1$, $Ar^2$ or $Ar^3$ when it is thiophenediyl is, for example, thiophene-2,4-diyl or thiophene-2,5-diyl; when it is thiazolediyl is, for example thiazole-2,4-diyl or thiazole-2,5-diyl; when it is pyridinediyl is, for example, pyridine-2,4-diyl, pyridine-2,5-diyl, pyridine-2,6-diyl or pyridine-3,5-diyl; and when it is pyrimidinediyl is, for example, pyrimidine-2,4-diyl, pyrimidine-2,5-diyl or pyrimidine-4,6-diyl.

As indicated, $Ar^1$ and a phenylene group $Ar^2$ or $Ar^3$ or a phenyl group in $Y^1$ may carry one or two substituents. A preferred level of substitution in $Ar^1$, where substitution is present, is either two substituents or especially one substituent; and the one or two substituents may conveniently be at positions adjacent to the atom bonded to the group —$CONHCH(CO_2H)$—$R^3$, halogeno substituents such as fluoro being preferred. A preferred level of substitution on a phenylene group $Ar^2$ or $Ar^3$ or on a phenyl group in $Y^1$, where substitution is present, is one substituent.

When $R^3$ is a group of the formula

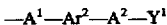

a suitable value for $A^1$ when it is a $C_{1-2}$ alkylene group is, for example methylene or ethylene and for $A^2$ when it is a $C_{1-3}$ alkylene group is, for example, methylene, ethylene or trimethylene. A suitable value for $A^2$ when it is a $C_{2-3}$ alkenylene group is, for example, vinylene or especially propenylene (—$CH_2CH=CH$— or —$CH=CH—CH_2$—). A preferred value for both $A^1$, when it is not a bond, and for $A^2$ is methylene or ethylene. Suitable values for $Ar^2$ include those which have been discussed hereinbefore, such as thiophenediyl or most especially phenylene, or additionally tetrazol-1,5-diyl or tetrazol-2,5-diyl. A suitable value for $Y^1$ or for $Y^2$ in a group $Y^1$ of formula —$CON(R)CH(Y^2)Y^3$ when it is N-($C_{1-4}$ alkylsulphonyl)carbamoyl is, for example, N-methylsulphonylcarbamoyl, N-ethylsulphonylcarbamoyl or N-propylsulphonylcarbamoyl.

In a group $Y^1$ of formula —CON(R)CH($Y^2$)$Y^3$ suitable values for $C_{1-4}$ alkyl, $C_{3-4}$ alkenyl and $C_{3-4}$ alkynyl groups R have been discussed hereinbefore but R is preferably either methyl or especially hydrogen; a suitable value for $Y^3$ when it is the residue of a naturally occurring amino acid is the residue of alanine ($Y^3$=CH$_3$), arginine ($Y^3$=(CH$_2$)$_3$NHC(NH$_2$)=NH), aspartic acid ($Y^3$=CH$_2$CO$_2$H), cysteine ($Y^3$=CH$_2$SH), isoleucine ($Y^3$=CH(CH$_3$)CH$_2$CH$_3$), leucine ($Y^3$=CH$_2$CH(CH$_3$)CH$_3$), ornithine ($Y^3$=(CH$_2$)$_3$NH$_2$), phenylalanine ($Y^3$=CH$_2$C$_6$H$_5$), serine ($Y^3$=CH$_2$OH) and valine ($Y^3$=CH(CH$_3$)$_2$) and especially glutamic acid ($Y^3$=CH$_2$CH$_2$CO$_2$H). A suitable value for $A^4$ when $Y^3$ is a group of the formula —$A^4$—CO$_2$H is trimethylene, pentamethylene or hexamethylene, $A^4$ preferably being a $C_{3-6}$ alkylene group with especially suitable values for $Y^3$ being —(CH$_2$)$_n$CO$_2$H where n is 3, 4 or 5.

A preferred value for $Y^1$ or for $Y^2$, $Y^4$ and $Y^6$, is tetrazol-5-yl or especially carboxy.

When $R^3$ is a group of the formula

—$A^5$—CON(R)CH($Y^4$)$Y^5$ a suitable value for $A^5$ is, for example, methylene, ethylene, trimethylene, tetramethylene, pentamethylene or hexamethylene and a suitable value for R is as described hereinbefore. A suitable value for $Y^4$ when it is N—(C$_{1-4}$ alkylsulphonyl)carbamoyl is, for example, N-methylsulphonylcarbamoyl, N-ethylsulphonylcarbamoyl or N-propylsulphonylcarbamoyl.

A suitable value for $Y^5$ when it is the residue of a naturally occurring amino acid is alanine ($Y^5$=CH$_3$), arginine ($Y^5$=(CH$_2$)$_3$NHC(NH$_2$)=NH), aspartic acid ($Y^5$=CH$_2$CO$_2$H), cysteine ($Y^5$=CH$_2$SH), isoleucine ($Y^5$=CH(CH$_3$)CH$_2$CH$_3$), leucine ($Y^5$=CH$_2$CH(CH$_3$)CH$_3$), ornithine ($Y^5$=(CH$_2$)$_3$NH$_2$), phenylalanine ($Y^5$=CH$_2$C$_6$H$_5$), serine ($Y^5$=CH$_2$OH) and valine ($Y^5$=CH(CH$_3$)$_2$). When $Y^5$ is a group of the formula —$A^4$—CO$_2$H, suitable values for $A^4$ and $Y^5$ are as described hereinbefore in relation to a group $Y^3$ of the formula —$A^4$—CO$_2$H.

A suitable value for $A^6$ in a group $Y^5$ of the formula —$A^6$—Ar$^3$—$A^7$—$Y^6$ is as described hereinbefore for $A^1$ and for $A^7$ is as described for $A^2$. A suitable value for Ar$^3$ is as described hereinbefore for Ar$^2$. A suitable value for $Y^6$ in such a group $Y^5$ when it is N—(C$_{1-4}$ alkylsulphonyl)carbamoyl is, for example, N-methylsulphonyl-carbamoyl, N-ethylsulphonylcarbamoyl or N-propylsulphonylcarbamoyl.

When $R^3$ is a group of the formula

—$A^8$—X—Ar$^4$ a suitable value for $A^8$ is, for example, methylene, ethylene, trimethylene or tetramethylene.

Groups $R^3$ of particular value have the formula —$A^1$—Ar$^2$—$A^2$—$Y^1$, especially when $Y^1$ is a group not of the formula —CON(R)CH($Y^2$)$Y^3$, such as carboxy or tetrazol-5-yl.

Specific examples of such groups $R^3$ are groups —$A^1$—Ar$^2$—$A^2$—$Y^1$ in which $A^1$ is a bond or methylene or ethylene, Ar$^2$ is phenylene, thiophenediyl or tetrazoldiyl, $A^2$ is methylene, ethylene or trimethylene and $Y^1$ is carboxy or tetrazol-5-yl.

Other groups $R^3$ of particular value have the formula —$A^5$—CON(R)CH($Y^4$)$Y^5$, especially when $Y^5$ is a group of the formula —$A^6$—Ar$^3$—$A^7$—$Y^6$ in which Ar$^3$ is phenylene, thiophenediyl or tetrazoldiyl.

Specific examples of such groups $R^3$ are groups —$A^5$—CON(R)CH($Y^4$)—$A^6$—Ar$^3$—$A^7$—$Y^6$ in which $A^5$ is methylene or ethylene, R is hydrogen or methyl, $Y^4$ is carboxy or tetrazol-5-yl, $A^6$ is a bond or is methylene or ethylene, Ar$^3$ is phenylene, thiophenediyl or tetrazoldiyl, $A^7$ is methylene, ethylene or trimethylene and $Y^6$ is carboxy or tetrazol-5-yl.

A suitable pharmaceutically-acceptable salt form of a cyclopentaquinazoline of the invention is, for example, an acid addition salt with an inorganic or organic acid, for example hydrochloric, hydrobromic, trifluoroacetic or maleic acid; or an alkali metal, for example sodium, an alkaline earth metal, for example calcium, or ammonium, for example tetra(2-hydroxyethyl)ammonium, salt.

A suitable pharmaceutically-acceptable ester form of a cyclopentaquinazoline of the invention is, for example, an ester with an aliphatic alcohol of up to 6 carbon atoms, for example a methyl, ethyl or tert-butyl ester.

It is to be understood that $R^3$ may contain several carboxy groups in addition to the carboxy group in the grouping —CONHCH(CO$_2$H)—. When, for example, two carboxy groups are present in the cyclopentaquinazoline, a salt or ester may be mono-acid-mono-salt or -ester, di-salt or di-ester and when, for example, three carboxy groups are present a salt or ester may be mono-acid-di-salt or -ester, di-acid-mono-salt or -ester or even tri-salt or -ester.

Particularly preferred values for the various symbols $R^1$, $R^2$ and Ar$^1$ individually are as expressed for the preferred cyclopentaquinazolines described hereinafter.

A preferred cyclopentaquinazoline of the invention has the formula (I) wherein $R^1$ is hydrogen, amino, hydroxymethyl or especially methyl; wherein $R^2$ is hydrogen, methyl, ethyl, propyl, prop-2-enyl, prop-2-ynyl, 2-hydroxyethyl, 2-fluoroethyl, 2-bromoethyl or 2-cyanoethyl; wherein Ar$^1$ is 1,4-phenylene which may optionally bear one or two substituents selected from the group consisting of chloro and especially fluoro, thiophene-2,5-diyl, thiazole-2,5-diyl or pyridine-2,5-diyl;

wherein $R^3$ is a group of the formula —$A^1$—Ar$^2$—$A^2$—$Y^1$ in which $A^1$ is a bond or is methylene or ethylene, Ar$^2$ is phenylene, thiophenediyl or tetrazoldiyl, $A^2$ is methylene, ethylene or trimethylene and $Y^1$ is carboxy or tetrazol-5-yl;

or $R^3$ is a group of the formula —$A^5$—CON(R)CH($Y^4$)—$A^6$—Ar$^3$—$A^7$—$Y^6$ in which $A^5$ is methylene or ethylene, R is hydrogen or methyl, $Y^4$ is carboxy or tetrazol-5-yl, $A^6$ is a bond or is methylene or ethylene, Ar$^3$ is phenylene, thiophenediyl or tetrazoldiyl, $A^7$ is methylene, ethylene or trimethylene and $Y^6$ is carboxy or tetrazol-5-yl.

A further preferred cyclopentaquinazoline of the invention has the formula (I)

wherein $R^1$ is amino, hydroxymethyl or methyl;

wherein $R^2$ is methyl, ethyl or prop-2-ynyl; and wherein Ar$^1$ is 1,4-phenylene or 1,4-phenylene having a 2-fluoro substituent as in 2,6-difluoro-1,4-phenylene or especially 2-fluoro-1,4-phenylene or is pyridine 2,5-diyl; and $R^3$ is as just described above.

An especially preferred cyclopentaquinazoline of the invention has the formula (I) wherein $R^1$ is methyl;

wherein $R^2$ is ethyl or preferably methyl or prop-2-ynyl;

wherein Ar$^1$ is 1,4-phenylene or 2-fluoro-1,4-phenylene; and wherein $R^3$ is p-carboxymethylphenyl, 2-(1-carboxymethyltetrazol-5-yl)ethyl, 2-(2-carboxymethyltetrazol-5-yl)ethyl or 2-(N-[p-carboxymethyl-α-carboxybenzyl]-carbamoyl)ethyl.

Other quinazolines of the invention of particular interest have the values of $R^1$, $R^2$, and Ar$^1$ and Ar in combination as indicated above but with $R^3$ having any value as indicated hereinbefore. However, specific particularly preferred cyclopentaquinazolines of the invention are:

2-{p-[N-methyl-N-(2-amino-4-oxo-3,4,7,8-tetrahydro-6 H-cyclopenta(g)-quinazolin-6-yl)amino]benzamido}-4-(1- or 2-carboxymethyltetrazol-5-yl)butyric acid, 2-{p-[N-ethyl-N-(2-amino-4-oxo-3,4,7,8-tetrahydro-6 H-cyclopenta(g)-quinazolin-6-yl)amino]benzamido}-4-(1- or 2-carboxymethyltetrazol-5-yl)butyric acid, 2-{p-[N-(prop-2-ynyl)-N-(2-amino-4-oxo-3,4,7,8-tetrahydro-6H-cyclopenta (g)-quinazolin-6-yl amino] benzamido}-4-(1- or 2-carboxymethyltetrazol-5-yl) butyric acid, 2-{p-[N-methyl-(2-hydroxymethyl-4-oxo-3,4,7,8-tetrahydro-6H-cyclopenta (g)-quinazolin-6-yl)amino] benzamido}-4-(1- or 2-carboxymethyltetrazol-5-yl) butyric acid, 2-{p-[N-ethyl-N-(2-hydroxymethyl-4-oxo-3,4,7,8-tetrahydro-6H-cyclopenta (g)-quinazolin-6-yl)amino] benzamido}-4-(1- or 2-carboxymethyltetrazol-5-yl) butyric acid, 2-{p-[N-prop-2-ynyl)-N-(2-hydroxymethyl-4-oxo-3,4,7,8-tetrahydro-6H-cyclopenta (g)-quinazolin-6-yl)amino] benzamido}-4-(1- or 2-carboxymethyltetrazol-5-yl) butyric acid, 2-{p-[N-methyl-N-(2-methyl-4-oxo-3,4,7,8-tetrahydro-6 H-cyclopenta (g)-quinazolin-6-yl)amino]benzamido}-4- (1- or 2-carboxymethyltetrazol-5-yl)butyric acid, 2-{p-[N-ethyl-N-(2-methyl-4-oxo-3,4,7,8-tetrahydro-6 H-cyclopenta (g)-quinazolin-6-yl)amino]benzamido}-4- (1- or 2-carboxymethyltetrazol-5-yl)butyric acid, 2-{p-[N-(prop-2-ynyl)-N-(2-methyl-4-oxo-3,4,7,8-tetrahydro-6H-cyclopenta (g)-quinazolin-6-yl)amino] benzamido}-4-(1- or 2-carboxymethyltetrazol-5-yl) butyric acid, 2-{o-fluoro-p-[N-methyl-N-(2-amino-4-oxo-3,4,7,8-tetrahydro-6H-cyclopenta (g)-quinazolin-6-yl)amino] benzamido}-4-(1- or 2-carboxymethyltetrazol-5-yl) butyric acid, 2-{o-fluoro-p-[N-ethyl-N-(2-amino-4-oxo-3,4,7,8-tetrahydro-6H-cyclopenta (g)-quinazolin-6-yl)amino] benzamido}-4-(1- or 2-carboxymethyltetrazol-5-yl) butyric acid, 2-{o-fluoro-p-[N-(prop-2-ynyl)-N-(2-amino-4-oxo-3,4,7,8-tetrahydro-6H-cyclopenta (g)-quinazolin-6-yl)amino] benzamido}-4-(1- or 2-carboxymethyltetrazol-5-yl) butyric acid, 2-{o-fluoro-p[N-methyl-N-(2-hydroxymethyl-4-oxo-3,4,7, 8-tetrahydro-6H-cyclopenta-(g)-quinazolin-6-yl)amino] benzamido}-4-(1- or 2-carboxymethyltetrazol-5-yl) butyric acid, 2-{o-fluoro-p-[N-ethyl-N-(2-hydroxymethyl-4-oxo-3,4,7,8-tetrahydro-6 H-cyclopenta(g)quinazolin-6-yl)amino]benzamido}-4-(1- or 2-carboxymethyltetrazol-5-yl)butyric acid, 2-{o-fluoro-p-[N-(prop-2-ynyl)-N-(2-hydroxymethyl-4-oxo-3,4,7,8-tetrahydro-6H-cyclopenta(g) quinazolin-6-yl)amino]benzamido }-4-(1- or 2-carboxymethyltetrazol-5-yl)butyric acid, 2-{o-fluoro-p-[N-methyl-N-(2-methyl-4-oxo-3,4,7,8-tetrahydro-6H-cyclopenta (g)-quinazolin-6-yl)amino] benzamido}-4-(1- or 2-carboxymethyltetrazol-5-yl) butyric acid, 2-{o-fluoro-p-[N-ethyl-N-(2-methyl-4-oxo-3,4,7,8-tetrahydro-6H-cyclopenta (g)-quinazolin-6-yl)amino] benzamido}-4-(1- or 2-carboxymethyltetrazol-5-yl) butyric acid, 2-{o-fluoro-p-[N-prop-2-ynyl)-N-(2-methyl-4-oxo-3,4,7,8-tetrahydro-6H-cyclopenta (g)-quinazolin-6-yl)amino] benzamido}-4-(1- or 2-carboxymethyltetrazol-5-yl) butyric acid, or a pharmaceutically acceptable salt or ester thereof.

Further specific particularly preferred cyclopentaquinazolines of the invention correspond firstly to those listed above but with a p-carboxymethylphenyl or 2-(N-[p-carboxymethyl-α-carboxybenzyl]carbamoyl)ethyl group in place of the 2-(1- or 2-carboxymethyltetrazol-5-yl)ethyl group $R^3$ thereof and secondly to those listed above but with a 2-(N-1,3-dicarboxypropyl-N-methylcarbamoyl)ethyl, 2-[1- or 2-(2-carboxyethyl)tetrazol-5-yl]ethyl, 2-{N-[1-carboxy-3-(1- or 2-carboxy-methyltetrazol-5-yl)propyl] carbamoyl}ethyl, 2-{1- or 2-[N-(1-carboxyethyl)-carbamoylmethyl]tetrazol-5-yl}ethyl, 3-(1,2,4-triazol-3-ylsulphonyl)propyl, 2-[N-(3-carboxy-1-tetrazol-5-ylpropyl) carbamoyl]ethyl, 2-[N-(1-carboxyethyl)-carbamoyl]ethyl or 2-[N-(1,4-dicarboxybutyl)carbamoyl]ethyl group in place of the 2-(1- or 2-carboxymethyltetrazol-5-yl)ethyl group $R^3$ thereof.

Although the compounds of the present invention can exist as a mixture of stereoisomers it is preferred that they are resolved into one optically active isomeric form. Such a requirement complicates the synthesis of the compounds and it is preferred therefore that they contain as few asymmetric carbon atoms as possible consistent with achieving the desired activity.

As indicated previously, however, the cyclopentaquinazolines of the present invention contain at least two asymmetric carbon atoms. Of these, that at the 6 position of the ring system preferably has the 6S orientation rather than the 6R orientation, whilst the alpha carbon atom of the group —CONHCH($CO_2$H)— preferably has the L rather than the D configuration. The preferred compounds (I) described hereinbefore thus preferably have such a configuration at these two asymmetric carbon atoms or less preferably are a racemic mixture in which one or both of these asymmetric carbon atoms is unresolved.

The asymmetric carbon atom of a residue $R^3$ of the form —$A^1$—$Ar^2$—$A^2$—CON(R)CH($Y^2$)$Y^3$ or —$A^5$—CON(R)CH($Y^4$)$Y^5$ may be of the L- or D-configuration but the amide bond will be stabilised in vivo when it is of the D-configuration as it will also be when R is other than hydrogen. When $Y^3$ or $Y^5$ is the residue of a naturally occurring amino acid, however, the amino acid intermediate for the synthesis of the cyclopentaquinazoline will of course be more readily available when this asymmetric carbon atom is of the L-configuration.

A cyclopentaquinazoline of the invention may be prepared by any process known to be applicable to the preparation of chemically-related compounds.

The particularly preferred process (a) for the manufacture of a cyclopenta-quinazoline of the invention comprises the reaction of an acid of the formula (II):

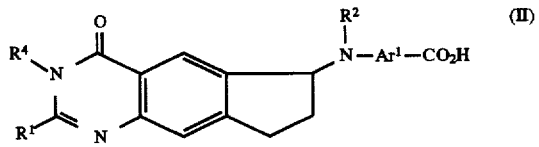

or a reactive derivative thereof, with the terminal amino group of a compound of the formula $NH_2CH(CO_2H)$—$R^3$; wherein $R^1$, $R^2$, $R^3$ and $Ar^1$ have the meanings stated hereinbefore, any amino group in $R^3$ and $Ar^1$ is protected by a conventional protecting group, and any amino group in $R^1$, any hydroxy group in $R^1$, $R^2$, $R^3$ and $Ar^1$ and the carboxy group or groups in $NH_2CH$ $(CO_2H)$—$R^3$ may be protected by a conventional protecting group or alternatively such an amino, hydroxy or carboxy group need not be protected; and wherein $R^4$ is hydrogen or a protecting group which can be removed to replace —$NR^4$— by —NH—; whereafter any undesired protecting group including any protecting group $R^4$ is removed, for example by conventional means.

In this and the other processes described hereinafter the reactants, i.e. the compound $NH_2CH(CO_2H)$—$R^3$ and the cyclopentaquinazoline acid (II) in the case of the first process, conveniently have the stereochemical configuration at the asymmetric carbon atoms therein which is desired in the final cyclopentaquinazolinc of formula (I).

A suitable reactive derivative of an acid of the formula (II) may be, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid (II) and a phenol such as pentafluorophenol or an alcohol such as N-hydroxybenzotriazole; the product of the reaction of the acid and a carbodiimide, for example dicyclohexylcarbodiimide; or particularly an acyl azide, for example an azide formed by the reaction of the acid and an azide such as diphenylphosphoryl azide or an acyl phosphonate, for example an acyl phosphonate formed by the reaction of the acid and a phosphonate such as diethylcyano phosphonate or (1H-1,2,3-benzotriazol-1-yloxy)-tris(pyrrolidino)-phosphonium hexafluorophosphate.

A suitable protecting group for an amino group is, for example, an acyl group, for example an alkanoyl group, especially a ($C_{1-4}$ alkyl)carbonyl group such as acetyl, an alkoxycarbonyl group, especially a ($C_{1-4}$ alkoxy)carbonyl group such as methoxycarbonyl, ethoxycarbonyl or tert-butoxycarbonyl, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed, for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid, for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions will vary with the choice of protecting group. Thus, for example an acyl or aroyl group may be removed, for example, by hydrolysis with a suitable base, such as an alkali metal hydroxide, for example lithium or sodium hydroxide. An arylmethyl group may be removed, for example, by hydrogenation over a catalyst such as palladium-on-charcoal. It will be appreciated therefore that due to the conditions required for deprotection the use of an arylmethyl protecting group will not generally be suitable when $R^2$ contains an alkenyl or alkynyl group.

A suitable protecting group for a carboxy group is, for example, an esterifying group, for example a methyl or ethyl group which may be removed, for example, by hydrolysis with a base such as sodium hydroxide, or for example a tert-butyl group which may be removed, for example, by treatment with an acid, for example an organic acid such as trifluoroacetic acid, thereby avoiding the possibility of racemization which can arise with groups removable by base. An alternative esterifying group is, for example, a benzyl group which can be removed, for example, by hydrogenation over a catalyst such as palladium-on-carbon.

A further alternative protecting group for a carboxy group is, for example, an allyl group which may be removed, for example, using catalytic amounts of tetrakis triphenylphosphine palladium(O) in the presence of an excess of pyrrolidine.

Where the group $R^4$ is a protecting group rather than hydrogen this may for example be one of the various forms of conventional protecting group such as are described hereinbefore as being generally suitable as a protecting group for an amino group, for example an alkoxycarbonyl group such as tert-butoxycarbonyl. However, other types of group may also be used and may be more suited to this particular situation, particularly (a) an alkyloxymethyl group such as methyloxymethyl removable, for example, with a suitable acid such as the Lewis acid boron tribormide, (b) an aralkyloxymethyl group such as benzyloxymethyl removable, for example, by palladium-catalysed hydrogenolysis, (c) an arylmethyl group such as a 4-methoxy-or 3,4- or 2,4-dimethoxy-benzyl removable, for example, with a suitable acid such as trifluoracetic acid, (d) a trialkylsilyl group such as tri-isopropyl- or tert-butyldimethyl-silyl removable, for example, with a suitable acid such as hydrochloric acid or with a fluoride salt such as tetra-n-butylammonium fluoride, and especially (e) an alkanoyloxymethyl group such as pivaloyloxymethyl removable, for example, with a suitable base such as sodium hydroxide or ammonia. The removal of the group $R^4$ may involve the use of a suitable inert solvent or diluent, for example methanol or ethanol in case (e). In general care should be taken to avoid racemization when an optically active product is involved.

It will be appreciated that the protecting groups for the various carboxy groups in $R^3$ may be esterifying groups such as permit the product after removal of any undesired protecting group in $R^1$, $R^2$, $R^3$ and $Ar^1$ and of any protecting group $R^4$ to fall within the definition of a cyclopentaquinazoline of the invention. In such instance the esterified carboxy groups in $R^3$ may if desired be retained in the final product. Alternatively either such a protecting group or a different protecting group used in $R^3$ will be removed.

The reaction of the acid (II) and the compound $NH_2CH$ $(CO_2H)$—$R^3$ is preferably carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, N-methylmorpholine or diazabicyclo[5.4.0]undec-7-ene. The reaction is also preferably carried out in a suitable inert solvent or diluent, for example tetrahydrofuran, 1,2-dimethoxyethane, N,N-dimethylformamide, N,N-dimethylacetamide, N-methylpyrrolidin-2-one, dimethylsulphoxide or acetone, and at a temperature in the range, for example, of −78° to 150° C., conveniently at or near ambient temperature.

The starting materials consisting of the acid (II) and the compound $NH_2CH(CO_2H)R^3$, and also those used for the other processes described hereinafter, may be obtained by any of the various standard procedures of organic chemistry which are described in the literature, as illustrated by the specific Examples. Thus, for example, where peptides are being formed standard methods involving reaction in solution or solid phase methods may both be used. Preferably, however, the amide bond is produced by reaction of the appropriate two amino acids in solution, the amino group of one acid and the carboxy group of the other acid being protected, for example by protecting groups as described hereinbefore, particularly suitable groups being a benzyloxycarbonyl or trityl group and a tert-butyl or methyl esterifying group, respectively.

The cyclopentaquinazoline acid (II) used as starting material may, for example, be obtained by the reaction of a compound of the formula (III):

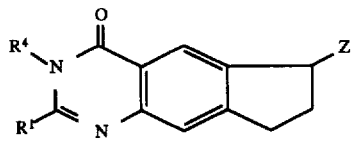

(III)

wherein $R^1$ and $R^4$ have the meanings stated hereinbefore and Z is a displaceable group, with a compound of the formula:

$HNR^2$—$Ar^1$—W wherein $R^2$ and $Ar^1$ have the meanings stated hereinbefore and W is a carboxy group or a group convertible to a carboxy group.

A suitable value for the displaceable group Z is, for example, a halogeno or sulphonyloxy group, particularly a chloro, bromo, methanesulphonyloxy (mesyloxy) or 4-toluenesulphonyloxy group.

One particular example of a group W is the group —$CO_2R^5$ wherein $R^5$ is a protecting group which can be removed from —$CO_2R^5$ to provide a carboxy group, the reactant then having the formula $HNR^2$—$Ar^1$—$CO_2R^5$ A suitable value for $R^5$ is, for example, an alkyl group such as a methyl or an ethyl group which may be removed by hydrolysis with a base, for example sodium hydroxide, or alternatively a tert-butyl group which may be removed by cleavage with an acid, for example an organic acid such as trifluoroacetic acid. The protecting group for the carboxy group provided by $R^5$ is preferably an esterifying group which can be removed while the protecting group for any amino, hydroxy and carboxy group in $R^1$, $R^2$ and $Ar^1$ is retained.

A second particular example of a group W is the group —$CONR^6R^7$ wherein $R^6$ and $R^7$ are each separately hydrogen or a group such that —$CONR^6R^7$ is convertible to a carboxy group, preferably while the protecting group for any amino, hydroxy and carboxy group in $R^1$, $R^2$ and $Ar^1$ is retained, the reactant then having the formula

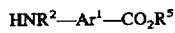

$HNR^2$—$Ar^1$—$CONR^6R^7$

A suitable value for $R^6$ is, for example, hydrogen or an alkyl group such as methyl, ethyl, propyl or butyl and for $R^7$ is, for example, hydrogen, a group —$CH(CO_2H)(CH_2)_2CO_2H$ or an alkyl group such as methyl, ethyl, propyl or butyl.

In the specific case where $R^6$ is hydrogen and $R^7$ is a group —$CH(CO_2H)(CH_2)_2CO_2H$, carboxypeptidase G2 enzyme may conveniently be used to remove the L-glutamic acid residue from a compound of formula (I) but in which $R^3$ is instead —$(CH_2)_2CO_2H$ thereby generating a carboxy group. Such an L-glutamic acid compound may itself be prepared from a compound of formula (III) by reaction with a compound of the formula $NH(R^2)$—$Ar^1$—$CONHCH(CO_2H)$—$R^3$ in which $R^3$ is instead a group —$(CH_2)_2CO_2H$ using the process (b), including the protection procedures, described hereinafter. In the case where $R^6$ and $R^7$ are each separately hydrogen or alkyl, conversion of the group —$CONR^6R^7$ to a carboxy group may be effected by any suitable procedure for hydrolysing amides. Although an alkali metal hydroxide such as potassium hydroxide or an alkali metal peroxide such as sodium peroxide may be used to effect direct conversion of the group to a carboxy group, the use of milder conditions is preferred to minimise unwanted reactions elsewhere in the molecule, for example a two stage procedure may be used involving N-acylation with a reagent such as β-acetoxypivaloyl chloride or di-tert-butyl dicarbonate followed by hydrolysis of the acylated product with a reagent such as lithium hydroxide.

As an alternative starting material to a compound (III) for the preparation of the cyclopentaquinazoline acid (II) it is possible to use a compound of the formula (IIIA):

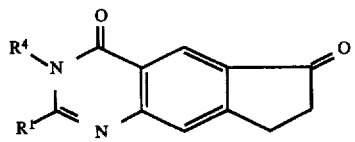

(IIIA)

wherein $R^1$ and $R^4$ have the meanings stated hereinbefore.

To produce the cyclopentaquinazoline acid (II) the compound (IIIA) is also reacted with a compound of the formula $HNR^2$—$Ar^1$—W which may particularly be of the formula $HNR^2$—$Ar^1$—$CO_2R^5$ or of the formula $HN(R^2)$—$Ar^1$—$CONR^6R^7$ as described hereinbefore, but in this case the reaction is carried out in two stages. In the first stage the compound (IIIA) and the compound $HNR^2$—$Ar^1$—W are reacted in the presence of a suitable acid, for example a sulphonic acid such as p-toluene sulphonic acid, a Lewis acid such as titanium (IV) chloride or titanium (IV) isopropoxide, a mineral acid such as hydrobromic acid or a carboxylic acid such as acetic acid, in a suitable inert solvent or diluent, for example 1,2-dimethoxyethane. The reaction is conveniently effected at a temperature in the range of, for example 60°–100° C., and preferably at or near 80° C., preferably at the reflux temperature of the inert solvent or diluent and in the presence of molecular sieve beads to aid the removal of the water formed during the condensation of the compound (IIIA) and the amino compound. In the second stage a suitable reducing agent is used to reduce the product of the condensation in a suitable inert solvent or diluent and at a suitable temperature depending upon the reducing agent used. Reducing agents include, by way of example, an alkali metal borohydride such as sodium cyanoborohydride, hydrogen in the presence of a catalyst such as platinum or tris (triphenylphosphine) rhodium (I) chloride and formic acid and the complex of borane with a suitable amine such as pyridine. The reduction is conveniently effected with sodium cyanoborohydride or other alkali metal borohydride in an inert solvent such as 1,2-dimethoxyethane and at a temperature in the range of, for example 10° to 30° C., preferably at or near ambient temperature.

It will be appreciated that the compounds of formula (IIIA) are useful intermediates for the preparation of the compounds (I) and as novel compounds are included within the scope of the present invention. Such compounds may, for example, be obtained by the oxidation with a suitable oxidising agent of the corresponding cyclopentaquinazoline lacking any substituent at the 6 position in a suitable inert solvent or diluent and at a suitable temperature depending upon the oxidising agent used. Oxidising agent systems may comprise, by way of example, various compounds containing chromium in oxidation state (VI) such as (a) chromium (VI) oxide in acetic acid, (b) pyridinium chlorochromate in benzene, (c) chromium (VI) oxide-70%-tert-butyl hydroperoxide in dichloromethane, (d) pyridinium dichromate -70% tert-butyl hydroperoxide in benzene and (e) bistriphenylsilyl chromate -70% tert-butyl hydroperoxide in dichloromethane, as well as compounds of a different type such as (f) 2,3-dichloro-5,6-dicyano-1,4-benzoquinone (DDQ) in aqueous acetic acid. The systems (a), (c), (d), (e) may conveniently be used at a temperature in the range of 10° to 30° C. and preferably at or near ambient temperature whilst the systems (b) and (f) may conveniently be used at or about the reflux temperature of the solvent.

An alternative process (b) for the manufacture of a cyclopentaquinazoline of the invention comprises the reaction of a compound of the formula (III) or the reductive amination of a compound of the formula (IIIA) with a compound of the formula:

NH(R²)—Ar¹—CONHCH(CO₂H)—R³ wherein in these compounds $R^1$, $R^2$, $R^3$, $R^4$, $Ar^1$ and Z have the meanings stated hereinbefore, any amino group in $R^3$ and $Ar^1$ is protected by a conventional protecting group, for example as described hereinbefore, the carboxy group or groups in NH(R²)—Ar¹—CONHCH(CO₂H)—R³ are protected by a conventional protecting group, for example as described hereinbefore, and any amino group in $R^1$ and any hydroxy group in $R^1$, $R^2$, $R^3$ and $Ar^1$ may be protected by a conventional protecting group, for example as described hereinbefore, or alternatively such an amino or hydroxy group need not be protected; whereafter any undesired protecting group including any protecting group $R^4$ is removed, for example by conventional means as described above In the case of a compound (III), the reaction is preferably carried out in the presence of a suitable base, for example as described hereinbefore in relation to the process (a), in a suitable inert solvent or diluent, for example as described hereinbefore in relation to the process (a), and at a temperature in the range of, for example, 25° to 150° C., conveniently at or near 90° C.

In the case of a compound (IIIA), the reductive amination is preferably carried out as described previously for the reaction of a compound (IIIA) with a compound of the formula HNR²—Ar¹—W.

A further alternative process (c) for the manufacture of a cyclopentaquinazoline of the invention in which $R^2$ is not hydrogen comprises the alkylation of an amine of the formula (IV):

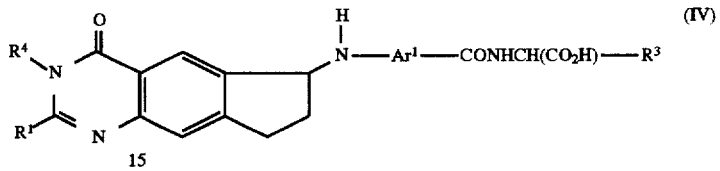

with an alkylating agent of the formula:

R²—Z wherein $R^1$, $R^2$, $R^3$, $R^4$, $Ar^1$ and Z have the meanings stated hereinbefore and any amino group in $R^1$, $R^3$ and $Ar^1$ is protected by a conventional protecting group, for example as described hereinbefore.

The reaction is conveniently carried out in the presence of a suitable base, for example as described hereinbefore in relation to process (a), in a suitable inert solvent or diluent, for example as described hereinbefore in relation to process (a), and at a temperature in the range of, for example 25° to 150° C., preferably at or near 100° C.

The compounds of formula (IV) do of course correspond to compounds of formula (I) in which $R^2$ is hydrogen with optional protection at the 3-position and may be obtained by the use of a process (a) or particularly a process (b) as described hereinbefore to provide such a compound of formula (I).

A further alternative process (d) for the manufacture of a cyclopentaquinazoline of the invention in which $R^2$ is a group whose attachment to the nitrogen atom to which it is bonded is through a methylene group comprises the reductive amination with an amine of the formula (IV) as described hereinbefore of a compound of the formula:

R⁸—CHO wherein $R^8$ is a group which corresponds to the group $R^2$ lacking that methylene group, i.e. $R^8$—$CH_2$ corresponds to $R^2$.

The reaction is conveniently performed in the presence of a suitable reducing agent, for example an alkali metal borohydride or cyanoborohydride such as sodium cyanoborohydride, in the presence of a suitable inert solvent or diluent, for example methanol, ethanol or acetic acid, and at a temperature in the range, for example, 10° to 60° C., preferably at or near ambient temperature.

When a pharmaceutically acceptable salt of a novel compound of the formula (I) is required, it may be obtained, for example, by reaction of said compound with a suitable acid or base using a conventional procedure. When a pharmaceutically acceptable ester of a novel compound of the formula (I) is required, it may be obtained, for example, by reaction of said compound with a suitable acid or alcohol using a conventional procedure. When an optically active form of a compound of the formula (I) is required, it may preferably be obtained by carrying out one of the aforesaid processes using an optically active starting material, or alternatively by resolution of a racemic form of said compound using a conventional procedure.

One example of a procedure for obtaining an optically active starting material is the controlled use of carboxypeptidase G2 enzyme on a compound of formula (I) having the 6RS configuration but in which $R^3$ is instead —(CH$_2$)$_2$CO$_2$H, as described hereinbefore to produce a separable mixture of the same compound of the 6S configuration and of the corresponding compound of formula (II) having the 6R configuration in which the L-glutamic acid residue has been removed. A second example is the use of a reducing agent such as the complex of borane with an optically active amino alcohol, for example (R)-(+)-2-amino-3-methyl-1,1-diphenylbutan-1-ol, in the second stage of the reaction of a compound (IIIA) with an amino compound HNR$^2$—Ar$^1$—W, for example HNR$^2$—Ar$^1$—CO$_2$R$^5$ or HN(R$^2$)—Ar$^1$—CONHCH(CO$_2$H)—R$^3$, as described hereinbefore, to effect reduction of the intermediate to produce a product enriched in the 6S isomer.

As stated above, cyclopentaquinazolines of the present invention are believed to function as anti-cancer agents at least in part due to their ability to inhibit the enzyme thymidylate synthase. This anti-cancer activity may be assessed, for example, using one or more of the procedures set out below:

(a) An in vitro assay which determines the ability of a test compound to inhibit the enzyme thymidylate synthase. Thymidylate synthase may be obtained in partially purified form from L1210 mouse leukaemia cells and utilised in the assay using the procedures described by Jackman et al (Cancer Res., 1986, 46, 2810) and Sikora et al. (Biochem. Pharmacol., 1988, 37, 4047);

(b) An assay which determines the ability of a test compound to inhibit the growth of the leukaemia cell line L1210 in cell culture. The test may be similar to that described in UK Patent Specification No. 2065653B and has been described by Jones et al. (J. Med. Chem., 1985, 28, 1468);

(c) An assay which determines the ability of a test compound to inhibit the growth of the human breast cancer cell line MCF-7 in cell culture. The test is similar to that described by Lippman et al (Cancer Res., 1976, 36, 4595); and (d) An assay which determines the ability of a test compound to be cytotoxic to the lymphoma cell line L5178Y TK-/- in vitro. The lymphoma cell line L5178Y TK-/- is deficient in the enzyme thymidine kinase which phosphorylates thymidine and thus operates to generate a pool of thymidylate when de novo synthesis of thymidylate is prevented by the presence of an effective amount of an inhibitor of thymidylate synthase. The L5178Y TK-/- cell line is thereby more sensitive to the presence of an inhibitor of thymidylate synthase. [L5178Y TK-/- was obtained by mutation of the parent L5178Y cell line which is described by, for example, Fischer et al. (Methods in Medical Research, 1964, 10, 247).]

Although the pharmacological properties of the cyclopentaquinazolines of the invention depend on their detailed structure, in general the cyclopentaquinazolines of the invention possess activity in one or more of the above tests (a) to (d) as indicated below:

Test (a) IC$_{50}$ in the range, for example, 0.0001–1 µM;

Test (b) IC$_{50}$ in the range, for example, 0.01–50 µM;

Test (c) IC$_{50}$ in the range, for example, 0.01–50 µM;

Test (d) IC$_{50}$ in the range, for example, 0.01–50 µM;

Thus, by way of example, the title cyclopentaquinazolines of Examples 8 and 10 to 19 hereinafter have IC$_{50}$ values in test (a) of 0.0076, 0.0088, 0.0148, 0.0040, 0.00142, 0.00184, 0.00108, 0.0034, 0.00158, 0.00108 and 0.00184 µM, respectively, and the title cyclopentaquinazolines of Examples 10 to 19 hereinafter have IC$_{50}$ values in test (b) of 1.2, 23, 3.9, 2.3, 0.63, 7.2, 10, 0.25, 0.86 and 0.52 µM, respectively.

A cyclopentaquinazoline of the present invention may itself be active or it may be a pro-drug which is converted in vivo to an active compound. A cyclopentaquinazoline of the invention may be administered to a warm-blooded animal, including a human, in the form of a pharmaceutical composition which comprises the cyclopentaquinazoline in association with a pharmaceutically-acceptable diluent or carrier.

The composition may be in a form suitable for oral use, for example a tablet, capsule, aqueous or oily solution, suspension or emulsion; a form suitable for topical use, for example a cream, ointment, gel or aqueous or oily solution or suspension; a form suitable for nasal use, for example a snuff, nasal spray or nasal drops; a form suitable for vaginal or rectal use, for example a suppository; a form suitable for administration by inhalation, for example as a finely divided powder such as a dry powder, a microcrystalline form or a liquid aerosol; a form suitable for sub-lingual or buccal use, for example a tablet or capsule; or a form suitable for parenteral use (including intravenous, subcutaneous, intramuscular, intravascular or infusion use), for example a sterile aqueous or oily solution, emulsion or suspension. In general the above compositions may be prepared in a conventional manner using conventional excipients.

The composition may contain, in addition to the cyclopentaquinazoline of the invention, one or more other anti-cancer substances selected from, for example, mitotic inhibitors, for example vinblastine; alkylating agents, for example cis-platin, carboplatin and cyclophosphamide; other antimetabolites, for example 5-fluorouracil, cytosine arabinoside and hydroxyurea; intercalating antibiotics, for example adriamycin and bleomycin; enzymes, for example asparaginase; topoisomerase inhibitors, for example etoposide and biological response modifiers, for example interferon.

The cyclopentaquinazoline will normally be administered to a warm-blooded animal at a dose within a range of 50–25000, particularly 50–5000, mg per square meter body area of the animal, i.e. approximately 1–500, particularly 1–100, mg/kg. Where desired, however, dosages outside this range may be employed and, in particular, where the preferred mode of administration involving subcutaneous infusion is used then the does range may be increased to 1–1000 mg/kg. Preferably a daily dose in the range 10–250 mg/kg is employed, particularly 30–150 mg/kg. However, the daily dose will necessarily be varied depending upon the host treated, the particular route of administration and the severity of the illness being treated. Accordingly, the optimum dosage may be determined by the practitioner who is treating any particular patient.

Accordingly the present invention also includes a method for aiding regression and palliation of cancer in a patient, particularly a warm-blooded animal such as a human, in need of such treatment, which comprises administering to said patient an effective amount of a cyclopentaquinazoline as defined hereinbefore. The invention also provides the use of such a cyclopentaquinazoline in the manufacture of a novel medicament for use in the treatment of cancer.

Cyclopentaquinazolines of the present invention are of interest for a wide range of anti-tumour activities, particularly in the human, including the treatment of breast, ovarian and liver cancer. In addition they are of interest in the context of the treatment of a range of leukaemias, lymphoid malignancies and solid tumours such as carcinomas and sarcomas.

In view of the activity shown by antimetabolites such as aminopterin and methotrexate, which is discussed hereinbefore, the cyclopentaquinazolines of the present invention are also of interest for use in the treament of other conditions, for example allergic conditions such as psoriasis and inflammatory diseases such as rheumatoid arthritis. In using a cyclopentaquinazoline of the invention for such a purpose the compound will normally be administered at a dose within the range 5–25000, particularly 5–500, mg per square meter body area of the animal, i.e. approximately 0.1–500, particularly 0.1–10, mg/kg. Where desired, however, dosages outside this range may be employed. In general, for the treatment of an allergic condition such as psoriasis, topical administration of a cyclopentaquinazoline of the invention is preferred. Thus, for example, for topical administration a daily dose in the range, for example, of 0.1 to 10 mg/kg may be used.

Compositions containing the quinazolines may be formulated in unit dosage form, i.e. in the form of discrete portions each comprising a unit dose, or a multiple or sub-multiple of a unit dose, for example as a tablet or capsule. Such a unit dosage form may, for example, contain an amount of the cyclopentaquinazoline in the range of 1–250 or 1–500 mg.

The invention is illustrated by the following Examples.

Examples 1 to 7 describe the preparation of cyclopentaquinazoline intermediates of formula (II) in reactive derivative form. The compound of Example 2 is used in the preparation of the cyclopentaquinazolines of formula (I) as described in Examples 8 to 12 and that compound may be substituted in the procedures described in those examples by any of the other intermediates of Examples 1 and 3 to 7 to provide the alternative cyclopentaquinazoline of formula (I). The compound of Example 4(4), prepared by a variation of the procedure described in Example 4 which is described in Example 13, is used in the preparation of the cyclopentaquinazolines of formula (I) as described in Examples 13 to 17 and 19 and corresponding compounds to that of Example 4(4) described in Examples 1, 3 and 5 to 7 can also be used to provide alternative cyclopentaquinazolines (I).

Procedures suitable for use in the preparation of alternative intermediates for reaction with the cyclopentaquinazoline intermediates of Examples 1 to 7 to provide further cyclopentaquinazolines of the invention are illustrated by the specific examples of UK patent applications 2 253 849 and 2 265 148, and in the equivalents thereof filed in other countries.

In Examples 1 to 7 and in Examples 8 and 9 and sections (1) and (2) of Examples 10 and 12 the following apply unless otherwise stated:

(i) Evaporations were carried out by rotary evaporation in vacuo and work-up procedures were carried out after removal of residual solids by filtration.

(ii) Operations were carried out at ambient temperature and under an atmosphere of an inert gas such as argon.

(iii) Column chromatography (by the flash procedure) and medium pressure liquid chromatography (MPLC) were performed on Merck Kieselgel silica (Art. 9385) or Merck Lichroprep RP-18 reversed-phase silica (Art. 9303).

(iv) The structures of the title compounds of the Examples were generally confirmed by NMR spectra. Proton magnetic resonance spectra were determined using a Jeol FX 90Q or a Bruker AM200 spectrometer operating at a field strength of 200 MHz. Chemical shifts are reported in parts per million downfield from tetramethylsilane as an internal standard (δscale) and peak multiplicities are shown thus: s, singlet; d, doublet; d of d's, doublet of doublet's; t, triplet, m, multiplet.

(v) Intermediates were not generally fully characterised and purity was assessed by thin layer chromatographic, infrared (IR) or NMR analysis.

(vi) Melting points are uncorrected and were determined using a Mettler SP62 automatic melting point apparatus, a Koffler block or an oil-bath apparatus.

In Examples 10 to 19 [apart from sections (1) and (2) of Examples 10 and 12], the following variations apply:

(ii) The use of an atmosphere of an inert gas is specifically indicated.

(iii) Column chromatography was performed using Merck Art 15111 or Merck Art 7729 silica gel. Petroleum ether refers to the fraction of boiling point 60°–80° C.

(iv) and (v) The techniques used to confirm structures are indicated, being one or more of NMR and mass spectra, and elemental analysis for the title compounds.

Proton magnetic resonance spectra were determined using a Bruker WM250 spectrometer operating at a field strength of 250 MHz. Chemical shifts and peak multiplicities are reported as before and the attribution believed to be appropriate for each signal is also indicated. Mass spectra were obtained using a VG 7070H spectrometer and VG 2235 data system with fast-atom bombardment ionization (FAB), chemical ionization (CI) or electron impact ionization (EI), a VG ZAB-SE spectrometer with fast-atom bombardment ionization (FAB) or a Finnigan TSQ 700 spectrometer with electrospray ionization (ESI). Where appropriate, either positive ion data or negative ion data were again collected.

(vi) Melting points are again uncorrected and were determined on a Koffler block.

The following abbreviations have been used throughout Examples 1 to 11:

| THF | tetrahydrofuran |
| --- | --- |
| DMF | N,N-dimethylformamide |
| DMA | N,N-dimethylacetamide |
| DMSO | dimethylsulphoxide |
| NMP | N-methylpyrrolidin-2-one |

EXAMPLES

Example 1

Pentafluorophenyl o-fluoro-p-[N-((6RS)-2-methyl-4-oxo-3-pivaloyloxy-methyl-3,4,7,8-tetrahydro-6H-cyclopenta[g]-quinazolin-6-yl)amino]benzoate (1) 5-Acetamidoindan A mixture of 5-aminoindan (100 g), acetic anhydride (84 g), pyridine (65 g) and ethyl acetate (500 ml) was stirred at ambient temperature for 16 hours. The mixture was evaporated and the residue was triturated under diethyl ether (800 ml). The solid was filtered off, washed with diethyl ether (500 ml) and with hexane (500 ml) and dried. There was thus obtained 5-acetamidoindan (104.5 g), m.p. 107° C.

(2) 5-Acetamido-6-bromoindan

Bromine (105 g) was added dropwise to a stirred mixture of 5-acetamidoindan (104.5 g) and acetic acid (400 ml), the rate of addition being such that the temperature of the reaction mixture was maintained in the range 20° to 25° C. The mixture was poured into a mixture (2 L) of ice and water. The precipitate was isolated, washed with water and dried. There was thus obtained 5-acetamido-6-bromoindan (143 g), m.p. 138° C.

(3) 5-Acetamido-6-cyanoindan

A mixture of 5-acetamido-6-bromoindan (143 g), cuprous cyanide (65.5 g) and NMP (600 ml) was stirred and heated to 125° C. for 30 minutes. The mixture was cooled to ambient temperature and poured into a mixture of concentrated aqueous ammonia solution (specific gravity 0.88, 1 L) and ice (3 L). The mixture was stirred for 15 minutes. The precipitate was isolated and washed with water (3 L). A mixture of the solid so obtained and methylene chloride (2 L) was stirred at ambient temperature for 30 minutes. The mixture was filtered and the filtrate was dried (MgSO$_4$) and evaporated. The residue was triturated under diethyl ether (1.5 L). There was thus obtained 5-acetamido-6-cyanoindan (104 g), m.p. 172° C.

(4) 2-Methyl-3,4,7,8-tetrahydro-6H-cyclopenta[g]quinazolin-4-one

A mixture of 5-acetamido-6-cyanoindan (104 g), hydrogen peroxide (30% solution in water, 400 ml), sodium hydroxide (35 g), water (200 ml) and ethanol (1 L) was stirred and heated to 50° C. for 1 hour. The mixture was cooled to ambient temperature and evaporated. The residue was dissolved in water (2 L) and the solution was acidified to pH 5 by the addition of 2N aqueous hydrochloric acid. The precipitate was isolated, washed with water and dried under vacuum. There was thus obtained 2-methyl-3,4,7,8-tetrahydro-6H-cyclopenta[g]quinazolin-4-one (100 g), m.p. 284° C.

(5) 2-Methyl-3-pivaloyloxymethyl-3,4,7,8-tetrahydro-6H-cyclopenta[g]-quinazolin-4-one Potassium tert-butoxide (64 g) was added portionwise during 15 minutes to a stirred solution of 2-methyl-3,4,7,8-tetrahydro-6H-cyclopenta[g]quinazolin-4-one (89 g) in DMSO (700 ml). The mixture was stirred at ambient temperature for 30 minutes. Chloromethyl pivaloate (131 g) was added dropwise during 30 minutes. The mixture was stirred at ambient temperature for 24 hours. The mixture was poured into a mixture of ammonium chloride (500 g) and a mixture (3 L) of ice and water. Ethyl acetate (2 L) was added and the mixture was filtered. The organic layer was dried (MgSO$_4$) and evaporated. The residue was triturated under diethyl ether (500 ml). The mixture was cooled to 0° C. for 2 hours. The solid was isolated, washed with diethyl ether and dried. There was thus obtained 2-methyl-3-pivaloyloxymethyl-3,4,7,8-tetrahydro-6H-cyclopenta[g]quinazolin-4-one (72.4 g), m.p. 128° C.

(6) 6-Bromo-2-methyl-3-pivaloyloxymethyl-3,4,7,8-tetrahydro-6H-cyclopenta[g]-quinazolin-4-one A mixture of 2-methyl-3-pivaloyloxymethyl-3,4,7,8-tetrahydro-6H-cyclopenta[g]-quinazolin-4-one (50 g), N-bromosuccinimide (31.2 g), benzoyl peroxide (0.1 g) and carbon tetrachloride (500 ml) was stirred and heated to reflux for 90 minutes. The mixture was cooled to 0° C. The mixture was filtered and the filtrate was evaporated. The residue was triturated under diethyl ether (400 ml). The mixture was cooled to 0° C. The precipitate was isolated, washed with diethyl ether and dried. The solid so obtained was purified by column chromatography using a 1:1 mixture of hexane and ethyl acetate as eluant. There was thus obtained 6-bromo-2-methyl-3-pivaloyloxy-methyl-3,4,7,8-tetrahydro-6H-cyclopenta[g]quinazolin-4-one (21 g), m.p. 98° C. (decomposes);

NMR Spectrum: (CDCl$_3$) 1.2 (s, 9H), 2.55 (m, 2H), 2.65 (s, 3H), 3.0 (m, 1H), 3.3 (m, 1H), 5.65 (d of d's, 1H), 6.1 (q, 2H), 7.5 (s, 1H), 8.3 (s, 1H).

(7) o-Fluoro-p-[N-((6RS)-2-methyl-4-oxo-3-pivaloyloxymethyl-3,4,7,8-tetrahydro-6H-cyclopenta[g]quinazolin-6-yl)amino]benzoic acid A mixture of 6-bromo-2-methyl-3-pivaloyloxymethyl-3,4,7,8-tetrahydro-6H-cyclopenta[g]quinazolin-4-one (26 g), p-amino-o-fluorobenzoic acid 1,1-dimethyl-2-hydroxyethylammonium salt (42 g), calcium carbonate (21.4 g) and DMSO (200 ml) was stirred at ambient temperature for 72 hours. The mixture was poured onto a mixture of ice and water (1 liter). The precipitate was isolated, washed with water and dried under vacuum. The product was purified by column chromatography using initially a 9:1 mixture of methylene chloride and methanol and then a 9:1:0.1 mixture of methylene chloride, methanol and acetic acid as eluant. There was thus obtained o-fluoro-p-[N-((6RS)-2-methyl-4-oxo-3-pivaloyloxymethyl-3,4,7,8-tetrahydro-6H-cyclopenta[g]quinazolin-6-yl)amino]benzoic acid as a gum (20 g).

(8) Pentafluorophenyl o-fluoro-p-[N-((6RS)-2-methyl-4-oxo-3-pivaloyloxymethyl-3,4,7,8-tetrahydro-6H-cyclopenta[g]quinazolin-6-yl)amino]benzoate A mixture of o-fluoro-p-[N-((6RS)-2-methyl-4-oxo-3-pivaloyloxymethyl-3,4,7,8-tetrahydro-6H-cyclopenta[g]quinazolin-6-yl)amino]-benzoic acid (0.75 g), pentafluorophenol (1.77 g), N,N-dicyclohexylcarbodiimide (0.66 g), N-hydroxybenzotriazole (0.01 g) and methylene chloride (100 ml) was stirred at ambient temperature for 18 hours. The mixture was filtered and the filtrate was evaporated. The residue was purified by column chromatography using increasingly polar mixtures of hexane and ethyl acetate as eluant. There was thus obtained pentafluorophenyl o-fluoro-p-[N-((6RS)-2-methyl-4-oxo-3-pivaloyloxymethyl-3,4,7,8-tetrahydro-6H-cyclopenta[g]quinazolin-6-yl)amino]benzoate as a gum (0.72 g);

NMR Spectrum: (CDCl$_3$) 1.23 (s, 9H), 2.05 (m, 1H), 2.65 (s, 3H), 2.75 (m, 1H), 3.13 (m, 2H), 4.8 (d, 1H), 5.15 (s d's, 1H), 6.1 (2 d's, 2H), 6.3 (m, 2H), 7.5 (s, 1H), 7.95 (t, 1H), 8.2 (s, 1H).

Example 2

Pentafluorophenyl o-fluoro-p-[N-methyl-N-((6RS)-2-methyl-4-oxo-3-pivaloyloxymethyl-3,4,7,8-tetrahydro-6H-cyclopenta[g]quinazolin-6-yl)amino]benzoate An aqueous solution of formaldehyde (37% weight/volume, 17.55 ml) was added dropwise during 15 minutes to a stirred solution of pentafluorophenyl o-fluoro-p-[N-((6RS)-2-methyl-4-oxo-3-pivaloyloxymethyl-3,4,7,8-tetrahydro-6H-cyclopenta[g]quinazolin-6-yl)amino]benzoate (13 g), prepared as described in Example 1, in glacial acetic acid (100 ml). The mixture was stirred at ambient temperature for 1 hour. Sodium cyanoborohydride (1.36 g) was added portionwise during 30 minutes and the resultant mixture was stirred at ambient temperature for 2 hours. The mixture was poured onto a mixture of ice and water (500 ml) and extracted with ethyl acetate. The organic phase was dried (MgSO$_4$) and evaporated. The product was purified by column chromatography using increasingly polar mixtures of hexane and ethyl acetate as eluant. There was thus obtained pentafluorophenyl o-fluoro-p-[N-methyl-N-((6RS)-2-methyl-4-oxo-3-pivaloyloxymethyl-3,4,7,8-tetrahydro-6H-cyclopenta[g]quinazolin-6-yl)amino]benzoate (11 g);

NMR Spectrum: (CDCl$_3$) 1.23 (s, 9H), 2.15 (m, 1H), 2.55 (m, 1H), 2.65 (s, 3H), 2.8 (s, 3H), 3.15 (m, 2H), 5.65 (t, 1H), 6.1 (2 d's, 2H), 6.6 (2 d's, 1) 6.72 (2 s's, 1H), 7.53 (s, 1H), 7.97 (d, 1H), 8.03 (s, 1H).

Example 3

Pentafluorophenyl o-fluoro-p-[N-((6RS)-2-methyl-4-oxo-3-pivaloyloxy-methyl-3,4,7,8-tetrahydro-6H-cyclopenta[g]-quinazolin-6-yl)-N-(prop-2-ynyl)amino]-benzoate (1) a-Fluoro-p-[N-((6RS)-2-methyl-4-oxo-3-pivaloyloxymethyl-3,4,7,8-tetrahydro-6H-cyclopenta[g]quinazolin-6-yl)amino]-β,β-dimethylstyrene A solution of 6-bromo-2-methyl-3-pivaloyloxymethyl-3,4,7,8-tetrahydro-6H-cyclopenta[g]quinazolin-4-one (2.4 g), prepared as described in section (6) of Example 1, in DMA (15 ml) was added to a stirred mixture of p-amino-o-fluoro-β,β-dimethylstyrene (2.03 g), calcium carbonate (2.7 g) and DMA (25 ml) which had been heated to 70° C. The mixture was stirred at 70° C. for 1 hour. The mixture was cooled to ambient temperature and partitioned between ethyl acetate and water. The organic phase was washed with water, dried (MgSO₄) and evaporated. The residue was purified by column chromatography using increasingly polar mixtures of hexane and ethyl acetate as eluant. There was thus obtained o-fluoro-p-[N-((6RS)-2-methyl-4-oxo-3-pivaloyloxymethyl-3,4,7,8-tetrahydro-6H-cyclopenta[g]quinazolin-6-yl)amino]-β,β-dimethylstyrene (1.4 g);

NMR Spectrum: (CDCl₃) 1.23 (s, 9H), 1.81 (s, 3H), 1.91 (s, 3H), 1.95 (m, 1H), 2.64 (s, 3H), 2.70 (m, 1H), 3.06 (m, 2H), 4.05 (broad s, 1H), 5.03 (s, 1H), 6.1 (m, 3H), 6.42 (m, 2H), 7.06 (m, 1H), 7.48 (s, 1H), 8.24 (s 1H).

(2) o-Fluoro-p-[N-((6RS)-2-methyl-4-oxo-3-pivaloyloxymethyl-3,4,7,8-tetrahydro-6H-cyclopenta[g]quinazolin-6-yl)-N-(prop-2-ynyl)amino]-β,β-dimethylstyrene A mixture of o-fluoro-p-[N-((6RS)-2-methyl-4-oxo-3-pivaloyloxymethyl-3,4,7,8-tetrahydro-6H-cyclopenta[g]quinazolin-6-yl)amino]-β,β-dimethylstyrene (1.4 g), propargyl bromide (6.1 g), calcium carbonate (0.88 g) and DMA (20 ml) was stirred and heated to 80° C. for 6 hours. The mixture was evaporated and the residue was partitioned between ethyl acetate and water. The organic phase was washed with water and with brine, dried (MgSO₄) and evaporated. The residue was purified by column chromatography using initially increasingly polar mixtures of hexane and ethyl acetate and then increasingly polar mixtures of methylene chloride and ethyl acetate as eluant. There was thus obtained o-fluoro-p-[N-((6RS)-2-methyl-4-oxo-3-pivaloyloxymethyl-3,4,7,8-tetrahydro-6H-cyclopenta[g]quinazolin-6-yl)-N-(prop-2-ynyl)amino]-β,β-dimethylstyrene (1.04 g);

NMR Spectrum: (CDCl₃) 1.23 (s, 9H), 1.81 (s, 3H), 1.91 (s, 3H), 2.2 (t, 1H), 2.28–2.6 (m, 2H), 2.65 (s, 3H), 2.9–3.3 (m, 2H), 4.35 (2 d's, 2H), 5.5 (t, 1), 6.1 (s, 2H), 6.16 (s, 1H), 6.66 (m, 2H), 7.13 (t, 1H), 7.5 (s 1H), 8.13 (s, 1H).

(3) o-Fluoro-p-[N-((6RS)—2-methyl-4-oxo-3-pivaloyloxymethyl-3,4,7,8-tetrahydro-6H-cyclopenta[g]quinazolin-6-yl)-N-(prop-2-ynyl)amino]benzaldehyde o-Fluoro-p-[N-((6RS)-2-methyl-4-oxo-3-pivaloyloxymethyl-3,4,7,8-tetrahydro-6H-cyclopenta[g]quinazolin-6-yl)-N-(prop-2-ynyl)amino]-β,β-dimethylstyrene (0.626 g) was dissolved in a mixture of methylene chloride (2 ml) and ethanol (250 ml). The mixture was cooled to −70° C. and ozone gas was passed into the solution for 7.5 minutes. Argon gas was bubbled into the solution for 5 minutes. Dimethyl sulphide (4 ml) was added and the mixture was allowed to warm to ambient temperature. The mixture was evaporated and the residue was purified by column chromatography using a 1:1 mixture of hexane and ethyl acetate as eluant. There was thus obtained o-fluoro-p-[N-((6RS)-2-methyl-4-oxo-3-pivaloyloxymethyl-3,4,7,8-tetrahydro-6H-cyclopenta[g]quinazolin-6-yl)-N-(prop-2-ynyl)amino]benzaldehyde (0.47 g);

NMR Spectrum: (CDCl₃) 1.2 (s, 9H), 2.25 (m, 2H), 2.64 (m, 4H), 2.95–3.35 (m, 2H) 3.9 (m, 2H), 5.6 (t, 1H), 6.1 (s, 2H), 6.65 (m, 1H), 6.8 (m, 1H), 7.53 (s, 1H), 7.8 (t, 1H), 8.1 (s, 1H), 10.15 (s, 1H).

(4) o-Fluoro-p-[N-((6RS)-2-methyl-4-oxo-3-pivaloyloxymethyl-3,4,7,8-tetrahydro-6H-cyclopenta[g]quinazolin-6-yl)-N-(prop-2-ynyl)amino]benzoic acid Sodium chlorite (0.28 g) and sulphamic acid (0.24 g) were added portionwise to a stirred mixture of o-fluoro-p-[N-((6RS)-2-methyl-4-oxo-3-pivaloyloxymethyl-3,4,7,8-tetrahydro-6H-cyclopenta[g]quinazolin-6-yl)-N-(prop-2-ynyl)amino]benzaldehyde (0.47 g), 0.2M sodium acetate in acetic acid buffer (pH 4, 70 ml) and tert-butanol (70 ml). The mixture was stirred at ambient temperature for 24 hours. The mixture was partitioned between methylene chloride and a saturated aqueous sodium dihydrogen phosphate solution. The organic phase was washed with brine, dried (MgSO₄) and evaporated. The residue was purified by column chromatography to give o-fluoro-p-[N-((6RS)-2-methyl-4-oxo-3-pivaloyloxymethyl-3,4,7,8-tetrahydro-6H-cyclopenta[g]quinazolin-6-yl)-N-(prop-2-ynyl)amino]benzoic acid (0.41 g);

NMR Spectrum: (CDCl₃+CD₃SOCD₃) 1.2 (s, 9H), 2.33 (m, 2H), 2.63 (m, 4H), 2.97–3.3 (m, 2H), 4.3 (m, 2H), 5.6 (t, 1H), 6.1 (s, 2H), 6.72 (m, 2H), 7.52 (s, 1H), 7.86 (t, 1H), 8.05 (s, 1H).

(5) Pentafluorophenyl o-fluoro-p-[N-((6RS)-2-methyl-4-oxo-3-pivaloyloxymethyl-3,4,7,8-tetrahydro-6H-cyclopenta[g]quinazolin-6-yl)-N-(prop-2-ynyl)amino]benzoate Using an analogous procedure to that described in section (5) of Example 6 o-fluoro-p-[N-((6RS)-2-methyl-4-oxo-3-pivaloyloxy-methyl-3,4,7,8-tetrahydro-6H-cyclopenta[g]quinazolin-6-yl)-N-(prop-2-ynyl)amino]benzoic acid was reacted with pentafluorophenyl trifluoroacetate to give pentafluorophenyl o-fluoro-p-[N-((6RS)-2-methyl-4-oxo-3-pivaloyloxymethyl-3,4,7,8-tetrahydro-6H-cyclopenta[g]quinazolin-6-yl)-N-(prop-2-ynyl)arnino]benzoate in 75% yield.

FOOTNOTE

The p-amino-o-fluoro-β,β-dimethylstyrene used in (1) was obtained as follows:

A mixture of o-fluoro-p-nitrobenzaldehyde (3.35 g) and (2-methoxycarbonyl-prop-2-yl) triphenylphosphonium iodide (Synth. Comm., 1982, 469; 11 g) was stirred and heated to 130° C. for 20 minutes. The mixture was cooled to ambient temperature and purified by column chromatography using a 100:1 mixture of hexane and diethyl ether as eluant. There was thus obtained o-fluoro-p-nitro-β,β-dimethylstyrene as an oil (3.05 g);

NMR Spectrum: (CDCl₃) 1.84 (s, 3H), 1.78 (s, 3H), 6.25 (s, 1H), 7.4 (t, 1H), 7.96 (m, 2H).

A portion (2.2 g) of the material so obtained was added to a stirred mixture of stannous chloride dihydrate (12.8 g) and ethyl acetate (200 ml) which had been heated to 50° C. The resultant mixture was stirred and heated to 70° C. for 1.5 hours. The mixture was cooled to ambient temperature and poured into a dilute aqueous ammonium hydroxide solution. The mixture was extracted with ethyl acetate. The organic phase was washed with water and with brine, dried (MgSO₄) and evaporated. There was thus obtained p-amino-o-fluoro-β,β-dimethylstyrene as an oil (1.85 g);

NMR Spectrum: (CDCl₃) 1.76 (s, 3H), 1.85 (s, 3H), 3.7 (broad s, 2H), 6.13 (s, 1H), 6.38 (m, 2H), 7.0 (t, 1H).

Example 4

Pentafluorophenyl p-[N-((6RS)-2-methyl-4-oxo-3,4,7,8-tetrahydro-6H-cyclopenta[g]quinazolin-6-yl)-N-(prop-2-ynyl)-amino]benzoate (1) Diethyl N-{p-[N-((6RS)-2-methyl-4-oxo-3-pivaloyloxymethyl-3,4,7,8-tetrahydro-6H-cyclopenta[g]quinazolin-6-yl)amino]benzoyl}-L-glutamate A mixture of 6-bromo-2-methyl-3-pivaloyloxymethyl-3,4,7,8-tetrahydro-6H-cyclopenta[g]quinazolin-4-one (21 g), prepared as described in section (6) of Example 1, diethyl p-aminobenzoyl-L-glutamate (52.5 g), prepared as described in the Journal of Medicinal Chemistry, 1985, 28, 1428, calcium carbonate (27.5 g) and DMA (200 ml) was stirred and heated to 110° C. for 30 minutes. The mixture was cooled to ambient temperature. The mixture was evaporated and the residue was partitioned between ethyl acetate and water. The organic phase was dried (MgSO$_4$) and evaporated. The residue was purified by column chromatography using initially a 1:1 mixture of hexane and ethyl acetate as eluant and then a 1:3 mixture of hexane and ethyl acetate as eluant. There was thus obtained a gum which on trituration under diethyl ether gave diethyl N-{(p-[N-((6RS)-2-methyl-4-oxo-3-pivaloyloxymethyl-3,4,7,8-tetrahydro-6H-cyclopenta[g]quinazolin-6-yl)amino]-benzoyl}-L-glutamate (13.5 g), m.p. 156° C.;

NMR Spectrum: (CD$_3$SOCD$_3$) 1.13 (s, 9H), 1.2 (2 t's, 6H), 2.0 (m, 3H), 2.45 (t, 2H), 2.6 (s, 3H), 3.05 (m, 2H), 4.05 (2 q's, 4H), 4.4 (m, 1H), 5.2 (broad t, 1H), 6.05 (q, 2H), 6.65 (broad s, 1H), 6.8 (d, 2H), 7.5 (s, 1H), 7.7 (d, 2H), 7.95 (s, 1H), 8.25 (d, 1H).

(2) Diethyl N-{p-[N-((6RS)-2-methyl-4-oxo-3-pivaloyloxymethyl-3,4,7,8-tetrahydro-6H-cyclopenta[g]quinazolin-6-yl)-N-(prop-2-ynyl)-amino]benzoyl}-L-glutamate A mixture of diethyl N-{p-[N-((6RS)-2-methyl-4-oxo-3-pivaloyloxymethyl-3,4,7,8-tetrahydro-6H-cyclopenta[g]quinazolin-6-yl)amino]benzoyl}-L-glutamate (13.5 g), propargyl bromide (32 g), calcium carbonate (10.7 g) and DMA (250 ml) was stirred and heated to 110° C. for 5 hours. The mixture was evaporated and the residue was partitioned between ethyl acetate and water. The organic phase was washed with water, dried (MgSO$_4$) and evaporated. The residue was purified by column chromatography using increasingly polar mixtures of hexane and ethyl acetate as eluant. There was thus obtained diethyl -{p-[N-((6RS)-2-methyl-4-oxo-3-pivaloyloxymethyl-3,4,7,8-tetrahydro-6H-cyclopenta[g]quinazolin-6-yl)-N-(prop-2-ynyl)—amino]benzoyl }-L-glutamate as a foam (9 g).

(3) N-{p-[N-((6RS)-2-Methyl-4-oxo-3,4,7,8-tetrahydro-6H-cyclopenta-[g]quinazolin-6-yl)-N-(prop-2-ynyl)amino]benzoyl}-L-glutamic acid A mixture of diethyl N-{p-[N-((6RS)-2-methyl-4-oxo-3-pivaloyloxymethyl-3,4,7,8-tetrahydro-6H-cyclopenta[g]quinazolin-6-yl)-N-(prop-2-ynyl)amino]benzoyl }-L-glutamate (9 g), in aqueous sodium hydroxide (60 ml) and methanol (300 ml) was stirred at ambient temperature for 24 hours. The mixture was concentrated by evaporation to a volume of approximately 20 ml. Water (200 ml) was added and the mixture was acidified to pH 4 by the addition of 2N aqueous hydrochloric acid. The precipitate was isolated, washed with water and dried under vacuum. There was thus obtained N-{p-[N-((6RS)-2-methyl-4-oxo-3,4,7,8-tetrahydro-6H-cyclopenta-[g]quinazolin-6-yl)-N-(prop-2-ynyl)amino]benzoyl}-L-glutamic acid (7 g), m.p. 188° C.;

NMR Spectrum: (CD$_3$SOCD$_3$) 2.0 (m, 2H), 2.2 (m, 2H), 2.35 (m, 5H), 3.05 (s, 1H), 3.1 (m, 2H), 3.35 (m, 1H), 4.05 (m, 1H), 4.35 (q, 1H), 5.75 (t, 3H), 7.0 (d, 2H), 7.5 (s, 1H), 7.75 (d, 2H), 7.8 (s, 1H), 8.1 (d, 1H), 12.0 (s, 1H).

Elemental Analysis: Found C, 60.5; H, 5.2; N, 10.5; C$_{27}$H$_{26}$N$_4$O$_6$1H$_2$O 0.25 NaCl requires C, 60.6; H, 5.2; N, 10.5%.

(4) p-[N-((6RS)-2-Methyl-4-oxo-3,4,7,8-tetrahydro-6H-cyclopenta[g]quinazolin-6-yl)-N-(prop-2-ynyl)amino]benzoic acid A mixture of N-{p-[N-((6RS)-2-methyl-4-oxo-3,4,7,8-tetrahydro-6H-cyclopenta[g]quinazolin-6-yl)-N-(prop-2-ynyl)amino]benzoyl}-L-glutamic acid (6 g), carboxypeptidase G$_2$ (2000 units) and tris buffer [prepared by mixing 2-amino-2-hydroxymethyl-1,3-propanediol (12.11 g), zinc chloride (0.035 g) and distilled water (950 ml), by adjusting the basicity of the mixture to pH 7.3 by the addition of 2N aqueous hydrochloric acid and by adding sufficient distilled water to give a final volume of 1 L; 750 ml] was stirred and heated to 37° C. for 30 hours. A second portion of carboxypeptidase G$_2$ (2000 units) was added and the mixture was heated to 37° C. for a further 24 hours. The mixture was cooled to 0° C. and acidified to pH 4 by the addition of glacial acetic acid. The precipitate was isolated, washed with water and dried under vacuum. There was thus obtained p-[N-((6RS)-2-methyl-4-oxo-3,4,7,8-tetrahydro-6H-cyclopenta[a]quinazolin-6-yl)-N-(prop-2-ynyl)amino]benzoic acid as a solid (4 g), m.p. 264° C.;

NMR Spectrum: (CD$_3$SOCD$_3$) 2.2 (m, 2H), 2.35 (s, 3H), 3.0 (m, 2H), 3.1 (s, 1H), 3.85 (m, 1H), 4.1 (m, 1H), 5.75 (t, 1H), 7.05 (d, 2H), 7.5 (s, 1H), 7.8 (s, 1H), 7.85 (d, 2H), 12.1 (broad s, 2H).

(5) Pentafluorophenyl p-[N-((6RS)-2-methyl-4-oxo-3,4,7,8-tetrahydro-6H-cyclopenta[g]quinazolin-6-yl)-N-(prop-2-ynyl)amino]benzoate Using an analogous procedure to that described in section (3) of Example 5 p-[N-((6RS)-2-methyl-4-oxo-3,4,7,8-tetrahydro-6H-cyclopenta[g]quinazolin-6-yl)-N-(prop-2-ynyl)amino]benzoic acid was reacted with pentafluorophenol to give pentafluorophenyl p-[N-((6RS)-2-methyl-4-oxo-3,4,7,8-tetrahydro-6H-cyclopenta-[g]quinazolin-6-yl)-N-(prop-2-ynyl)amino]benzoate.

Example 5

Pentafluorophenyl p-[N-((6S)-2-methyl-4-oxo-3,4,7,8-tetrahydro-6H-cyclopenta[g]quinazolin-6-yl)-N-(prop-2-ynyl)amino]benzoate (1) N-{p-[N-((6S)-2-Methyl-4-oxo-3,4,7,8-tetrahydro-6H-cyclopenta-[g]quinazolin-6-yl)-N-(prop-2-ynyl)amino] benzoyl}-L-glutamic acid A mixture of N-{p-[N-((6RS)-2-methyl-4-oxo-3,4,7,8-tetrahydro-6H-cyclopenta[g]quinazolin-6-yl)-N-(prop-2-ynyl)amino]benzoyl}-L- glutamic acid (5.5 g), prepared as described in section 3 of Example 4, carboxypeptidase G$_2$ (J. Med. Chem., 1992, 35, 859, Eur. J. Biochem., 1985, 148, 447; 2000 units) and tris buffer (700 ml) was stirred and heated to 37° C. for 2.75 hours. The mixture was cooled to 0° C. and acidified to pH 4 by the addition of glacial acetic acid. The precipitate was isolated and dried. The precipitate was purified by column chromatography using initially a 9:1 mixture of methylene chloride and methanol and then a 9:1:0.1 mixture of methylene chloride, methanol and acetic acid as eluant. There were thus obtained:

N-{p-[N-((6S)-2-methyl-4-oxo-3,4,7,8-tetrahydro-6H-cyclopenta[g]quinazolin-6-yl)-N-(prop-2-ynyl)amino] benzoyl}-L-glutamic acid (2.7 g), m.p. 218° C.;

NMR Spectrum: (CD$_3$SOCD$_3$) 2.0 (m, 2H), 2.2 (m, 2H), 2.35 (m, 5H), 3.05 (s, 1H), 3.1 (m, 2H), 3.35 (m, 1H), 4.05 (m, 1H), 4.35 (q, 1H), 5.75 (t, 3H), 7.0 (d, 2H), 7.5 (s, 1H), 7.75 (d, 2H), 7.8 (s, 1H), 8.1 (d, 1H), 12.0 (s, 1H);

and p-[N-((6R)-2-methyl-4-oxo-3,4,7,8-tetrahydro-6H-cyclopenta[g]quinazolin-6-yl)-N-(prop-2-ynyl)amino] benzoic acid (2.0 g);

NMR Spectrum: (CD$_3$SOCD$_3$) 2.2 (m, 2H), 2.35 (s, 3H), 3.0 (m, 2H), 3.1 (s, 1H), 3.85 (m, 1H), 4.1 (m, 1H), 5.75 (t, 1H), 7.05 (d, 2H), 7.5 (s, 1H), 7.8 (S, 1H), 7.85 (d, 2H), 12.1 (broad s, 2H).

(2) p-[N-((6S)-2-Methyl-4-oxo-3,4,7,8-tetrahydro-6H-cyclopenta[g]quinazolin-6-yl)-N-(prop-2-ynyl)amino] benzoic acid A mixture of N-{p-[N-((6S)-2-methyl-4-oxo-3,4,7,8-tetrahydro-6H-cyclopenta[g]quinazolin-6-yl)-N-(prop-2-ynyl)amino]-L-glutamic acid (1 g), carboxypeptidase $G_2$ (1000 units) and tris buffer (200 ml) was stirred and heated to 37° C. for 24 hours. A second portion of carboxypeptidase $G_2$ (1000 units) was added and the mixture was stirred at 37° C. for a further 24 hours. The mixture was cooled to 0° C. and acidified to pH 4 by the addition of glacial acetic acid. The precipitate was isolated and dried under vacuum. The precipitate was purified by column chromatography using a 9:1 mixture of methylene chloride and methanol as eluant. There was thus obtained p-[N-((6S)-2-methyl-4-oxo-3,4,7,8-tetrahydro-6H-cyclopenta[g]quinazolin-6-yl)-N-(prop-2-ynyl)amino]benzoic acid (0.7 g);

NMR Spectrum: ($CD_3SOCD_3$) 2.2 (m, 2H), 2.35 (s, 3H), 3.0 (m, 2H), 3.1 (s, 1H), 3.85 (m, 1H), 4.1 (m, 1H), 5.75 (t, 1H), 7.05 (d, 2H), 7.5 (s, 1H), 7.8 (s, 1H), 7.85 (d, 2H), 12.1 (broad s, 2H).

(3) Pentafluorophenyl p-[N-((6S)-2-methyl-4-oxo-3,4,7,8-tetrahydro-6H-cyclopenta[g]quinazolin-6-yl)-N-(prop-2-ynyl)amino]benzoate A solution of p-[N-((6S)-2-methyl-4-oxo-3,4,7,8-tetrahydro-6H-cyclopenta-[g]quinazolin-6-yl)-N-(prop-2-ynyl)amino]benzoic acid (0.7 g) in DMA (25 ml) was added to a stirred mixture of pentafluorophenol (1.2 g), N,N-dicyclohexylcarbodiimide (0.45 g) and DMA (50 ml). The resultant mixture was stirred at 50° C. for 18 hours. The mixture was evaporated and the residue was purified by column chromatography using initially a 40:1 and then a 20:1 mixture of methylene chloride and methanol as eluant. There was thus obtained pentafluorophenyl p-[N-((6S)-2-methyl-4-oxo-3,4,7,8-tetrahydro-6H-cyclopenta[g] quinazolin-6-yl)-N-(prop-2-ynyl)-amino]benzoate as a solid (0.57 g);

NMR Spectrum: ($CD_3SOCD_3$) 2.2 (m, 2H), 2.35 (s, 3H), 3.05 (m, 2H), 3.2 (s, 1H), 3.95 (m, 1H), 4.2 (m, 1H), 5.9 (t, 1H), 7.05 (d, 2H), 7.5 (s, 1H), 7.8 (s, 1H), 8.05 (d, 2H).

Example 6

Pentafluorophenyl 5-[N-methyl-N-((6RS)-2-methyl-4-oxo-3,4,7,8-tetrahydro-6H-cyclopenta[g]quinazolin-6-yl)amino[pyridine-2-carboxylate (1) Methyl 5-[N-(tert-butoxycarbonyl)-N-((6RS)-2-methyl-4-oxo-3-pivaloyloxy-methyl-3,4,7,8-tetrahydro-6H-cyclopenta[g]quinazolin-6-yl)amino]pyridine-2-carboxylate A solution of methyl 5-[N-(tert-butoxycarbonyl)amino] pyridine-2-carboxylate (J. Med. Chem., 1991, 1594; 0.32 g) in DMA (10 ml) was added dropwise to a stirred suspension of sodium hydride [60% dispersion in mineral oil, 0.051 g, from which the oil was removed using hexane] in DMA (5 ml). The mixture was stirred at ambient temperature for 30 minutes. This mixture was added dropwise to a stirred solution of 6-bromo-2-methyl-3-pivaloyloxymethyl-3,4,7,8-tetrahydro-6H-cyclopenta-[g]quinazolin-4-one (0.5 g), prepared as described in section 6 of Example 1, in DMA (10 ml) which had been cooled to −10° C. The resultant mixture was stirred at ambient temperature for 18 hours. The mixture was evaporated and the residue was partitioned betwen ethyl acetate and water. The organic phase was dried (MgSO$_4$) and evaporated. The residue was purified by column chromatography using increasingly polar mixtures of hexane and ethyl acetate to give methyl 5-[N-(tert-butoxycarbonyl)-N-((6RS)-2-methyl-4-oxo-3-pivaloyloxymethyl-3,4,7,8-tetrahydro-6H-cyclopenta-[g]quinazolin-6-yl)amino] pyridine-2-carboxylate as a gum (0.3 g).

(2) Methyl 5-[N-((6RS)-2-methyl-4-oxo-3-pivaloyloxymethyl-3,4,7,8-tetrahydro-6H-cyclopenta[g] quinazolin-6-yl)amino]pyridine-2-carboxylate A mixture of methyl 5-[N-(tert-butoxycarbonyl)-N-( (6RS)-2-methyl-4-oxo-3-pivaloyloxymethyl-3,4,7,8-tetrahydro-6H-cyclopenta[g]quinazolin-6-yl)amino] pyridine-2-carboxylate (0.3 g) and trifluoroacetic acid (10 ml) was stirred at ambient temperature for 1 hour. The mixture was evaporated and the residue was partitioned between ethyl acetate and a saturated aqueous sodium bicarbonate solution. The organic phase was dried (MgSO$_4$) and evaporated. The residue was purified by column chromatography using increasingly polar mixtures of hexane and ethyl acetate as eluant. There was thus obtained methyl 5-[N-((6RS)-2-methyl-4-oxo-3-pivaloyloxymethyl-3,4,7,8-tetrahydro-6H-cyclopenta[g]quinazolin-6-yl)amino] pyridine-2-carboxylate (0.24 g);

NMR Spectrum: (CDCl$_3$) 1.2 (s, 9H), 2.02 (m, 1H), 2.52 (m, 1H), 2.64 (s, 3H), 3.12 (m, 2H), 3.98 (s, 3H), 4.56 (d, 1H), 5.15 (2 d's, 1H), 6.1 (2 d's, 2H), 7.02 (2 d's, 1H), 7.5 (s, 1H), 8.0 (d, 1H), 8.18 (d, 1H), 8.22 (s, 1H).

(3) Methyl 5-[N-methyl-N-((6RS)-2-methyl-4-oxo-3-pivaloyloxy-methyl-3,4,7,8-tetrahydro-6H-cyclopenta[g] quinazolin-6-yl)-amino]pyridine-2-carboxylate A mixture of methyl 5-[-((6RS)-2-methyl-4-oxo-3-pivaloyloxy-methyl-3,4,7,8-tetrahydro-6H-cyclopenta[g] quinazolin-6-yl)amino]-pyridine-2-carboxylate (0.24 g), an aqueous solution of formaldehyde (37% weight/volume, 0.52 ml) and glacial acetic acid (5 ml) was stirred at ambient temperature for 30 minutes. Sodium cyanoborohydride (0.05 g) was added portionwise during 5 minutes and the mixture was stirred at ambient temperature for 30 minutes. The mixture was poured onto a mixture of ice and water (20 ml) and extracted with ethyl acetate. The organic phase was dried (MgSO$_4$) and evaporated. The residue was purified by column chromatography using ethyl acetate as eluant. There was thus obtained methyl 5-[N-methyl-N-((6RS)-2-methyl-4-oxo-3-pivaloyloxymethyl-3,4,7,8-tetrahydro-6H-cyclopenta[g]quinazolin-6-yl)amino]pyridine-2-carboxylate as a gum (0.185 g);

NMR Spectrum: (CDCl$_3$) 1.22 (s, 9H), 2.15 (m, 1H), 2.57 (m, 1H), 2.64 (s, 3H), 2.82 (s, 3H), 3.13 (m, 2H), 3.98 (s, 3H), 5.65 (t, 1H), 6.1 (2 d's, 2H), 7.15 (2d's, 1H), 7.52 (s, 1H), 8.03 (d, 1H), 8.06 (s, 1H), 87.35 (d, 1H).

(4) 5-[N-Methyl-N-((6RS)-2-methyl-4-oxo-3,4,7,8-tetrahydro-6H-cyclopenta-[g]quinazolin-6-yl)amino] pyridine-2-carboxylic acid A mixture of methyl 5-[N-methyl-N-((6RS)-2-methyl-4-oxo-3-pivaloyloxy-methyl-3,4,7,8-tetrahydro-6H-cyclopenta[g]quinazolin-6-yl)amino]pyridine-2-carboxylate (0.185 g), sodium hydroxide (0.06 g), water (2 ml) and methanol (10 ml) was stirred at ambient temperature for 18 hours. The mixture was evaporated. Water (20 ml) was added and the mixture was acidified to pH 5 by the addition of 2N aqueous hydrochloric acid. The precipitate was isolated, washed with water and dried under vacuum. There was thus obtained 5-[N-methyl-N-((6RS)-2-methyl-4-oxo-3,4,7,8-tetrahydro-6H-cyclopenta[g]quinazolin-6-yl)amino] pyridine-2-carboxylic acid (0.01 g).

(5) Pentafluorophenyl 5-[N-methyl-N-((6RS)-2-methyl-4-oxo-3,4,7,8-tetrahydro-6H-cyclopenta[g]quinazolin-6-yl) amino]pyridine-2-carboxylate A mixture of 5-[N-methyl-N-((6RS)-2-methyl-4-oxo-3,4,7,8-tetrahydro-6H-cyclopenta[g]quinazolin-6-yl)amino] pyridine-2-carboxylic acid (0.01 g), pentafluorophenyl trifluoroacetate (0.16 g; prepared by the reaction of pentafluorophenol and trifluoroacetic acid), pyridine (0.045 g) and DMA (5 ml) was stirred at ambient temperature for 5 hours. The mixture was evaporated and the residue was partitioned between ethyl acetate and a saturated aqueous sodium bicarbonate solution. The organic phase was dried (MgSO$_4$) and evaporated. The residue was purified by column chromatography using increasingly polar mixtures of ethyl acetate and methanol as eluant. There was thus obtained pentafluorophenyl 5-[N-methyl-N-((6RS)-2-methyl-4-oxo-3,4,7,8-tetrahydro-6H-cyclopenta[g]quinazolin-6-yl)amino]-pyridine-2-carboxylate as a foam (0.1 g);

NMR Spectrum: (CD$_3$SOCD$_3$) 2.1 (m, 1H), 2.35 (s, 3H), 2.55 (m, 1H), 2.81 (s, 3H), 3.1 (m, 2H), 5.98 (t, 1H), 7.48 (2 d's, 1H), 7.5 (s, 1H), 7.75 (s, 1H), 8.14 (d, 1H), 8.57 (d, H), 12.19 (s, 1H).

Example 7

Pentafluorophenyl 5-[N-((6RS)-2-methyl-4-oxo-3,4,7,8-tetrahydro-6H-cyclopenta[g]quinazolin-6-yl)-N-(prop-2-ynyl)amino]-pyridine-2-carboxylate (1) Methyl 5-[N-((6RS)-2-methyl-4-oxo-3-pivaloyloxymethyl-3,4,7,8-tetrahydro-6H-cyclopenta[g]quinazolin-6-yl)-N-(prop-2-ynyl)amino]-pyridine-2-carboxylate A solution of potassium tert-butoxide (8.6 g) in a mixture of tert-butanol (100 ml) and DMA (100 ml) was added dropwise during 20 minutes to a stirred solution of a mixture of 6-bromo-2-methyl-3-pivaloyloxymethyl-3,4,7,8-tetrahydro-6H-cyclopenta[g]quinazolin-4-one (30 g), prepared as described in section (6) of Example 1, and methyl 5-[N-(prop-2-ynyl)amino]-pyridine-2-carboxylate [14.5 g; obtained in quantitative yield by treating methyl 5-[N-(tert-butoxycarbonyl)-N-(prop-2-ynyl)amino]pyridine-2-carboxylate (J. Med. Chem., 1991, 1594) with trifluoroacetic acid at 0° C. for 1 hour] in DMA (300 ml) which had been cooled to −20° C. The mixture was allowed to warm to ambient temperature and was stirred for 24 hours. The mixture was evaporated. A mixture of ice and water (1 L) was added to the residue and the mixture was extracted with ethyl acetate. The organic phase was dried (MgSO$_4$) and evaporated. The residue was purified by column chromatography using initially increasingly polar mixtures of hexane and ethyl acetate and then a 19:1 mixture of methylene chloride and methanol as eluant. There was thus obtained methyl 5-[N-((6RS)-2-methyl-4-oxo-3-pivaloyloxymethyl-3,4,7,8-tetrahydro-6H-cyclopenta[g]quinazolin-6-yl)-N-(prop-2-ynyl)-amino]pyridine-2-carboxylate (10.1 g);

NMR Spectrum: (CDCl$_3$) 1.2 (s, 9H), 2.25 (t, 1H), 2.35 (m, 1H), 2.6 (m, 1H), 2.65 (s, 3H), 3.1 (m, 1H), 3.3 (m, 1H), 3.88 (2 d's, 1H), 3.98 (s, 3H), 4.03 (2 d's, 1H), 5.65 (t, 1H), 6.1 (2 d's, 2H), 7.3 (2 d's, 1H), 7.55 (s, 1H), 8.08 (d, 1H), 8.1 (s, 1H), 8.4 (s, 1H).

(2) 5-[N-((6RS)-2-Methyl-4-oxo-3,4,7,8-tetrahydro-6H-cyclopenta-[g]quinazolin-6-yl)-N-(prop-2-ynyl)amino] pyridine-2-carboxylic acid A mixture of methyl 5-[N-((6RS)-2-methyl-4-oxo-3-pivaloyloxy-methyl-3,4,7,8-tetrahydro-6H-cyclopenta[g]quinazolin-6-yl)-N-(prop-2-ynyl)amino]pyridine-2-carboxylate (1 g), sodium hydroxide (0.32 g), water (10 ml) and methanol (30 ml) was stirred at ambient temperature for 24 hours. The mixture was evaporated. Water (60 ml) was added and the mixture was acidified to pH 5 by the addition of 2N aqueous hydrochloric acid. The precipitate was isolated, washed with water and dried under vacuum. There was thus obtained 5-[N-((6RS)-2-methyl-4-oxo-3,4,7,8-tetrahydro-6H-cyclopenta[g]quinazolin-6-yl)-N-(prop-2-ynyl)amino]pyridine-2-carboxylic acid (0.68 g);

NMR Spectrum: (CD$_3$SOCD$_3$) 2.25 (m, 1H), 2.3 (s, 3H), 2.5 (m, 1H), 3.0 (s, 1H), 3.05 (m, 2H), 3.9 (2 d's, 1H), 4.15 (2 d's, 1H), 5.8 (t, 1H), 7.4 (2 d's, 1H), 7.5 (s, 1H), 7.8 (s, 1H), 7.9 (d, 1H), 8.35 (d, 1H).

(3) Pentafluorophenyl 5-[N-((6RS)-2-methyl-4-oxo-3,4,7,8-tetrahydro-6H-cyclopenta[g]quinazolin-6-yl)-N-(prop-2-ynyl)amino]-pyridine-2-carboxylate Using an analogous procedure to that described in section (5) of Example 6, 5-[N-((6RS)-2-methyl-4-oxo-3,4,7,8-tetrahydro-6H-cyclopenta[g]quinazolin-6-yl)-N-(prop-2-ynyl)]pyridine-2-carboxylic acid was reacted with pentafluorophenyl trifluoroacetate to give pentafluorophenyl 5-[N-((6RS)-2-methyl-4-oxo-3,4,7,8-tetrahydro-6H-cyclopenta[g]quinazolin-6-yl)-N-(prop-2-ynyl)amino]-pyridine-2-carboxylate as a foam.

Example 8

(2S)-2-{o-Fluoro-p-[-methyl-N-((6RS)-2-methyl-4-oxo-3,4,7,8-tetrahydro-6H-cyclopenta[g]quinazolin-6-yl)amino]-benzamido}-2-[p-(carboxy-methyl) phenyl]acetic acid (1) α-tert-Butoxycarbonylamino-p-hydroxyphenylacetic acid To an aqueous solution of L(+)-α-amino-p-hydroxyphenylacetic acid (10 g, 60 mmol) and NaHCO$_3$ (5.1 g, 60 mmol) in 80 ml of water was added dropwise a solution of di-tert-butyl-di-carbonate (14.4 g, 66 mmol) in 80 ml of dioxane. Stirring was maintained for 24 hours. The reaction mixture was then diluted with water and extracted with ether. The aqueous layers were acidified (pH 2.5) with 6N HCl and extracted with ether. The resulting ether layers were washed with brine, dried (MgSO$_4$) and evaporated to give α-tert-butoxycarbonylamino-p-hydroxyphenylacetic acid (17 g) as a white foam in quantitative yield.

(2) Methyl α-tert-butoxycarbonylamino-p-hydroxyphenylacetate

Diazomethane was bubbled through a solution of α-tert-butoxycarbonylamino-p-hydroxyphenylacetic acid (17 g, 60 mmol) in 200 ml of ether cooled to 0° C. until a yellow colour appeared when the excess of diazomethane was immediately destroyed with acetic acid. The solution was evaporated to dryness. Trituration of the resulting crude oil with hexane/ether gave methyl α-tert-butoxycarbonylamino-p-hydroxyphenyl acetate (14.8 g, 94%) as a white solid, m.p. 138°–139.4° C.;

NMR Spectrum: (CDCl$_3$) 1.68 (s, 9H), 3.7 (s, 3H), 5.2 (d, 1H), 5.5 (m, 1H), 5.8 (s, 1H), 6.74 (d, 2H), 7.2 (d, 2H).

(3) Methyl α-tert-butoxycarbonylamino-p-trifluoromethanesulphonyloxyphenyl-acetate To a solution of methyl α-tert-butoxycarbonylamino-p-hydroxyphenylacetate (14.3 g, 51 mmol) in 50 ml of pyridine cooled to 0° C. under stirring was added dropwise trifluoromethanesulphonic acid anhydride (15.8 g, 56 mmol). Stirring was maintained for 6 hours. The red solution was diluted with water and extracted with ether. The organic layers were washed in turn with 1N HCl, water and brine, dried (MgSO$_4$), filtered and evaporated to give an oil which after trituration with hexane crystallized to give methyl α-tert-butoxycarbonylamino-p-trifluoromethanesulphonyloxyphenyl-acetate (1 9.3 g, 92%) as a white solid, m.p. 67°–67.6° C.;

NMR Spectrum: (CDCl$_3$) 1.4 (s, 9H), 3.74 (s, 3H), 5.35 (s, 1H), 5.7 (s, 1H), 7.25 (d, 2H).

(4) Methyl p-allyl-α-tert-butoxycarbonylaminophenylacetate

To a solution of methyl α-tert-butoxycarbonylamino-p-trifluoromethane-sulphonyloxyphenylacetate (8.26 g, 20 mmol) in DMF (60 ml) was added under stirring LiCl (2.1 g, 50 mmol) and tributyl tin allyl (7.6 g, 23 mmol). The flask was purged six times with argon. $PdCl_2[P(C_6H_5)_3]_2$ was added rapidly to the reaction mixture and after purging the flask twice more with argon the reaction mixture was heated at 100° C. for 90 minutes. After evaporation of the DMF, the green oil was diluted with water and extracted with ether. The organic layers were washed with water and brine, dried and evaporated to give a yellow oil (17 g). Purification by flash chromatography gave methyl p-allyl-α-tert-butoxycarbonylaminophenylacetate (4.95 g, 81%) as a yellow oil which crystallized when triturated with hexane, m.p. 60.6°–62° C.;

NMR Spectrum: ($CDCl_3$) 1.42 (s, 9H), 3.36 (s, 2H), 3.7 (s, 3H), 5.05 (m, 2H), 5.3 (d, 1H), 5.5 (m, 1H), 5.95 (m, 1H), 7.15 (d, 2H), 7.25 (d, 2H).

(5) Methyl α-tert-butoxycarbonylamino-p-carboxymethylphenylacetate

To a solution of methyl p-allyl-α-tert-butoxycarbonylamino- phenylacetate (2.44 g, 8 mmol) in acetonitrile (20 ml) and carbon tetrachloride (20 ml) was added under stirring 30 ml of water followed by $NaIO_4$ (6.8 mg, 0.032 mmol) and $RuO_2 \cdot 1H_2O$ (50 mg). After 6 hours stirring 0.5 ml of methanol was added and stirring was maintained for a further 10 minutes. The reaction mixture was diluted with water, acidified to pH 3 and extracted with dichloromethane. The organic layers were dried ($MgSO_4$) and evaporated to give a grey solid which was further purified by acid/base extraction to give methyl α-tert-butoxycarbonylamino-p-carboxymethylphenylacetate (1.37 g, 53%) as a white solid, m.p. 123.2°–124° C.;

NMR Spectrum: ($CDCl_3$) 1.42 (s, 9H), 3.63 (s, 2H), 3.71 (s, 3H), 5.31 (d, 1H), 5.55 (s, 1H), 7.2–7.4 (m, 4H).

(6) Methyl α-tert-butoxycarbonylamino-p-methoxycarbonylmethylphenylacetate

Diazomethane was bubbled through a solution of methyl α-tert-butoxycarbonyl-amino-p-carboxymethylphenylacetate (2.75 g, 8.5 mmol) in 50 ml of ether and 10 ml of $CH_2Cl_2$ at 0° C. until a yellow colour appeared. The solution was then evaporated to dryness to give methyl α-tert-butoxycarbonylamino-p-methoxycarbonylmethylphenyl-acetate (2.9 g, 100%) as a yellow oil which crystallized on standing;

NMR Spectrum: ($CDCl_3$) 1.45 (s, 9H), 3.61 (s, 2H), 3.69 (s, 3H), 3.71 (s, 3H), 5.3 (s, 1H), 5.55 (s, 1H), 7.3 (d, 2H), 7.4 (d, 2H).

(7) Methyl α-amino-p-methoxycarbonylmethylphenylacetate

To a solution of methyl α-tert-butoxycarbonylamino-p-methoxycarbonylmethyl-phenylacetate (2.86 g, 8.5 mmol) in $CH_2Cl_2$ (10 ml) cooled at 0° C. was added 10 ml of TFA. After stirring for 1 hour at room temperature the reaction mixture was evaporated to dryness. The resulting solid was dissolved in ethyl acetate and water and the pH was adjusted to 8 with $NaHCO_3$. After extraction with ethyl acetate the organic layers were washed with brine, dried and evaporated to give a yellow oil. After dissolution of this oil in a mixture of ether:methanol (10:1 v/v) a saturated solution of HCl in ether was added to give, after filtration, methyl α-amino-p-methoxycarbonyl-methylphenylacetate (2.2 g, 96%) as a white solid, m.p. 189.2°–189.6° C.;

NMR Spectrum: (DMSO) 3.6 (s, 3H), 3.7 (s, 5H), 5.26 (s, 1H), 7.35 (s, 2H), 7.45 (s, 2H), 9.0 (s, 2H).

(8) (RS)-α- Amino-p-carboxymethylphenylacetic acid

A suspension of methyl α-amino-p-methoxycarbonylmethylphenylacetate (2.3 g, 7 mmol) in 60 ml of 6N HCl was refluxed for 12 hours. After cooling white needles were collected. The aqueous layers were extracted with ethyl acetate. The organic layers were evaporated and the solids combined to give (RS)-α-amino-p-carboxymethylphenylacetic acid (1.45 g, 83%);

NMR Spectrum: (DMSO/TFA) 3.6 (s, 3H), 5.1 (s, 1H), 7.3 (d, 2H), 7.45 (d, 2H).

(9) (S)-α-Amino-p-carboxymethylphenylacetic acid

To a suspension of (RS)-α-amino-p-carboxymethylphenylacetic acid (3.2 g, 15 mmol) in 50 ml of water was added S(–)phenylethylamine (1.85 g, 15 mmol) dropwise. The resulting solution was left standing overnight at room temperature. The resulting crystals were filtered off, washed with cold water and dried to give a solid (2.3 g). The solid was recrystallized with 30 ml of water. After standing overnight the resulting solid was filtered off. It was then dissolved in 2N HCl (3 equivalents) and 2 equivalents of propylene oxide were added to the solution with stirring. After 30 minutes cooling at 0° C., filtration gave (S)-α-amino-p-carboxymethyl-phenylacetic acid as a solid, m.p. 250°–250.4;

NMR Spectrum: (DMSO/TFA) 3.6 (s, 2H), 5.15 (s, 1H), 7.35 (d, 2H), 7.45 (d, 2H).

Optical Activity: (1N HCl) $[\alpha]_D^{25°}$ +106.7° (c=1)

(10) (2S)-2-{o-Fluoro-p-[N-methyl-N-((6RS)-2-methyl-4-oxo-3-pivaloyloxy-methyl-3,4,7,8-tetrahydro-6H-cyclopenta[g]quinazolin-6-yl)amino]benzamido}-2-[p-(carboxymethyl)phenyl]acetic acid To a solution of (S)-α-amino-p-carboxymethylphenylacetic acid (0.1 g, 0.48 mmol) and pentafluorophenyl o-fluoro-p-[N-methyl-N-((6RS)-2-methyl-4-oxo-3-pivaloyloxymethyl-3,4,7,8-tetrahydro-6H-cyclopenta[g]quinazolin-6-yl)amino]-benzoate (0.213 g, 0.4 mmol), prepared as described in Example 2, in 5 ml of DMF was added bistrimethyl silyl acetamide (BSA) (0.194 g, 0.96 mmol). After stirring under $N_2$ for 20 minutes N-methylmorpholine was added (0.081 g, 0.8 mmol) followed by N-hydroxybenzotriazole (HOBT) (0.01 g). The reaction mixture was stirred at room temperature for 4 hours and evaporated to dryness. The solid obtained by trituration with ether and filtration was resuspended in a mixture of methanol/water (2 ml) and the pH adjusted to 2.5 with 2N HCl. The resulting precipitate was filtered off, washed with water and dried to give (2S)-2-{o-fluoro-p-[N-methyl-N-(6RS)-2-methyl-3-pivaloyloxymethyl-4-oxo-3,4,7,8-tetrahydro-6H-cyclopenta[g]quinazolin-6-yl)amino]-benzamido}-2-[p-(carboxymethyl)phenyl]acetic acid (140 mg, 64%) as a yellow solid;

NMR Spectrum: (DMSO/TFA) 1.14 (s, 9H), 2–2.15 (m, 1H), 2.5 (m, 1H), 2.65–2.8 (m, 6H), 3–3.1 (m, 1H), 3.15–3.25 (m, 1H), 3.55 (s, 2H), 5.55 (s, 1H), 5.8 (t, 1H), 6.1 (q, 2H), 6.8–6.95 (m, 2H), 7.25 (d, 2H), 7.4 (d, 2H), 7.6 (s, 1H), 7.65 (t, 1H), 7.8 (s, 1H).

(11) (2S)-2-{o-Fluoro-p-[N-methyl-N-((6RS)-2-methyl-4-oxo-3,4,7,8-tetrahydro-6H-cyclopenta[g]quinazolin-6-yl)amino]benzamido}-2-[p-(carboxymethyl)phenyl]-acetic acid A solution of (2S)-2-{o-fluoro-p-[N-methyl-N-((6RS)-2-methyl-3-pivaloyloxy-methyl-4-oxo-3,4,7,8-tetrahydro-6H-cyclopenta[g]quinazolin-6-yl)amino]benzamido}-2-[p-(carboxymethyl)phenyl]acetic acid (0.14 g, 0.2 mmol) in 1 ml of methanol containing 0.6 ml of 1N NaOH was stirred for 90 minutes at room temperature. After dilution with water and filtration the pH was adjusted to 2.5 with 2N HCl. The resulting solid was filtered off, washed with water, dried and triturated with ether to give (2S)-2-{o-fluoro-p-[N-methyl-N-((6RS)-2-methyl-4-oxo-3,4,7,8-tetrahydro-6H-cyclopenta[g]quinazolin-6-yl)amino]benzamido}-2-[p-

(carboxymethyl)phenyl]acetic acid (0.103 g, 93%) as a white solid, m.p. 196°–200° C.;

NMR Spectrum: (DMSO/TFA) 2.05–2.2 (m, 1H), 2.5 (m, 1H), 2.66 (s, 3H), 2.68 (s, 3H), 3–3.15 (m, 1H), 3.2–3.3 (m, 1H), 3.58 (s, 2H), 5.5 (s, 1H), 5.87 (t, 1H), 6.8–6.9 (m, 2H), 7.3 (d, 2H), 7.45 (d, 2H), 7.65 (s, 1H), 7.68 (t, 1H), 7.78 (s, 1H).

Mass Spectrum: (FAB) 559 [(M+H)$^+$], 581 [(M+Na)$^+$].
Elemental Analysis: Found C, 62.9; H, 5.2; N, 9.9;
$C_{30}H_{27}FN_4O_6$ 1 $H_2O$ requires C, 62.5; H, 5.07; N, 9.7.
The enantiomeric purity as measured by chiral HPLC was 95% (2S): 5% (2R).

Example 9

(2R)-2-{o-Fluoro-p-[N-methyl-N-((6RS)-2-methyl-4-oxo-3,4,7,8-tetrahydro-6H-cyclopenta[g]quinazolin-6-yl)amino]benzamido}-2-[p-(carboxymethyl)phenyl]acetic acid (1) (R)-α-Amino-p-carboxymethylphenylacetic acid To a suspension of (RS)-α-amino-p-carboxymethylphenylacetic acid (5.4 g, 26 mmol), prepared as described in Example 8(8), in 23 ml of water was added R(+)phenylethylamine (3.13 g, 26 mmol) dropwise. The resulting solution was left standing overnight at room temperature. The crystals were then filtered off, washed with cold water and dried to give a solid (2.5 g). The solid was recrystallized with 32 ml of water. After standing overnight the resulting solid was filtered off. It was then dissolved in 2N HCl (3 equivalents) and 2 equivalents of propylene oxide were added to the solution with stirring. After 2 hours cooling at 0° C., filtration gave (R)-α-amino-p-carboxymethylphenylacetic acid (1.2 g, 44%) as a solid, m.p. 249°–250° C.;

NMR Spectrum: (DMSO/TFA) 3.6 (s, 2H), 5.15 (s, 1H), 7.35 (d, 2H), 7.45 (d, 2H).

Optical Rotation: (IN HCl ) $[\alpha]_D^{25°}$ –107.5° (c=1).

(2) (2R)-2-{o-Fluoro-p-[N-methyl-N-((6RS)-2-methyl-4-oxo-3-pivaloyloxy-methyl-3,4,7,8-tetrahydro-6H-cyclopenta[g]quinazolin-6-yl)amino]benzamido}-2-[p-(carboxymethyl)phenyl]acetic acid A solution of (R)-α-amino-p-carboxymethylphenylacetic acid (0.1 g, 0.48 mmol) and bis trimethylsilyl acetamide (0.195 g, 0.96 mmol in 5 ml of DMF) was stirred for 20 minutes at room temperature. To the solution was then added pentafluorophenyl o-fluoro-p-[N-methyl-N-((6RS)-2-methyl-4-oxo-3-pivalyloxymethyl-3,4,7,8-tetrahydro-6H-cyclopenta[g]quinazolin-6-yl)amino]benzoate (0.213 g, 0.4 mmol), prepared as described in Example 2, followed by N-hydroxybenzotriazole (10 mg) and the stirring was maintained for a further 5 hours. The reaction mixture was then evaporated to dryness and the crude material redissolved in ether. The ether layers were extracted with NaHCO$_3$. The aqueous layers were acidified to pH 2.5 with 2N HCl and the precipiate was filtered off, washed with water and dried under vacuum to give (2R)-2-{o-fluoro-p-[N-methyl-N-((6RS)-2-methyl-4-oxo-3-pivaloyloxymethyl-3,4,7,8-tetrahydro-6H-cyclopenta[g]quinazolin-6-yl)amino]benzamido}-2-[p-(carboxy-methyl)phenyl]acetic acid (0.19 g), 85%) as a white solid;

NMR Spectrum: (DMSO) 1.13 (s, 9H), 2–2.15 (m, 1H), 2.5 (m, 1H), 2.6 (s, 3H), 2.7 (s, 3H), 2.95–3.05 (m, 1H), 3.1–3.2 (m, 1H), 3.55 (s, 2H), 5.5 (d, 1H), 5.8 (t, 1H), 6.05 (q, 2H), 6.8–6.9 (m, 2H), 7.25 (d, 2H), 7.4 (d, 2H), 7.55 (s, 1H), 7.65 (t, 1H), 7.72 (s, 1H), 8.15 (t, 1H).

(3) (2R)-2-{o-Fluoro-p-[N-methyl-N-((6RS)-2-methyl-4-oxo-3,4,7,8-tetrahydro-6H-cyclopenta[g]quinazolin-6-yl)amino]benzamido}-2-[p-(carboxymethyl)phenyl]-acetic acid A suspension of (2R)-2-{o-fluoro-p-[N-methyl-N-((6RS)-2-methyl-4-oxo-3-pivaloyloxymethyl-3,4,7,8-tetrahydro-6H-cyclopenta[g]quinazolin-6-yl)amino]-benzamido}-2-[p-(carboxymethyl)phenyl]-acetic acid (0.190 g, 0.34 mmol) in 1.5 ml of methanol containing 1 ml of 1N NaOH was stirred at room temperature for 90 minutes. After dilution with water the pH was adjusted to 2.5 with 2N HCl . The precipitate was filtered off, washed with water and dried under vacuum to give (2R)-2-{o-fluoro-p[N-methyl-N-((6RS)-2-methyl-4-oxo-3,4,7,8-tetrahydro-6H-cyclopenta[g]quinazolin-6-yl)amino]benzamido}-2-[p-(carboxymethyl)phenyl]acetic acid (0.135 g, 71%) as a white solid, m.p. 195°–198° C;

NMR Spectrum: (DMSO/TFA) 2.05–2.15 (m, 1H), 2.5 (m, 1H), 2.66 (s, 3H), 2.68 (s, 3H), 3.0–3.15 (m, 1H), 3.2–3.3 (m,1H), 3.58 (s, 2H), 5.52 (s, 1H), 5.85 (t,1H), 6.8–6.9 (m, 2H), 7.25 (d, 2H), 7.45 (d, 2H), 7.65 (s, 1H) 7.68 (t, 1H), 7.78 (s, 1H).

Mass Spectrum: (FAB) 559 [(M+H)$^+$], 581 [(M+Na)$^+$].
Elemental Analysis: Found C, 62.2; H, 5.08; N, 9.79;
$C_{30}H_{27}FN_4O_6$ 1.1 $H_2O$ requires C, 62.3; H, 5.09; N, 9.69.
Enantiomeric purity as measured by chiral HPLC was 91% (2R): 9% (2S).

Example 10

(2S)-2-{o-Fluoro-p-[N-methyl-N-((6RS)-2-methyl-4-oxo-3,4,7,8-tetrahydro-6H-cyclopenta[g]quinazolin-6-yl)amino]benzamido}-4-(2-carboxymethyl-tetrazol-5-yl)butyric acid (1) Methyl (2S)-2-benzyloxycarbonylamino-4-cyanobutyrate A solution of N-benzyloxycarbonyl-L-glutamine methyl ester (25 g) in THF (500 ml) was added dropwise to a stirred solution of triphenylphosphine (44.5 g) in carbon tetrachloride (1 L). The mixture was heated to 50° C. for 2 hours. The mixture was evaporated. The resultant oil was triturated in ethyl acetate. The mixture was filtered and the filtrate was evaporated. The residue was purified by column chromatogaphy using a 1:1 mixture of hexane and ethyl acetate as eluant. There was thus obtained methyl (2S)-2-benzyloxycarbonylarnino-4-cyanobutyrate (19.38 g, 83%).

(2) Methyl (2S)-2-benzyloxycarbonylamino-4-(tetrazol-5-yl)butyrate

A mixture of methyl (2S)-2-benzyloxycarbonylamino-4-cyanobutyrate (10 g), tri-n-butyltin azide [prepared according to the method in Rec. Trav. Chim. Pavs-Bas, 1963, 81, 286; 12 g] and THF (60 ml) was stirred and heated to reflux for 40 hours. The mixture was evaporated. The resultant brown oil was triturated in diethyl ether which had been saturated with hydrogen chloride gas. The precipitate was isolated and washed with diethyl ether. There was thus obtained methyl (2S)-2-benzyloxycarbonyl-amino-4-(tetrazol-5-yl)butyrate (2.23 g, 32%);

NMR Spectrum: (CD$_3$SOCD$_3$) 1.95–2.35 (m, 2H), 2.95 (t, 2H), 3.64 (s, 3H), 4.15 (m, 1H), 5.04 (s, 2H), 7.36 (s, 5H), 7.88 (d, 1H), 13.0 (s, 1H).

(3) Methyl (2S)-2-(benzyloxycarbonylamino)-4-(2-methoxycarbonylmethyltetrazol-5-yl)butyrate and Methyl (2S)-2-(benzyloxycarbonylamino)-4-(1-methoxycarbonylmethyltetrazol-5-yl)butyrate To a stirred solution of methyl bromoacetate (2.45 g, 16.0 mmol) in anhydrous dichloromethane (35 ml) under argon was added methyl (2S)-2-(benzyloxycarbonyl-amino)-4-(tetrazol-5-yl)butyrate (2.55 g, 8.0 mmol) and then triethylamine (0.970 g, 9.6 mmol). The resultant solution was stirred at room temperature for 3 hours, then diluted with ethyl acetate (200 ml) and washed with saturated aqueous sodium bicarbonate (2×150 ml) and water (150 ml), dried (Na₂SO₄) and concentrated. Purification by column chromatography, on gradient elution with ethyl acetate in dichloromethane (20 to 40%), gave in order of elution:

(a) Methyl (2S)-2-(benzyloxycarbonylamino)-4-(2-methoxycarbonylmethyltetrazol-5-yl)butyrate (0.95 g, 30%) as a colourless oil;

NMR Spectrum: (CD$_3$SOCD$_3$) 1.98–2.20 (m, 2H, 3-CH$_2$), 2.95 (t, J=7.0 Hz, 2H, 4-CH$_2$), 3.64, 3.72 (2×s, 6H, 2×CO$_2$CH$_3$), 4.15 (m, 1H, 2-CH), 5.05 (s, 2H, PhCH$_2$), 5.79 (s, 2H, CH$_2$CO$_2$CH$_3$), 7.36 (m, 5H, ArH), 7.92 (d, J=7.8 Hz, 1H, CONH).

Mass Spectrum: (CI) m/e 392 [(M+H)⁺].

Elemental Analysis: Found C, 52.02; H, 5.46; N, 17.65; C$_{17}$H$_{21}$N$_5$O$_6$ requires C, 52.17; H, 5.41; N, 17.89%.

(b) Methyl (2S)-2-(benzyloxycarbonylamino)-4-(1-methoxycarbonylmethyltetrazol-5-yl)butyrate (1.55 g, 49%) as a white solid, m.p. 91°–94° C.

NMR Spectrum: (CD$_3$SOCD$_3$) 1.95–2.18 (m, 2H, 3-CH$_2$), 2.92 (m, 2H, 4-CH$_2$), 3.64, 3.72 (2×s, 6H, 2×CO$_2$CH$_3$), 4.24 (m, 1H, 2-CH), 5.05 (s, 2H, PhCH$_2$), 5.51 (s, 2H, CH$_2$CO$_2$CH$_3$), 7.36 (m, 5H, ArH), 7.87 (d, J=7.9Hz, 1H, CONH).

Mass Spectrum: (CI) m/e 392 [(M+H)⁺].

Elemental Analysis: Found C, 52.13; H, 5.43; N, 17.64; C$_{17}$H$_{21}$N$_5$O$_6$ requires C, 52.17; H, 5.41; N, 17.89%.

(4) Methyl (2S)-2-amino-4-(2-methoxycarbonylmethyltetrazol-5-yl)butyrate

To a solution of methyl (2S)-2-(benzyloxycarbonylamino)-4-(2-methoxycarbonylmethyltetrazol-5-yl)butyrate (0.820 g, 2.10 mmol) in ethyl acetate (100 ml) was added 10% Pd/C (0.220 g). The black reaction mixture was stirred at room temperature for 15 hours under a hydrogen atmosphere. The catalyst was removed by filtration and the filtrate was concentrated to give methyl (2S)-2-amino-4-(2-methoxycarbonylmethyltetrazol-5-yl)butyrate (0.410 g, 76%) as a colourless oil. This was immediately used in section (5) below without further purification.

(5) Methyl (2S)-2-{o-fluoro-p-[N-methyl-N-((6RS)-2-methyl-4-oxo-3-pivaloyloxy-methyl-3,4,7,8-tetrahydro-6H-cyclopenta[g]quinazolin-6-yl)amino]benzamido}-4-(2-methoxycarbonylmethyltetrazol-5-yl)butyrate To a stirred solution of methyl (2S)-2-amino-4-(2-methoxycarbonylmethyl-tetrazol-5-yl)butyrate (74 mg) in anhydrous DMF (1.2 ml) under argon was added pentafluorophenyl o-fluoro-p-[N-methyl-N-((6RS)-2-methyl-4-oxo-3-pivaloyloxy-methyl-3,4,7,8-tetrahydro-6H-cyclopenta[g]quinazolin-6-yl)amino]benzoate (129 mg), prepared as described in Example 2, followed by a catalytic amount of N-hydroxybenzotriazole (2.8 mg). The resultant yellow solution was stirred at room temperature for 16 hours under argon and then partitioned between ethyl acetate (50 ml) and water (40 ml). The two layers were separated and the organic layer was washed with saturated aqueous sodium bicarbonate (40 ml) and water (40 ml), dried (Na$_2$SO$_4$), and concentrated. Purification by column chromatography on gradient elution with ethyl acetate in dichloromethane (50 to 60%) afforded a gum which was triturated with hexanes. The precipitated solid was collected by filtration and washed with hexanes (10 ml). There was thus obtained methyl (2S)-2-{o-fluoro-p-[N-methyl-N-((6RS)-2-methyl-4-oxo-3-pivaloyloxymethyl-3,4,7,8-tetrahydro-6H-cyclopenta-[g]quinazolin-6-yl)amino]benzamido}-4-(2-methoxycarbonylmethyltetrazol-5-yl)-butyrate (103 mg) as a white solid, m.p. 86°–88° C. (softens);

NMR Spectrum: (CD$_3$SOCD$_3$) 1.13 (s, 9H, C(CH$_3$)$_3$), 2.10, 2.25, 2.45 (3×m, 4H, 3-CH$_2$ and cyclopenta[g]quinazoline 7-CH$_2$), 2.59, 2.66 (2×s, 6H, cyclopenta[g]quinazoline 2-CH$_3$ and N—CH$_3$), 2.95–3.22 (m, 4H, 4-CH$_2$ and cyclopenta[g]quinazoline 8-CH$_2$), 3.66, 3.72 (2×s, 6H, 2×CO$_2$CH$_3$), 4.53 (m, 1H, 2-CH), 5.79 (m, 2H, CH$_2$CO$_2$CH$_3$) and cyclopenta[g]quinazoline 6-CH), 6.03 (ABq, J=10.9 Hz, 2H, (CH$_3$)$_3$CCO$_2$CH$_2$), 6.82 (d, J=13.9 Hz, 1H, 3'-ArH), 6.86 (d, J=7.4 Hz, 1H, 5'-ArH), 7.53 (s, 1H, cyclopenta[g]quinazoline 9-H), 7.59 (t, J=8.9 Hz, 1H, 6'-ArH), 7.72 (s, 1H, cyclopenta[g]quinazoline 5-H), 8.26 (dd, J=4.4, 11.6 Hz, 1H, CONH).

Mass Spectrum: (ESI) m/e 721 [(M+H)⁺].

(6) (2S)-2-{o-Fluoro-p-[N-methyl-N-((6RS)-2-methyl-4-oxo-3,4,7,8-tetrahydro-6H-cyclopenta[g]quinazolin-6-yl)amino]benzamido}-4-(2-carboxymethyltetrazol-5-yl)-butyric acid To a solution of methyl (2S)-2-{o-fluoro-p-[N-methyl-N-((6RS)-2-methyl-4-oxo-3-pivaloyloxymethyl-3,4,7,8-tetrahydro-6H-cyclopenta[g]quinazolin-6-yl)amino]-benzamido}-4-(2-methoxycarbonylmethyltetrazol-5-yl)butyrate (87 mg) in methanol (2 ml) was slowly added an aqueous solution of NaOH (1N, 0.72 ml). The resultant solution was stirred at room temperature for 4 hours then more aqueous 1N NaOH (0.36 ml) was added and stirring was continued at room temperature for 1 hour. Next the solution was diluted with water (3 ml) and acidified to pH 4 with 1N hydrochloric acid. The precipitated solid was collected by filtration, washed with water (15 ml), and dried in vacuo over phosphorus pentoxide. There was thus obtained (2S)-2-{o-fluoro-p-[N-methyl-N-((6RS)-2-methyl-4-oxo-3,4,7,8-tetrahydro-6H-cyclopenta[g]quinazolin-6-yl)-amino]benzamido}-4-(2-carboxymethyltetrazol-5-yl)butyric acid (57 mg) as a pale yellow solid, m.p. 196°–199° C.;

NMR Spectrum: (CD$_3$SOCD$_3$) 2.03, 2.25, 2.44 (3×m, 4H, 3-CH$_2$ and cyclopenta[g]quinazoline 7-CH$_2$), 2.33, 2.66 (2×s, 6H, cyclopenta[g]quinazoline 2-CH$_3$ and N-CH$_3$), 2.92–3.22 (m, 4H, 4-CH$_2$ and cyclopenta[g]quinazoline 8-CH$_2$), 4.46 (m, 1H, 2-CH), 5.54 (s, 2H, CH$_2$CO$_2$CH$_3$), 5.79 (t, J=7.9 Hz, 1H, cyclopenta[g]quinazoline 6-CH), 6.88 (m, 2H, 3',5'-ArH), 7.48 (s, 1H, cyclopenta[g]quinazoline 9-H), 7.62 (t, J=8.9 Hz, 1H, 6'-ArH), 7.68 (s, 1H, cyclopenta[g]quinazoline 5-H), 8.08 (t, J=6.9 Hz, 1H, CONH), 12.17 (s, 1H, lactam NH).

Mass Spectrum: (ESI) m/e 579 [(M+H)⁺].

Elemental Analysis: Found C, 53.51; H, 4.82; N, 18.43; C$_{27}$H$_{27}$FN$_8$O$_6$ 1.5 H$_2$O requires C, 53.55; H, 4.99; N, 18.50%.

Example 11

(2S)-2-{o-Fluoro-p-[N-methyl-N-((6RS)-2-methyl-4-oxo-3,4,7,8-tetrahydro-6H-cyclopenta[g]quinazolin-6-yl)amino]benzamido}-4-(1-carboxymethyl-tetrazol-5-yl)butyrate acid (1) Methyl (2S)-2-amino-4-(1-methoxycarbonylmethyltetrazol-5-yl)butyrate The procedure described in section (4) of Example 10 was repeated using methyl (2S)-2-(benzyloxycarbonylamino)-4-(1-methoxycarbonylmethyltetrazol-5-yl)butyrate (0.470 g, 1.20 mmol), prepared as described in section (3) of Example 10, ethyl acetate (55 ml) and 10% Pd/C (0.120 g). There was thus obtained methyl (2S)-2-amino-4-(1-methoxycarbonylmethyltetrazol-5-yl)butyrate (0.310 g, 98%) as a colourless oil. This was immediately used in section (2) below without further purification.

(2) Methyl (2S)-2-{o-fluoro-p-[N-methyl-N-((6RS)-2-methyl-4-oxo-3-pivaloyl-oxymethyl-3,4,7,8-tetrahydro-6H- cyclopenta[g]quinazolin-6-yl)amino]benzamido}-4-(1-methoxycarbonylmethyltetrazol-5-yl)butyrate The procedure described in section (5) of Example 10 was repeated using methyl (2S)-2-amino-4-(1-methoxycarbonylmethyl-tetrazol-5-yl)butyrate (64 mg), anhydrous DMF (1.2 ml), pentafluorophenyl o-fluoro-p-[N-methyl-N-((6RS)-2-methyl-4-oxo-3-pivaloyloxymethyl-3,4,7,8-tetrahydro-6H-cyclopenta[g]quinazolin-6-yl)amino] benzoate (129 mg), prepared as described in Example 2, and a catalytic amount of N-hydroxybenzotriazole (2.8 mg). The crude product was purified by column chromatography using a gradient of ethyl acetate in dichloromethane (70 to 80%) as eluant. Subsequent reprecipitation from ethyl acetate (3 ml)/hexanes gave a white solid which was collected by filtration and dried in vacuo over phosphorus pentoxide. There was thus obtained methyl (2S)-2-{o-fluoro-p-[N-methyl-N-((6RS)-2-methyl-4-oxo-3-pivaloyloxymethyl-3,4,7,8-tetrahydro-6H-cyclopenta[g]quinazolin-6-yl)amino]-benzamido}-4-(1-methoxycarbonylmethyltetrazol-5-yl)-butyrate (93 mg) as a white solid, m.p. 95° C. (softens);

NMR Spectrum: (CD$_3$SOCD$_3$) 1.12 (s, 9H, C(CH$_3$)$_3$), 2.05, 2.25, 2.44 (3×m, 4H, 3-CH$_2$ and cyclopenta[g]quinazoline 7-CH$_2$), 2.59, 2.66 (2×s, 6H, cyclopenta[g]quinazoline 2-CH$_3$ and N-CH$_3$), 2.91–3.20 (m, 4H, 4-CH$_2$ and cyclopenta[g]quinazoline 8-CH$_2$), 3.65, 3.71 (2×s, 6H, 2x CO$_2$CH$_3$), 4.56 (m, 1H, 2-CH), 5.52 (s, 2H, C$\underline{H}_2$CO$_2$CH$_3$), 5.80 (t, J=8.0 Hz, 1H, cyclopenta[g]quinazoline 6-CH), 6.03 (ABq, J=10.9 Hz, 2H, (CH$_3$)$_3$CO$_2$C$\underline{H}_2$), 6.84 (m, 2H, 3',5'-ArH), 7.53 (s, 1H, cyclopenta[g]quinazoline 9-H), 7.59 (t, J=9.3 Hz, 1H, 6'-ArH), 7.71 (s, 1H, cyclopenta[g]quinazoline 5-H), 8.24 (dd, J=7.3, 12.1 Hz, 1H, CONH).

Mass Spectrum: (ESI) m/e 721 [(M+H)$^+$].

(3) (2S)-2-{o-Fluoro-p-[N-methyl-N-((6RS)-2-methyl-4-oxo-3,4,7,8-tetrahydro-6H-cyclopenta[g]quinazolin-6-yl)amino]benzamido}-4-(1-carboxymethyltetrazol-5-yl)-butyric acid The procedure described in section (6) of Example 10 was repeated using methyl (2S)-2-{o-fluoro-p-[N-methyl-N-((6RS)-2-methyl-4-oxo-3-pivaloyloxymethyl-3,4,7,8-tetrahydro-6H-cyclopenta[g]quinazolin-6-yl)amino]benzamido}-4-(1-methoxycarbonyl-methyltetrazol-5-yl) butyrate (70 mg), methanol (1.8 ml) and an aqueous solution of NaOH (1N, 0.6 ml). The resultant solution was stirred at room temperature for 4 hours, then more aqueous 1N NaOH (0.3 ml) was added and stirring was continued at room temperature for 1 hour. There was thus obtained (2S)-2-{o-fluoro-p-[N-methyl-N-((6RS)-2-methyl-4-oxo-3,4,7,8-tetrahydro-6H-cyclopenta[g]quinazolin-6-yl)-amino] benzamido}-4-(1-carboxymethyltetrazol-5-yl)butyric acid (35 mg) as a pale yellow solid, m.p. 232°–235° C.

NMR Spectrum: (CD$_3$SOCD$_3$) 2.04, 2.25, 2.44 (3×m, 4H, 3-CH$_2$ and cyclopenta[g]quinazoline 7-CH$_2$), 2.33, 2.66 (2×s, 6H, cyclopenta[g]quinazoline 2-CH$_3$ and N-CH$_3$), 2.92–3.20 (m, 4H, 4-CH$_2$ and cyclopenta[g]quinazoline 8-CH$_2$), 4.51 (m, 1H, 2-CH), 5.33 (s, 2H, C$\underline{H}_2$CO$_2$CH$_3$), 5.79 (t, J=8.5 Hz, 1H, cyclopenta[g]quinazoline 6-CH), 6.80 (d, J=15.9 Hz, 1H, 3'-ArH), 6.85 (d, J=8.7 Hz, 1H, 5'-ArH), 7.48 (s, 1H, cyclopenta[g]quinazoline 9-H), 7.62 (t, J=9.1 Hz, 1H, 6'-ArH), 7.67 (s, 1H, cyclopenta[g]quinazoline 5-H), 8.08 (t, J=7.0 Hz, 1H, CONH), 12.15 (s, 1H, lactam NH).

Mass Spectrum: (ESI) m/e 579 [(M+H)$^+$].

Elemental Analysis: Found C, 54.81; H, 4.86; N, 18.94; C$_{27}$H$_{27}$FN$_8$O$_6$ 0.75 H$_2$O requires: C, 54.77; H, 4.81, N, 18.92%.

Example 12

(2RS)-2-{N-{N-{o-Fluoro-p-[N-methyl-N-((6RS)-2-methyl-4-oxo-3,4,7,8-tetrahydro-6H-cyclopenta[g]quinazolin-6-yl)amino]benzoyl}-L-γ-glutamyl}-amino}-2-[p-(carboxymethyl)phenyl]acetic acid (1) Methyl (2RS)-2-{N-[α-benzyl-N-(tert-butoxycarbonyl)-L-γ-glutamyl]amino}-2-[p-(methoxycarbonylmethyl) phenyl]acetate To a solution of α-benzyl N-(tert-butoxycarbonyl)-L-glutamate (1.35 g, 4 mmol) and methyl α-amino-p-methoxycarbonylmethylphenyl- acetate (1.1 g, 4 mmol), prepared as described in section (7) of Example 8, in 20 ml of CHCl$_3$ was added 1-ethoxycarbonyl-2-ethoxy-1,2-dihydroquinoline (EEDQ) (1.1 g, 4.4 mmol) and N-methylmorpholine (0.44 g, 4.4 mmol). The reaction mixture was stirred for 48 hours at 4° C. The organic layers were then washed in turn with 2N HCl, saturated NaHCO$_3$, water and brine, then dried (MgSO$_4$). After evaporation of the solvent the resulting oil was crystallized from petroleum ether to give methyl (2RS)-2-{N-[α-benzyl-N-(tert-butoxycarbonyl)-L-γ-glutamyl]amino}-2-[p-(methoxycarbonylmethyl)-phenyl]acetate (1.45 g, 65%) as a white solid.

NMR Spectrum: (DMSO Acetic acid) 1.4 (s, 9H), 1.7–1.85 (m, 1H), 1.9–2.05 (m, 1H), 2.3 (m, 2H), 3.6 (s, 6H), 3.7 (s, 2H), 4.0–4.1 (m, 1H), 5.1 (q, 2H), 5.4 (m, 1H), 7.25 (d, 2H), 7.3–7.4 (m, 7H).

(2) Methyl (2RS)-2-[N-(α-benzyl-L-γ-glutamyl) amino]-2-[p-(methoxycarbonyl-methyl)phenyl]acetate To a solution of methyl (2RS)-2-{N-[α-benzyl-N-(tert-butoxycarbonyl)-L-γ-glutamyl]amino}-2-[p-(methoxycarbonylmethyl)phenyl]acetate (1.35 g, 2.4 mmol) in 5 ml of dichloromethane was added 5 ml of TFA and 0.5 ml of water. After stirring for 1 hour at room temperature the solution was evaporated to dryness and the resulting solid was azeotroped with toluene to give methyl (2RS)-2-[N-(α-benzyl-L-γ-glutamyl)-amino]-2-[p-(methoxycarbonylmethyl)phenyl]acetate (1.4 g) as a gummy solid;

NMR Spectrum: (DMSO/TFA) 1.95–2.15 (m, 2H), 2.35–1.55 (m, 2H), 3.6 (s, 6H), 3.7 (s, 2H), 4.15 (m, 1H), 5.15–5.3 (m, 2H), 5.4 (m, 1H), 7.25–7.45 (m, 9H).

Mass Spectrum: (ESI) 457 [(M+H)$^+$].

(3) Methyl (2RS)-2-{N-{N-{o-fluoro-p-[N-methyl-N-((6RS)-2-methyl-4-oxo-3-pivaloyloxymethyl-3,4,7,8-tetrahydro-6H-cyclopenta[g]quinazolin-6-yl) amino]-benzoyl}-α-benzyl-L-γ-glutamyl}amino}-2-[p-(methoxycarbonylmethyl)phenyl]-acetate A mixture of pentafluorophenyl o-fluoro-p-[N-methyl-N-((6RS)-2-methyl-4-oxo-3-pivaloyloxymethyl-3,4,7,8-tetrahydro-6H-cyclopent-[g]quinazolin-6-yl)amino]-benzoate (0.093 g, 0.144 mmol), prepared as described in Example 2, methyl (2RS)-2-[N-(α-benzyl-L-γ-glutamyl) amino]-2-[p-(methoxycarbonylmethyl)phenyl]acetate, trifluoroacetic acid salt (0.106 g, 0.186 mmol), triethylamine (0.026 g, 0.26 mmol), N-hydroxybenzotriazole (0.002 g), and dry DMF (1 ml) was stirred under nitrogen at ambient temperature for 17 hours. The resulting solution was evaporated and the residue partitioned between ethyl acetate (20 ml) and saturated aqueous sodium hydrogen carbonate (15 ml). The aqueous layer was extracted with ethyl acetate (3×5 ml) and the combined ethyl acetate solution washed with water (5×5 ml), dried over magnesium sulphate, and evaporated. The residue was twice redissolved in toluene and evaporated, then purified by silica gel column chromatography using a gradient of ethyl acetate in dichloromethane (0 to 40% ethyl acetate) as eluant. The product was triturated with hexane and the resulting white solid isolated by decanting off the hexane, and dried in vacuo. There was thus obtained methyl (2RS)-2-{N-{N-{o-fluoro-p-[N-methyl-N-((6RS)-2-methyl-4-oxo-3-pivaloyloxymethyl-3,4,7,8-tetrahydro-6H-cyclopenta[g]quinazolin-6-yl)amino]benzoyl}-α-benzyl-L-γ-glutamyl}-amino}-2-[p-(methoxycarbonylmethyl)phenyl]acetate (0.078 g, 59%), m.p. 85°–90° C.;

NMR Spectrum: (CD$_3$SOCD$_3$) 1.13 (s, 9H, C(CH$_3$)$_3$), 2.05 (m, 3H, glu β-CH$_2$ and cyclopenta[g]quinazoline 7-H), 2.34 (m, 2H, glu γ-CH$_2$), 2.45 (m, 1H, partly obscured, cyclopenta[g]quinazoline 7-H), 2.59 (s, 3H, cyclopenta[g]quinazoline 2-CH$_3$), 2.66 (s, 3H, N-CH$_3$), 3.07 (m, 2H, cyclopenta[g]quinazoline 8-H), 3.60 (2×s, 6H, 2×COOCH$_3$), 3.67 (s, 2H, —C$_6$H$_4$CH$_2$), 4.48 (m, H, glu α-CH), 5.15 (s, 2H, PhCH$_2$), 5.37 (d, J 6.9 Hz, 1H, α'-CH), 5.81 (t, J 8.2 Hz, 1H, cyclopenta[g]quinazoline 6-H), 6.04 (m, 2H, cyclopenta[g]quinazoline N3-CH$_2$), 6.84 (m, 2H, 3',5'-ArH), 7.30 (m, 9H, C$_6$H$_5$—and —C$_6$H$_4$—), 7.53 (s, 1H, cyclopenta[g]quinazoline 9-H), 7.60 (t, J 9.0 Hz, 1H, 6'-ArH), 7.71 (s, 1H, cyclopenta[g]quinazoline 5-H), 8.13 (m, 1H, glu NH), 8.76 (d, J 6.8 Hz, 1H, α'-NH).

Mass Spectrum: (ESI) m/e 920 [(M+H)$^+$].

Elemental Analysis: Found C, 65.09; H, 6.06; N, 7.38% C$_{50}$H$_{54}$FN$_5$O$_{11}$ requires C, 65.28; H, 5.92; N, 7.61%.

(4) (2RS)-2-{N-{N-{o-Fluoro-p-[N-methyl-N-((6RS)-2-methyl-4-oxo-3,4,7,8-tetrahydro-6H-cyclopenta[g]quinazolin-6-yl)amino]benzoyl}-L-γ-glutamyl}amino}-2-[p-(carboxymethyl)phenyl]acetic acid Aqueous sodium hydroxide solution (1N, 0.72 ml) was added to a solution of methyl (2RS)-2-{N-{N-{o-fluoro-p-[N-methyl-N-((6RS)-2-methyl-4-oxo-3-pivaloyl-oxymethyl-3,4,7,8-tetrahydro-6H-cyclopenta[g]quinazolin-6-yl)amino]benzoyl}-α-benzyl-L-γ-glutamyl}amino}-2-[p-(methoxycarbonylmethyl)phenyl]acetate (0.066 g, 0.072 mmol) in methanol (3 ml) and the resulting solution was stirred at ambient temperature under argon in the dark for 24 hours. The solution was diluted with water (12 ml), filtered, and concentrated by evaporation to a volume of approximately 7 ml. Further water (3 ml) was added and the solution was acidified to pH 3–4 by dropwise addition of 1N aqueous hydrochloric acid with stirring. The resulting suspension was centrifuged and the supernatant removed. The precipitate was washed 3 times with water by resuspension, centrifugation, and removal of the supernatant, then dried in vacuo triturated with diethyl ether and further dried at 70°–80° C. for 6 hours. There was thus obtained (2RS)-2-{N-{N-{o-fluoro-p-[N-methyl-N-((6RS)-2-methyl-4-oxo-3,4,7,8-tetrahydro-6H-cyclopenta[g]quinazolin-6-yl) amino]benzoyl}-L-γ-glutamyl}amino}-2-[p-(carboxymethyl) phenyl]acetic acid (0.037 g, 72%), m.p. 175°–177° C.;

NMR Spectrum: (CD$_3$SOCD$_3$) 2.01 (m, 3H, glu β-CH$_2$ and cyclopenta[g]quinazoline 7-H), 2.20–2.60 (m, 6H, partly obscured, glu γ-CH$_2$, cyclopenta[g]quinazoline 2-CH$_3$ and cyclopenta[g]quinazoline 7-H), 2.66 (s, 3H, N—CH$_3$), 3.08 (m, 2H, cyclopenta[g]quinazoline 8-H), 3.55 (s, 2H, —C$_6$H$_4$CH$_2$—), 4.37 (m, 1H, glu α-CH), 5.27 (d, J 7.3 Hz, 1H, α'-CH), 5.79 (t, J 8.1 Hz, 1H, cyclopenta[g] quinazoline 6-H), 6.82 (m, 2H, 3',5'-ArH), 7.27 (m, 4H, —C$_6$H$_4$—), 7.48 (s, 1H, cyclopenta[g]quinazoline 9-H), 7.63 (m, 2H, 6'-ArH and cyclopenta[g]quinazoline 5-H), 7.90 (m, 1H, glu NH), 8.63 (m, 1H, α'-NH), 12.17 (s, 1H, cyclopenta[g]quinazoline N3-H).

Mass Spectrum: (ESI) m/e 688 [(M+H)$^+$].

Elemental Analysis: Found C, 58.89; H, 5.25; N, 9.03% C$_{35}$H$_{34}$FN$_5$O$_9$ 1.8 H$_2$O requires C, 58.38; H, 5.26; N, 9.73%.

Example 13

N-{p-[N-((6RS)-2-Methyl-4-oxo-3,4,7,8-tetrahydro-6 H-cyclopenta[g]-quinazolin-6-yl)-N-(prop-2-ynyl) amino]benzoyl }-L-γ-glutamyl-N-methyl-L-glutamic acid (1) 2-Methyl-3-pivaloyloxymethyl-3,4,7,8-tetrahydro-6 H-cyclopenta[g]quinazolin-4,6-dione 70% tert-Butyl hydroperoxide solution (111 ml, 0.81 mol) was added during 3 minutes to a stirred suspension of chromium (VI) oxide (0.59 g, 5.9 mmol) in dichloromethane (232 ml) in a flask fitted with a reflux condenser, whilst cooling the mixture in a bath of water at room temperature. 2-Methyl-3-pivaloyloxymethyl-3,4,7,8-tetrahydro-6 H-cyclopenta[g]quinazolin-4-one (36.586 g, 0.116 mol), prepared as described in Example 1(5), was added in portions during 2 minutes and the mixture was stirred at ambient temperature for 16 hours. It was then cooled to 0° C. and 10% aqueous sodium metabisulphite solution (195 ml) was added at such a rate that the temperature did not exceed 10° C. The resulting mixture was allowed to warm to room temperature and stirred for 2½ hours. It was then partitioned between ethyl acetate (400 ml) and half-saturated brine (300 ml). The aqueous layer was extracted with ethyl acetate (2×150 ml) and the combined organic solution was washed successively with saturated aqueous sodium hydrogen carbonate (300 ml), saturated brine (2×150 ml), saturated aqueous sodium hydrogen carbonate (150 ml) and saturated brine (150 ml), then dried (MgSO$_4$), treated with charcoal powder and evaporated to dryness. A portion of ethyl acetate was added and evaporated and the residue was crystallised from hexane-ethyl acetate to give 2-methyl-3-pivaloyloxymethyl-3,4,7,8-tetrahydro-6H-cyclopenta[g]-quinazolin-4,6-dione (10.371 g, 27%), m.p. 203°–205° C.

NMR Spectrum: (CD$_3$SOCD$_3$) 1.15 (s, 9H, C(CH$_3$)$_3$), 2.64 (s, 3H, 2-CH$_3$), 2.72 (m, 2H, 7-CH$_2$), 3.24 (m, 2H, 8-CH$_2$), 6.06 (s, 2H, N3-CH$_2$), 7.22 (s, 1H, 9-CH), 8.27 (s, 1H, 5-H).

Mass Spectrum: (EI) m/e 328 (25%, M+), 243 (5%), 227 (56%), 214 (77%).

IR Spectrum: (KBr disc) v$_{max}$ 1612, 1684, 1711, 1729 cm$^{-1}$.

Elemental Analysis: Found C, 65.71; H, 6.17; N, 8.54% C$_{18}$H$_{20}$N$_2$O$_4$ requires C, 65.84; H, 6.14; N, 8.53%.

(2) Diethyl N-{p-[N-((6RS)-2-methyl-4-oxo-3-pivaloyloxymethyl-3,4,7,8-tetrahydro-6 H-cyclopenta[g]quinazolin-6-yl)amino]benzoyl }-L-glutamate A reaction flask was charged with 2-methyl-3-pivaloyloxymethyl-3,4,7,8-tetrahydro-6H-cyclopenta[g] quinazolin-4,6-dione (3.332 g, 10.15 mmol), diethyl p-aminobenzoyl-L-glutamate (6.54 g, 20.3 mmol), prepared as described in the Journal of Medicinal Chemistry, 1985, 28, 1428, p-toluenesulphonic acid monohydrate (0.12 g, 0.6 mmol), and dry 1,2-dimethoxyethane (100 ml), and fitted with a pressure equalising dropping funnel containing activated 3A molecular sieve beads (4–8 mesh; 41 g). A reflux condenser was fitted to the top of the dropping funnel and the mixture was stirred and heated under reflux under nitrogen for 4 hours. The apparatus enabled solvent vapour to pass up the side tube of the dropping funnel and condense in the reflux condenser, and the condensed solvent to percolate through the molecular sieves before returning to the reaction flask. The mixture was cooled to ambient temperature and a solution of sodium cyanoborohydride (1.0 g, 15.9 mmol) in methanol (18 ml) was added, followed immediately by acetic acid (1.0 ml). The mixture was stirred at ambient temperature for 18 hours and concentrated. The residue was partitioned between saturated aqueous sodium hydrogen carbonate (150 ml) and ethyl acetate (150 ml). The aqueous layer was extracted with ethyl acetate (3×25 ml) and the combined organic solution washed with brine (5×25 ml), dried (MgSO$_4$) and concentrated to dryness. The residue was fractionated by chromatography with increasingly polar mixtures of dichloromethane and ethanol (ratio 100:0 to 100:4 v/v) as eluant. The appropriate fractions were combined and evaporated and the residue triturated with diethyl ether to give diethyl N-{p-[N-((6RS)-2-methyl-4-oxo-3-pivaloyloxymethyl-3,4,7,8-tetrahydro-6 H-cyclopenta[g]quinazolin-6-yl)amino]-benzoyl}-L-glutamate (2.847 g, 44%), m.p. 171° C.

NMR Spectrum: (CD$_3$SOCD$_3$) 1.12 (s, 9H, C(CH$_3$)$_3$), 1.18 (m, 6H, 2×CH$_2$CH$_3$), 2.0 (m, 3H, glu β-CH$_2$ and cyclopenta[g]quinazoline 7-H), 2.43 (t, 2H, glu γ-CH$_2$), 2.60 (m, 4H, cyclopenta[g]quinazoline 2-CH$_3$ and 7-H) 3.00 (m, 1H, cyclopenta[g]quinazoline 8-H), 3.08 (m, 1H, cyclopenta[g]quinazoline 8-H), 4.06 (m, 4H, 2×CH$_2$CH$_3$), 4.39 (m, 1H, glu α-CH), 5.18 (q, 1H, cyclopenta[g]quinazoline 6-H), 6.04 (m, 2H, cyclopenta[g]quinazoline N3-CH$_2$), 6.72 (d, J 8.2 Hz, 1H, cyclopenta[g]quinazoline C6-NH), 6.79 (d, J 8.8 Hz, 2H, 3',5'-ArH), 7.50 (s, 1H, cyclopenta[g]quinazoline 9-H), 7.71 (d, J 8.7 Hz, 2H, 2',6'-ArH), 7.94 (s, 1H, cyclopenta[g]quinazoline 5-H), 8.30 (d, J 7.4 Hz, 1H, glu NH).

Mass Spectrum: (FAB) m/e 657 [100%, (M+Na)$^+$], 635 [8%, (M+H)$^+$], 432 (24%), 313 (20%), 199 (18%).

Elemental Analysis; Found C, 64.29; H, 6.65; N, 8.81% C$_{34}$H$_{42}$N$_4$O$_8$ requires C, 64.34; H, 6.67; N, 8.83%.

(3) Diethyl N-{p-[N-((6RS)-2-methyl-4-oxo-3-pivaloyloxymethyl-3,4,7,8-tetrahydro-6H-cyclopenta[g]quinazolin-6-yl)-N-(prop-2-ynyl)amino]benzoyl}-L-glutamate Diethyl N-{p-[N-((6RS)-2-methyl-4-oxo-3-pivaloyloxymethyl-3,4,7,8-tetrahydro-6 H-cyclopenta[g]quinazolin-6-yl)amino]benzoyl}-L-glutamate was converted to diethyl N-{p-[N-{p-((6RS)-2-methyl-4-oxo-3-pivaloyloxymethyl-3,4,7,8-tetrahydro-6 H-cyclopenta[g]quinazolin-6-yl)-N-(prop-2-ynyl)amino] benzoyl}-L-glutamate by the procedure described in Example 4(2).

(4) N-{p-[N-((6RS)-2-Methyl-4-oxo-3,4,7,8-tetrahydro-6H-cyclopenta[g]quinazolin-6-yl)-N-(prop-2-ynyl)amino] benzoyl}-L-glutamic acid Diethyl N-{p-[N-((6RS)-2-methyl-4-oxo-3-pivaloyloxymethyl-3,4,7,8-tetrahydro-6 H-cyclopenta[g]quinazolin-6-yl)-N-(prop-2-ynyl)amino] benzoyl}-L-glutamate was converted to N-{p-[N-((6RS)-2-methyl-4-oxo-3,4,7,8-tetrahydro-6 H-cyclopenta[g]quinazolin-6-yl)-N-(prop-2-ynyl)amino] benzoyl}-L-glutamic acid by the procedure described in Example 4(3).

(5) p-[N-((6RS)-2-Methyl-4-oxo-3,4,7,8-tetrahydro-6 H-cyclopenta[g]quinazolin-6-yl)-N-(prop-2-ynyl)amino] benzoic acid N-{p-[N-((6RS)-2-Methyl-4-oxo-3,4,7,8-tetrahydro-6 H-cyclopenta[g]-quinazolin-6-yl)-N-(prop-2-ynyl)amino] benzoyl}-L-glutamic acid was converted to p-[N-((6RS)-2-methyl-4-oxo-3,4,7,8-tetrahydro-6 H-cyclopenta[g]quinazolin-6-yl-N-(prop-2-ynyl)amino] benzoic acid by the procedure described in Example 4(4).

(6) Tri-tert-butyl N-{p-[N-((6RS)-2-methyl-4-oxo-3,4,7,8-tetrahydro-6 H-cyclopenta[g]quinazolin-6-yl)-N-(prop-2-ynyl)amino] benzoyl}-L-γ-glutamyl-N-methyl-L-glutamate Diethyl cyanophosphonate (0.16 g, 0.99 mmol) and triethylamine (0.10 g, 0.99 mmol) were added successively to a stirred mixture of p-[N-((6RS)-2-methyl-4-oxo-3,4,7,8-tetrahydro-6 H-cyclopenta[g]quinazolin-6-yl)-N-(prop-2-ynyl)amino] benzoic acid (0.171 g, 0.448 mmol), tri-tert-butyl L-γ-glutamyl-N-methyl-L-glutamate (0.267 g, 0.582 mmol), prepared as described in Example 1 of UK Patent Application GB 2265148A, and DMF (2.4 ml) at 0° C. After 5 minutes the mixture was allowed to warm to room temperature and stirred in the dark for 5 hours. It was then partitioned between ethyl acetate (30 ml) and water (30 ml). The aqueous layer was extracted with ethyl acetate (4×15 ml) and the combined ethyl acetate solution was washed successively with 10% citric acid solution (2×15 ml), saturated aqueous sodium hydrogen carbonate (30 ml) and half-saturated brine (4×30 ml), dried (MgSO$_4$) and evaporated. The residue was chromatographed using increasingly polar mixtures of dichloromethane and ethanol (100:0 to 95:5 v/v) as eluant and the glass obtained was triturated with hexane to give tri-tert-butyl N-{p-[N-((6RS)-2-methyl-4-oxo-3,4,7,8-tetrahydro-6H-cyclopenta [g]quinazolin-6-yl)-N-(prop-2-ynyl)-amino]benzoyl}-L-γ-glutamyl-N-methyl-L-glutamate (0.238 g, 65%), m.p. 108°–100° C.

NMR Spectrum: (CD$_3$SOCD$_3$) 1.37, 1.38, 1.41 (3×s, 27H, C(CH$_3$)$_3$), 1.87, 2.00, 2.17 (3×m, 7H, glu β-CH$_2$, N-Me-glu β-CH$_2$, N-Me-Glu γ-CH$_2$, cyclopenta[g] quinazoline 7-H), 2.33 (s, 3H, cyclopenta[g]quinazoline 2-CH$_3$), 2.5 (m, 3H, partly obscured by solvent signal, glu γ-CH$_2$, cyclopenta[g]quinazoline 7-H), 2.63, 2.82 (2×s, 3H, N—CH$_3$), 3.02 (m, 1H, cyclopenta[g]quinazoline 8-H), 3.13 (m, 2H, C≡CH, cyclopenta[g]quinazoline 8-H), 3.83 (m, 1H, CH$_2$C≡C), 4.09 (m, 1H, CH$_2$C≡C), 4.30 (m, 1H, glu γ-CH), 4.51, 4.82 (2×m, 1H, N-Me-glu α-CH), 5.76 (t, J 8 Hz, 1H, cyclopenta[g]quinazoline 6-H), 7.01 (d, J 8.8 Hz, 2H, 3',5'-ArH), 7.49 (s, 1H, cyclopenta[g]quinazoline 9-H), 7.80 (m, 3H, 2',6'-ArH), cyclopenta[g]quinazoline 5-H), 8.33 (m, 1H, glu NH), 12.14 (s, 1H, cyclopenta[g] quinazoline N3-H).

Mass Spectrum; (FAB) m/e 836 [5%, (M+Na)$^+$], 814 [10%, (M+H)$^+$], 459 (8%), 356 (100%).

Elemental Analysis: Found C, 66.03; H, 7.30; N, 8.53%. C$_{45}$H$_{59}$N$_5$O$_9$ requires C, 66.40; H, 7.31; N, 8.60%.

(7) N-{p-[N-((6RS)-2-Methyl-4-oxo-3,4,7,8-tetrahydro-6 H-cyclopenta[g]quinazolin-6-yl)-N-(prop-2-ynyl)amino] benzoyl}-L-γ-glutamyl-N-methyl-L-glutamic acid A solution of tri-tert-butyl N-{p-[N-((6RS)-2-methyl-4-oxo-3,4,7,8-tetrahydro-6 H-cyclopenta[g]quinazolin-6-yl)-N-(prop-2-ynyl)amino] benzoyl}-L-γ-glutamyl-N-methyl-L-glutamate (0.159 g, 0.195 mmol) in trifluoroacetic acid (8.4 ml) was stirred at ambient temperature in the dark for 75 minutes, then evaporated. The residual glass was triturated with diethyl ether, dried and dissolved in 0.5 M aqueous sodium hydrogen carbonate (3 ml). The solution was filtered, and acidified to pH 4 with 1 M hydrochloric acid whilst cooling in ice. The resulting suspension was centrifuged and the precipitate washed 4 times by resuspension in water, centrifugation and removal of the supernatant, then dried. There was thus obtained N-{p-[N-((6RS)-2-methyl-4-oxo-3,4,7,8-tetrahydro-6H-cyclopenta [g]quinazolin-6-yl)-N-(prop-2-ynyl)amino]benzoyl}-L-γ-glutamyl-N-methyl-L-glutamic acid (0.096 g, 73%), m.p. 168° C.

NMR Spectrum: (CD$_3$SOCD$_3$) 1.75–2.3 (m, 7H, glu β-CH$_2$, N-Me-glu β-CH$_2$, N-Me-glu γ-CH$_2$, cyclopenta[g] quinazoline 7-H), 2.33 (s, 3H, cyclopenta[g]quinazoline 2-CH$_3$), 2.5 (m, 3H, partly obscured by solvent signal, glu γ-CH$_2$, cyclopenta[g]quinazoline 7-H), 2.65, 2.82 (2×s, 3H, N—CH$_3$), 3.02 (m, 1H, cyclopenta[g]quinazoline 8-H), 3.14 (m, 2H, C≡CH and cyclopenta[g]quinazoline 8-H), 3.83 (m, 1H, CH$_2$C≡C), 4.09 (m, 1H, CH$_2$C≡C), 4.35 (m, 1H, glu α-CH), 4.57, 4.92 (2×m, 1H, N-Me-glu α-CH), 5.76 (t, J 7.9 Hz, 1H, cyclopenta[g]quinazoline 6-H), 7.01 (d, J 7.8 Hz, 2H, 3',5'-ArH), 7.49 (s, 1H, cyclopenta[g]quinazoline 9-H), 7.8 (m, 3H, 2',6'-ArH, cyclopenta[g]quinazoline 5-H), 8.35 (m, 1H, glu NH), 12.15 (s, 1H, cyclopenta[g] quinazoline N3-H), 12.49 (br. s, 3H, 3×COOH).

Mass Spectrum: (FAB) m/e 646 [13%, (M+H)$^+$], 356 (100%).

Elemental Analysis: Found C, 59.17; H, 5.66; N, 10.42% C$_{33}$H$_{35}$N$_5$O$_9$ 1.5 H$_2$O requires C, 58.92; H, 5.69; N, 10.41%.

Example 14

(2S)-2-{p-[N-((6RS)-2-methyl-4-oxo-3,4,7,8-tetrahydro-6 H-cyclopenta[g]quinazolin-6-yl)-N-(prop-2-ynyl) amino]benzamido}-4-[1-(2-carboxyethyl)tetrazol- 5-yl]butyric acid (1) Dimethyl N-[N-(benzyloxycarbonyl)-L-γ-glutamyl]-β-alaninate To a stirred solution of α-methyl N-(benzyloxycarbonyl)-L-glutamate (1.33 g, 4.54 mmol) in dry tetrahydrofuran (12 ml) and N-methylmorpholine (0.454 g, 4.5 mmol) cooled to −20° C. was added isobutyl chloroformate (0.612 g, 4.5 mmol) (a white precipitate had formed). Stirring was continued at −20° C. for 10 minutes and then a suspension of β-alanine methyl ester hydrochloride (0.628 g, 4.5 mmol) in N-methylmorpholine (0.454 g, 4.5 mmol) and dry tetrahydrofuran (8 ml) was added into the reaction mixture which was stirred at −20° C. for 10 minutes and then for 2 hours at room temperature. The N-methylmorpholine hydrochloride was removed by filtration and the filtrate was concentrated in vacuo to a yellow oily residue. Purification by column chromatography on elution with 40% ethyl acetate in dichloromethane gave dimethyl N-[N-(benzyloxycarbonyl)-L-γ-glutamyl]-β-alaninate as colourless viscous oil (1.54 g, 89%);

NMR Spectrum: (CD$_3$SOCD$_3$) 1.75, 1.94 (2×m, 2H, glu β-CH$_2$), 2.13 (t, J=7.4 Hz, 2H, glu 65 -CH$_2$), 2.42 (t, J=6.8 Hz, 2H, NHCH$_2$CH$_2$CO$_2$Me), 3.22 (q, J=6.2 Hz, 2H, NHCH$_2$CH$_2$CO$_2$Me), 3.57, 3.61 (2×s, 6H, 2×CO$_2$Me), 4.02 (m, 1H, glu α-CH), 5.02 (s, 2H, PhCH$_2$), 7.35 (m, 5H, Ph), 7.73 (d, J=7.7 Hz, 1H, glu NH), 7.93 (t, J=5.15 Hz, 1H, CH$_2$CON HCH$_2$)

Mass Spectrum: (CI) m/e 381 [(M+H)$^+$].

Elemental Analysis: Found C, 56.63; H, 6.38; N, 7.16; C$_{18}$H$_{24}$N$_2$O$_7$ requires C, 56.83; H, 6.36; N, 7.36%.

(2) Methyl (2S)-2-(benzyloxycarbonylamino)-4-[1-(2-methoxycarbonylethyl)-tetrazol-5-yl]butyrate To a stirred solution of phosphorous pentachloride (1.29 g, 6.2 mmol) in chloroform (15 ml) was added quinoline (1.60 g, 12.4 mmol) (a pale yellow precipitate had formed). The reaction mixture was stirred at room temperature for 20 minutes under nitrogen and then a solution of dimethyl N-[N-(benzyloxycarbonyl)-L-γ-glutamyl]-β-alaninate (2.36 g, 6.2 mmol) in chloroform (12 ml) was added dropwise into the reaction mixture while the temperature was maintained below 20° C. (a clear solution had obtained). Stirring was continued at temperature lower than 25° C. for 25 minutes and then a solution of hydrazoic acid in benzene (prepared as described in Fieser and Fieser, Reagents for Organic Synthesis, Vol. 1, John Wiley and Sons, New York, 1967, p 446; 18 ml) was added into the reaction mixture and the resulting orange solution was stirred at room temperature for 2¼ hours before being evaporated. The residue was partitioned between ethyl acetate (180 ml) and water (180 ml). The two layers were separated and the organic layer was washed with 1N aqueous hydrochloric acid (180 ml), half saturated aqueous sodium bicarbonate (180 ml) and water (200 ml), dried (Na$_2$SO$_4$) and concentrated in vacuo to an oily residue. Purification by column chromatography, on elution with v/v 1:1 ethyl acetate/hexanes gave methyl (2S)-2-(benzyloxycarbonylamino)-4-[1-(2-methoxycarbonylethyl)-tetrazol-5-yl]butyrate as a colourless viscous oil (0.55 g, 22%) that solidified on standing at −20° C. for a few weeks, m.p. 80°–81° C.

NMR Spectrum: (CD$_3$SOCD$_3$) 2.00–2.25 (m, 2H, CHC H$_2$CH$_2$), 2.99 (m, 4H, CHCH$_2$CH$_2$ and NCH$_2$C H$_2$CO$_2$Me), 3.58, 3.64 (2×s, 6H, 2×CO$_2$Me), 4.23 (m, 1H, CHCH$_2$CH$_2$), 4.49 (t, J=6.5 Hz, 2H, NCH$_2$CH$_2$CO$_2$Me), 5.05 (s, 2H, PhCH$_2$), 7.36 (m, 5H, Ph), 7.92 (d, J=7.9 Hz, 1H, CONH).

Mass Spectrum: (CI) m/e 406 [(M+H)$^+$].

Elemental Analysis: Found C, 52.95; H, 5.71; N, 17.00; C$_{18}$H$_{23}$N$_5$O$_6$ requires C, 53.33; H, 5.72; N, 17.27%.

(3) Methyl (2S)-2-amino-4-[1-(2-methoxycarbonylethyl) tetrazol-5-yl]butyrate

To a solution of methyl (2S)-2-(benzyloxycarbonylamino)-4-[1-(2-methoxy-carbonylethyl) tetrazol-5-yl]butyrate (0.233 g, 0.575 mmol) in ethyl acetate (25 ml) was added 10% Pd/C. (0.045 g). The resulting black mixture was degassed and then stirred at 24° C. for 4 hours under hydrogen. The catalyst was removed by filtration and the filtrate was concentrated in vacuo to a colourless viscous oil that dried in vacuo over phosphorous pentoxide. There was thus obtained methyl (2S)-2-amino-4-[1-(2-methoxycarbonylethyl)tetrazol-5-yl]butyrate (0.146 g, 94%) as a colourless viscous oil. This was used in the next step without any further purification.

NMR Spectrum: (CD$_3$SOCD$_3$) 1.80, 2.10 (2×m, 2H, CHC H$_2$CH$_2$), 2.99 (m, 4H, CHCH$_2$CH$_2$ and NCH$_2$C H$_2$CO$_2$Me), 3.38 (dd, J=6.3, 11.2 Hz, 1H, CHCH$_2$CH$_2$), 3.59, 3.62 (2×s, 6H, 2×CO$_2$Me), 4.52 (t, J=6.5 Hz, 2H, NC H$_2$CH$_2$CO$_2$Me).

Mass Spectrum: (ESI) m/e 272 [(M+H)$^+$].

(4) Methyl (2S)-2-{p-[N-((6RS)-2-methyl-4-oxo-3,4,7,8-tetrahydro-6H-cyclopenta [g]quinazolin-6-yl)-N-(prop-2-ynyl)amino]benzamido}-4-[1-(2-methoxy-carbonylethyl) tetrazol-5-yl]butyrate To a stirred solution of methyl (2S)-2-amino-4-[1-(2-methoxycarbonylethyl)-tetrazol-5-yl]butyrate (0.135 g, 0.50 mmol) in anhydrous DMF (3.5 ml) cooled to 0° C. was added p-[N-((6RS)-2-methyl-4-oxo-3,4,7,8-tetrahydro-6 H-cyclopenta[g]quinazolin-6-yl)-N-(prop-2-ynyl)amino] benzoic acid (0.171 g, 0.46 mmol), prepared as described in Example 13(5), followed by diethyl phosphorocyanidate (0.164 g, 1.01 mmol) and triethylamine (0.102 g, 1.01 mmol) (a clear solution had obtained after a few seconds). Stirring was continued at 0° C. for 10 minutes, the ice-bath was then removed and the reaction mixture was stirred for a further 2 hours before being partitioned between ethyl acetate (100 ml) and water (80 ml). The two layers were separated and the aqueous layer was extracted with ethyl acetate (2×80 ml). The ethyl acetate extracts were combined and washed with aqueous 10% citric acid (80 ml), saturated aqueous sodium bicarbonate solution (80 ml), dilute brine (80 ml), dried (Na$_2$SO$_4$) and concentrated in vacuo to a glass. This was dissolved in dichloromethane and to this solution silica gel (Merck Art 7734, 1.5 g) was added. The solvent was removed in vacuo and the free running yellow powder was placed on a silica gel column made up in ethyl acetate. The column was eluted with ethyl acetate (~400 ml) and then with 2% methanol in chloroform to give a white foam that reprecipitated from dichloromethane/hexane. There was thus obtained methyl (2S)-2-{p-[N-((6RS)-2-methyl-4-oxo-3,4,7,8-tetrahydro-6H-cyclopenta[g]quinazolin-6-yl)-N-(prop-2-ynyl)amino]benzamido}-4-[1-(2-methoxycarbonylethyl)tetrazol-5-yl]butyrate (0.150 g, 52%) as a white solid, m.p. 125° C. (dec) then melted at 184°–188° C.

NMR Spectrum: (CD$_3$SOCD$_3$) 2.30–2.40 (m, 4H, CHC H$_2$CH$_2$ and cyclopenta[g]quinazoline 7-CH$_2$), 2.33 (s, 3H, cyclopenta[g]quinazoline 2-CH$_3$), 2.90–3.20 (m, 7H, CHCH$_2$CH$_2$, NCH$_2$CH$_2$CO$_2$Me, cyclopenta[g]quinazoline 8-CH$_2$ and C≡CH), 3.57, 3.65 (2×s, 6H, 2×CO$_2$Me), 3.98 (ABq, J=18.5 Hz, 2H, CH$_2$C≡C), 4.51 (t, J=6.6 Hz, 2H, NC H$_2$CH$_2$CO$_2$Me), 4.60 (m(obscured), 1H, CHCH$_2$CH$_2$), 5.77 (t, J=7.9 Hz, 1H, cyclopenta[g]quinazoline 6-H), 7.02 (d, J=8.4 Hz, 2H, 3',5'-ArH), 7.49 (s, 1H, cyclopenta[g] quinazoline 9-H), 7.78 (s, 1H, cyclopenta[g]quinazoline 5-H), 7.81 (d, J=9.0 Hz, 2H, 2',6'-ArH), 8.59 (d, J=7.60 Hz, 1H, CONH), 12.14 (s, 1H, cyclopenta[g]quinazoline N3-H).

Mass Spectrum; (FAB) m/e 627 [(M+H)$^+$].

Elemental Analysis; Found C, 60.54; H, 5.42; N, 17.43; C$_{32}$H$_{34}$N$_8$O$_6$ 0.5 H$_2$O requires C, 60.46; H, 5.55; N, 17.63%.

(5) (2S)-2-{p-[N-((6RS)-2-Methyl-4-oxo-3,4,7,8-tetrahydro-6H-cyclopenta [g]quinazolin-6-yl)-N-(prop-2-ynyl)amino]benzamido}-4-[1-(2-carboxyethyl)tetrazol-5-yl]butyric acid To a stirred suspension of methyl (2S)-2-{p-[N-((6RS)-2-methyl-4-oxo-3,4,7,8-tetrahydro-6 H-cyclopenta[g]quinazolin-6-yl)-N-(prop-2-ynyl)amino] benzamido}-4-[1-(2-methoxycarbonylethyl)tetrazol-5-yl] butyrate (0.110 g, 0.175 mmol) in methanol (2.5 ml) was added 1N aqueous sodium hydroxide (0.7 ml, 0.7 mmol) to give a clear solution. Stirring was continued at room temperature for 4 hours, then more 1N aqueous sodium hydroxide (0.35 ml, 0.35 mmol) was added. The reaction mixture was stirred at room temperature for a further 1 hour then diluted with water (6 ml) and acidified to pH 3.5 with 1N hydrochloric acid. The white precipitate was collected by filtration, washed with water (5 ml) and dried in vacuo over phosphorous pentoxide. There was thus obtained (2S)-2-{p-[N-((6RS)-2-methyl-4-oxo-3,4,7,8-tetrahydro-6 H-cyclopenta[g]quinazolin-6-yl)-N-(prop-2-ynyl)amino] benzamido}-4-[1-(2-carboxyethyl)tetrazol-5-yl]butyric acid (0.083 g, 80%) as a white solid m.p. 170° C. (dec).

NMR Spectrum: (CD$_3$SOCD$_3$) 2.14–2.30 (m, 4H, CHC H$_2$CH$_2$ and cyclopenta[g]quinazoline 7-CH$_2$), 2.34 (s, 3H, cyclopenta[g]quinazoline 2-CH$_3$), 2.90–3.20 (m, 7H, CHCH$_2$CH$_2$, NCH$_2$CH$_2$CO$_2$Me, cyclopenta[a]quinazoline 8-CH$_2$ and C≡CH), 3.97 (ABq, J=19.1 Hz, 2H, CH$_2$C≡C), 4.47 (t, J=6.6 Hz, 2H, NCH$_2$CH$_2$CO$_2$Me), 4.53 (m(obscured), 1H, CHCH$_2$CH$_2$), 5.77 (t, J=8.07 Hz, 1H, cyclopenta[g]quinazoline 6-H), 7.03 (d, J=8.7 Hz, 2H, 3',5'-ArH), 7.50 (s, 1H, cyclopenta[g]quinazoline 9-H), 7.80 (s, 1H, cyclopenta[g]quinazoline 5-H), 7.82 (d, J=9.0 Hz, 2H, 2', 6'-ArH), 8.47 (d, J=7.7 Hz, 1H, CONH), 12.14 (s, 1H, cyclopenta[g]quinazoline N3-H).

Mass Spectrum: (FAB) m/e 599 [(M+H)$^+$].

Elemental Analysis: Found C, 57.51; H, 5.04; N, 17.94; C$_{30}$H$_{30}$N$_8$O$_6$ 1.5 H$_2$O requires C, 57.59; H, 5.31; N, 17.91%.

Example 15

(2S)-2-{N-{N-{p-[N-((6RS)-2-Methyl-4-oxo-3,4,7, 8-tetrahydro-6 H-cyclopenta[g]quinazolin-6-yl)-N-(prop-2-ynyl) amino]benzoyl}-L-γ-glutamyl}amino}-4-(1-carboxymethyltetrazol-5-yl)butyric acid (1) Methyl (2S)-2-{N-[α-methyl-N-(benzyloxycarbonyl)-L-γ-glutamyl]amino}-4-(1-methoxycarbonylmethyltetrazol-5-yl)butyrate To a stirred solution of α-methyl N-(benzyloxycarbonyl)-L-glutamate (0.295 g, 1.0 mmol) in dry tetrahydrofuran (5 ml) and N-methylmorpholine (0.100 g, 1.0 mmol) cooled to −20° C. was added isobutyl chloroformate (0.137 g, 1.0 mmol) (a white precipitate had formed). Stirring was continued at −20° C. for 10 minutes and then a solution of methyl (2S)-2-amino-4-(1-methoxycarbonylmethyltetrazol-5-yl)butyrate (prepared as described in Example 11(1); 0.260 g, 1.0 mmol) in dry tetrahydrofuran (4 ml) was added into the reaction mixture which was stirred at −20° C. for 10 minutes and then at room temperature for 1½ hours. The N-methylmorpholine hydrochloride was removed by filtration and the filtrate was concentrated in vacuo to a colourless viscous oil. This was twice purified by column chromatography, first on elution with 1% methanol in ethyl acetate and then on elution with 30% dichloromethane in ethyl acetate. There was thus obtained methyl (2S)-2-{N-[α-methyl-N-(benzyloxycarbonyl)-L-γ-glutamyl]amino }-4-(1-methoxy-carbonylmethyltetrazol-5-yl)butyrate as a viscous oil (0.467 g, 87%) which solidified on standing at −20° C. for a few weeks, m.p. 64°–65° C.;

NMR Spectrum: (CD$_3$SOCD$_3$) 1.80, 1.90–2.20 (2×m, 4H, 2×CHCH$_2$CH$_2$), 2.24 (t,=7.5 Hz, 2H, CHCH$_2$CH$_2$CONH), 2.87 (t, J=8.0 Hz, 2H, CHCH$_2$CH$_2$), 3.61, 3.62, 3.72 (3×s, 9H, 3×CO$_2$Me), 4.04 (m, 1H, ZHNCHCO$_2$Me), 4.40 (m, 1H, CH$_2$CONHCHCO$_2$Me), 5.01 (s, 2H, PhCH$_2$), 5.50 (s, 2H, NCH$_2$CO$_2$Me), 7.36 (m, 5H, Ph), 7.78 (d, J=7.9 Hz) and 8.36 (d, J=7.6 Hz, 2H, 2×CONH).

Mass Spectrum: (CI) m/e 535 [(M+H)$^+$].

Elemental Analysis: Found C, 51.77; H, 5.70; N, 15.35; C$_{23}$H$_{30}$N$_6$O$_9$ requires C, 51.68; H, 5.66; N, 15.72%.

(2) Methyl (2S)-2-[N-(α-methyl-L-γ-glutamyl) amino]-4-(1-methoxycarbonyl-methyltetrazol-5-yl)butyrate To a solution of methyl (2S)-2-{N-[α-methyl-N-(benzyloxycarbonyl)-L-γ-glutamyl]amino}-4-(1-methoxycarbonylmethyltetrazol-5-yl)butyrate (0.309 g, 0.575 mmol) in ethyl acetate (25 ml) was added 10% Pd/C (0.046 g). The resulting black mixture was degassed and then stirred at room temperature (11° C.) for 7 hours under hydrogen. TLC (20% dichloromethane in ethyl acetate) indicated incomplete reaction. Therefore more catalyst (0.045 g) was added and stirring was continued at 22° C. for 16 hours under a hydrogen atmosphere. The catalyst was then removed by filtration and the filtrate was concentrated in vacuo. There was thus obtained methyl (2S)-2-[N-(α-methyl-L-γ-glutamyl) amino]-4-(1-methoxycarbonyl-methyltetrazol-5-yl)butyrate (0.220 g, 96%) as a viscous oil.

NMR Spectrum: (CD$_3$SOCD$_3$) 1.60, 1.80, 2.10 (3×m, 4H, 2×CHCH$_2$CH$_2$), 2.23 (t J=8.0 Hz, 2H, CHCH$_2$CH$_2$CO), 2.88 (t, J=8.0 Hz, 2H, CHCH$_2$CH$_2$) 3.29 (dd, J=5.2, 8.1 Hz, 1H, H$_2$NCHCO$_2$Me), 3.62, 3.73 (2×s, 9H, 3×CO$_2$Me), 4.38 (m, 1H, CH$_2$CONHCHCO$_2$Me), 5.52 (s, 2H, NC H$_2$CO$_2$Me), 8.37 (d, J=7.6 Hz, 1H, CONH).

Mass Spectrum: (ESI) m/e 401 [(M+H)$^+$].

(3) Methyl (2S)-2-{N-{N-{p-[N-((6RS)-2-methyl-4-oxo-3, 4,7,8-tetrahydro-6H-cyclopenta [g]quinazolin-6-yl)-N-(prop-2-ynyl)amino]benzoyl}-α-methyl-L-γ-glutamyl}amino}-4-(1-methoxycarbonylmethyltetrazol-5-yl)butyrate To a stirred solution of methyl (2S)-2-[N-(α-methyl-L-γ-glutamyl) amino]-4-(1-methoxycarbonylmethyltetrazol-5-yl)butyrate (0.220 g, 0.575 mmol) in anhydrous DMF (3.5 ml) cooled to 0° C. under nitrogen was added p-[N-((6RS) -2-methyl-4-oxo-3,4,7,8-tetrahydro-6 H-cyclopenta[g]quinazolin-6-yl)-N-(prop-2-ynyl)amino] benzoic acid (0.171 g, 0.46 mmol), prepared as described in Example 13(5), followed by diethyl phosphorocyanidate (0.164 g, 1.01 mmol) and triethylamine (0.102 g, 1.01 mmol) to give a clear solution after about 1 minute. The reaction mixture was stirred at 0° C. for 10 minutes, the ice-bath was then removed and stirring was continued for 2½ hours under nitrogen before being partitioned between ethyl acetate (80 ml) and water (80 ml). The two layers were separated and the aqueous layer was washed with ethyl acetate (2×80 ml). The organics were combined and successively washed with 10% aqueous citric acid (80 ml), saturated aqueous sodium bicarbonate (80 ml) and dilute brine (80 ml), dried ($Na_2SO_4$) and concentrated in vacuo to a yellow glass. This was dissolved in dichloromethane-methanol and to this solution silica gel (Merck Art 7734, 1.2 g) was added. The solvents were removed in vacuo to give a free running powder which was placed on a silica gel column made up in ethyl acetate. Elution of the column with ethyl acetate (~100 ml) and then with a gradient of methanol in chloroform (2 to 3%) afforded a pale yellow solid which reprecipitated from dichloromethane (10 ml)-methanol (2 ml)/hexanes to give the title compound as a white solid (0.143 g). Because of the low yield, the initial aqueous washing and the citric acid washings, obtained during the work-up, were combined and then extracted with ethyl acetate (2×150 ml), dried ($Na_2SO_4$) and concentrated in vacuo to give methyl (2S)-2-{N-{N-{p[N-((6RS)-2-methyl-4-oxo-3,4,7,8-tetrahydro-6 H-cyclopenta[g]quinazolin-6-yl)-N-(prop-2-ynyl)-amino] benzoyl}-α-methyl-L-γ-glutamyl}amino}-4-(1-methoxycarbonylmethyltetrazol-5-yl)butyrate as a white solid. Purification as described above afforded an additional 0.060 g of the product, m.p. 197°-200° C.;

NMR Spectrum: ($CD_3SOCD_3$) 1.83–2.30 (m, 8H, 2×CHC$\underline{H}_2$CH$_2$, CHCH$_2$C$\underline{H}_2$CONH and cyclopenta[g] quinazoline 7-CH$_2$), 2.33 (s, 3H, cycopeta[g]quinazoline 2-CH$_3$), 2.88 (t, J=7.9 Hz, 2H, CHCH$_2$C$\underline{H}_2$), 2.94–3.24 (m, 3H, cyclopenta[g]quinazoline 8-CH$_2$ and C≡CH), 3.61, 3.64, 3.72 (3×s, 9H, 3×CO$_2$Me), 3.96 (ABq, J=19.8 Hz, 2H, CH$_2$C≡C), 4.40 (m, 2H, 2×C$\underline{H}$CH$_2$CH$_2$), 5.52 (s, 2H, N—C$\underline{H}_2$CO$_2$Me), 5.76 (t, J=7.9 Hz, 1H, cyclopenta[g] quinazoline 6-H), 7.00 (d, J=9.0 Hz, 2H, 3', 5'-ArH), 7.49 (s, 1H, cyclopenta[g]quinazoline 9-H), 7.77 (s, 1H, cyclopenta] g]quinazoline 5-H), 7.79 (d, J=8.9 Hz, 2H, 2',6'-ArH), 8.40 (d, J=7.6 Hz) and 8.49 (d, J=7.5 Hz, 2H, 2×CONH), 12.13 (s, 1H, cyclopenta[g]quinazoline N3-H).

Mass Spectrum: (FAB) m/e 756 [(M+H)$^+$].

Elemental Analysis: Found C, 57.61; H, 5.37; N, 16.21; $C_{37}H_{41}N_9O_9$ 0.8 $H_2O$ requires C, 57.70; H, 5.57; N, 16.37%

(4) (2S)-2-{N-{N-{p-[N-((6RS)-2-Methyl-4-oxo-3,4,7,8-tetrahydro-6H-cyclopenta [g]quinazolin-6-yl)-N-(prop-2-ynyl)amino]benzoyl}-L-γ-glutamyl}amino}-4-(1-carboxymethyltetrazol-5-yl)butyric acid To a stirred suspension of methyl (2S)-2-{N-{N-{p-[N-((6RS)-2-methyl-4-oxo-3,4,7,8-tetrahydro-6 H-cyclopenta[g]quinazolin-6-yl)-N-(prop-2-ynyl)amino] benzoyl}-α-methyl-L-γ-glutamyl}amino}-4-(1-methoxycarbonylmethyltetrazol-5-yl)butyrate (0.120 g, 0.16 mmol) in methanol (3.2 ml) was slowly added 1N aqueous sodium hydroxide (0.96 ml, 0.96 mmol) (a clear solution had formed). Stirring was continued at room temperature for 4 hours then more 1N aqueous sodium hydroxide (0.48 ml, 0.48 mmol) was added and the reaction mixture was stirred at room temperature for a further 1 hour. The solution was diluted with water (4 ml), acidified to pH 3.5 with 1N HCl and the precipitated white solid was collected by filtration, washed with water (5 ml) and dried in vacuo over phosphorous pentoxide. There was thus obtained (2S) -2-{N-{N-{p-[N-((6RS)-2-methyl-4-oxo-3,4,7,8-tetrahydro-6 H-cyclopenta[g]quinazolin-6-yl)-N-(prop-2-ynyl)amino] benzoyl}-L-γ-glutamyl}amino}-4-(1-carboxymethyltetrazol-5-yl)butyric acid as a white solid (0.090 g, 79%), m.p. 176° C. (dec);

NMR Spectrum: ($CD_3SOCD_3$) 1.80–2.27 (m, 8H, 2×CHC$\underline{H}_2$CH$_2$, CHCH$_2$C$\underline{H}_2$CONH and cyclopenta[g] quinazoline 7-CH$_2$), 2.34 (s, 3H, cyclopenta[g]quinazoline 2-CH$_3$), 2.87 (t, J=7.8 Hz, 2H, CHCH$_2$C$\underline{H}_2$), 2.94–3.20 (m, 3H, cyclopenta[g ]quinazoline 8-CH$_2$ and CH≡C$\underline{H}$), 3.96 (ABq, J=18.3 Hz, 2H, CH$_2$C≡C), 4.35 (m, 2H, 2×C $\underline{H}$CH$_2$CH$_2$), 5.35 (s, 2H, N—C$\underline{H}_2$CO$_2$Me), 5.75 (t, J=7.6 Hz, 1H, cyclopenta[g]quinazoline 6-H), 7.01 (d, J=8.8 Hz, 2H, 3',5'-ArH), 7.49 (s, 1H, cyclopenta[g]quinazoline 9-H), 7.80 (s, 1H, cyclopenta[g]quinazoline 5-H), 7.82 (d, J=6.8 Hz, 2H, 2',6'-ArH), 8.24 (d, J=7.8 Hz) and 8.34 (d, J=7.7 Hz, 2H, 2×CONH), 12.09 (s, 1H, cyclopenta[g]quinazoline N3-H).

Mass Spectrum: (FAB) m/e 714 [(M+H)$^+$].

Elemental Analysis: Found C, 54.97; H, 5.09; N, 16.85; $C_{34}H_{35}N_9O_9$ 1.5 $H_2O$ requires C, 55.13; H, 5.17; N, 17.01%.

Example 16

(2S)-2-{p-[N-((6RS)-2-methyl-4-oxo-3,4,7,8-tetrahydro-6 H-cyclopenta[g[quinazolin-6-yl)-N-(prop-2-ynyl) amino]benzamido}-4-{1-[N-((1R)-1-carboxyethyl) carbamoylmethyl]tetrazol-5-yl}butyric acid (1) Methyl (2R)-2-[N-(bromoacetyl)amino]propanoate To a stirred solution of bromoacetic acid (1.00 g, 7.2 mmol) in anhydrous THF (10 ml) cooled to –10° C. and under argon was added N-methylmorpholine (0.72 g, 7.2 mmol) followed by isobutyl chloroformate (0.98 g, 7.2 mmol) when a white precipitate formed. Stirring was continued at –10° C. for 7 minutes and then a slurry of D-alanine hydrochloride methyl ester (1.00 g, 7.2 mmol) in anhydrous THF (12 ml) and N-methylmorpholine (0.720 g, 7.2 mmol) was added into the reaction mixture. Stirring was continued at –10° C. for 10 minutes, then the dry ice/acetone bath was removed and the reaction mixture was allowed to stir for a further 15 minutes. The N-methymorpholine hydrochloride was removed by filtration, the filtrate was concentrated in vacuo to give a pale yellow oil. Purification by column chromatography, on elution with 40% ethyl acetate in hexanes, afforded a colourless oil which solidified on standing at room temperature. There was thus obtained methyl (2R)-2-[N-(bromoacetyl)amino]propanoate as a white solid (1.0 g, 63%), m.p. 51°–52° C.

NMR Spectrum: ($CD_3SOCD_3$) 1.28 (d, J=7.3 Hz, 3H, CHC$\underline{H}_3$), 3.63 (s, 3H, OCH$_3$), 3.88 (s, 2H, BrCH$_2$), 4.27 (m, 1H, C$\underline{H}$CH$_3$), 8.76 (d, J=6.9 Hz, 1H, CONH).

Mass Spectrum: (FAB) m/e 224, 226 [(M+H)$^+$].

Elemental Analysis: Found C, 32.47; H, 4.47; N, 6.22; $C_6H_{10}BrNO_3$ requires C, 32.16; H, 4.50; N, 6.25%.

(2) Methyl (2S)-2-[N-(benzyloxycarbonyl)amino]-4-{1-[N-((1R)-1-(methoxycarbonyl)ethyl)carbamoylmethyl]tetrazol-4-yl}butyrate To a stirred solution of methyl (2R)-2-[N-(bromoacetyl)amino]propanoate (0.270 g, 1.2 mmol) in anhydrous dichloromethane (2 ml) was added methyl (2S)-2-(benzyloxycarbonylamino)-4-(tetrazol-5-yl)butyrate (3.19 g, 1.0 mmol), prepared as described in Example 10(2), followed by triethylamine (0.121 g, 1.2 mmol). Stirring was continued at room temperature for 24 hours under argon (a white precipitate was obtained). The reaction mixture was then diluted with ethyl acetate (100 ml) and the white precipitate was filtered off and washed with more ethyl acetate (~15 ml). The filtrate was concentrated in vacuo to an oily residue which was purified by column chromatography using a gradient of ethyl acetate in hexanes (60 to 80%) as eluant. There was thus obtained in order of elution:

(A) methyl (2S)-2[N-(benzyloxycarbonyl)amino]-4-{2-[N-((1 R)-1-(methoxy-carbonyl)ethyl) carbamoylmethyl] tetrazol-5-yl}butyrate as a gum which solidified on standing at room temperature to a white solid (0.105 g, 23%), m.p. 106°–107° C.;

NMR Spectrum: (CD$_3$SOCD$_3$) 1.32 (d, J=7.3 Hz, 3H, CHC$\underline{H}_3$), 1.90–2.20 (m, 2H, CHC$\underline{H}_2$CH$_2$), 2.91 (t, J=6.7 Hz, 2H, CHCH$_2$C$\underline{H}_2$), 3.63 (s, 6H, 2×CO$_2$CH$_3$), 4.16 (m, 1H, ZHNC$\underline{H}$), 4.31 (m, 1H, C$\underline{H}$CH$_3$), 5.04 (s, 2H, PhC$\underline{H}_2$), 5.44 (s, 2H, NC$\underline{H}_2$CONH), 7.36 (m, 5H, Ph), 7.93 (d, J=7.8 Hz, 1H, Z$\underline{H}$NCH), 8.97 (d, J=7.0 Hz, 1H, N$\underline{H}$CHCH$_3$).

Mass Spectrum: (FAB) m/e 463 [(M+H)$^+$].
Elemental Analysis: Found C, 51.92; H, 5.69; N, 18.07; C$_{20}$H$_{26}$N$_6$O$_7$ requires C, 51.94; H, 5.67; N, 18.17%.

(B) methyl (2S)-2-[N-(benzyloxycarbonyl)amino]-4-{1-[N-((1 R)-1-(methoxy-carbonyl)ethyl) carbamoylmethyl] tetrazol-5-yl}butyrate as a gum which solidified on standing at room temperature. This was triturated with dichloromethane/hexanes to give a white solid which collected by filtration (0.242 g, 52%), m.p. 153°–154° C.;

NMR Spectrum: (CD$_3$SOCD$_3$) 1.31 (d, J=7.3 Hz, 3H, CHC$\underline{H}_3$), 1.95–2.20 (m, 2H, CHC$\underline{H}_2$CH$_2$), 2.88 (t, J=6.6 Hz, 2H, CHCH$_2$C$\underline{H}_2$), 3.62, 3.64 (2×s, 6H, 2×CO$_2$CH$_3$), 4.15–4.40 (m, 2H, ZHNC$\underline{H}$and C$\underline{H}$CH$_3$), 5.04 (s, 2H, PhC$\underline{H}_2$), 5.21 (s, 2H, NC$\underline{H}_2$CONH), 7.36 (m, 5H, Ph), 7.90 (d, J=7.9 Hz, 1H, Z$\underline{H}$NCH), 8.99 (d, J=7.0 Hz, 1H, N$\underline{H}$CHCH$_3$).

Mass Spectrum: (FAB) m/e 463 [(M+H)$^+$].
Elemental Analysis: Found C, 51.86; H, 5.66; N, 18.14; C$_{20}$H$_{26}$N$_6$O$_7$ requires C, 51.94; H, 5.67; N, 18.17%.

(3) Methyl (2S)-2-amino-4-{1-[N-((1R)-1-(methoxycarbonyl)ethyl)-carbamoylmethyl]tetrazol-5-yl}butyrate To a stirred solution of methyl (2S)-2-[N-(benzyloxycarbonyl)amino]-4-{1-[N-((1R)-1-(methoxycarbonyl)ethyl)carbamoylmethyl]tetrazol-5-yl}butyrate (0.266 g, 0.575 mmol) in ethyl acetate (25 ml) and ethanol (10 ml) was added 10% Pd/C (0.050 g). The black mixture was degassed and then stirred at 24° C. for 4 hours under hydrogen. The palladium catalyst was removed by filtration, the filtrate was concentrated in vacuo and the residue was dried in vacuo over phosphorous pentoxide. There was thus obtained methyl (2S)-2-amino-4-{1-[N-((1R)-1-(methoxycarbonyl)-ethyl) carbamoylmethyl] tetrazol-5-yl}butyrate as a white solid (0.169 g, 90%), m.p. 87°–89° C.;

NMR Spectrum: (CD$_3$SOCD$_3$) 1.32 (d, J=7.3 Hz, 3H, CHC$\underline{H}_3$), 1.90, 2.02 (2×m, 2H, CHC$\underline{H}_2$CH$_2$), 2.88 (t, J=7.3 Hz, 2H, CHCH$_2$C$\underline{H}_2$), 3.38 (dd(obscured), J=4.8, 8.7 Hz, 1H, H$_2$NC$\underline{H}$), 3.61, 3.63 (2×s, 6H, 2×CO$_2$CH$_3$), 4.30 (m, 1H, C$\underline{H}$CH$_3$), 5.21 (ABq, J=16.7 Hz, 2H, NC$\underline{H}_2$CONH), 8.99 (d, J=7.0 Hz, 1H, N$\underline{H}$CHCH$_3$).

Mass Spectrum: (FAB) m/e 329 [(M+H)$^+$].

(4) Methyl (2S)-2-{p-[N-((6RS)-2-methyl-4-oxo-3,4,7,8-tetrahydro-6H-cyclopenta[g]quinazolin-6-yl)-N-(prop-2-ynyl)amino] benzamido}-4-{1-[N-((1R)-1-(methoxycarbonyl)ethyl) carbamoylmethyl]tetrazol-5-yl}butyrate To a stirred solution of methyl (2S)-2-amino-4-{1-[N-((1R)-1-(methoxycarbonyl)ethyl) carbamoylmethyl] tetrazol-5-yl}butyrate (0.165 g, 0.50 mmol) in anhydrous DMF (3.5 ml) cooled to 0° C. was added p-[N-((6RS)-2-methyl-4-oxo-3,4,7,8-tetrahydro-6H-cyclopenta[g]quinazolin-6-yl)-N-(prop-2-ynyl)amino] benzoic acid (0.171 g, 0.46 mmol), prepared as described in Example 13(5), followed by diethyl phosphorocyanidate (0.164 g, 1.01 mmol) and then triethylamine (0.102 g, 1.01 mmol). The reaction mixture was stirrred at 0° C. for 10 minutes under argon; then the ice-bath was removed and stirring was continued for 2 hours before the reaction mixture being partitioned between ethyl acetate (100 ml) and water (10 ml). The two layers were separated and the aqueous layer was extracted with dichloromethane (80 ml) and ethyl acetate (2×100 ml). The organics were combined and washed with 10% aqueous citric acid (100 ml), saturated aqueous sodium bicarbonate (100 ml), dilute brine (100 ml) and water (100 ml), dried (Na$_2$SO$_4$), and concentrated in vacuo to a yellow glass. This was dissolved in dichloromethane/methanol and to the resulting solution silica gel (Art Merck 7734, 1.5 g) was added. The solvents were removed in vacuo and the yellow free running powder was placed on a silica gel column made up in ethyl acetate. The column was eluted with 2% methanol in ethyl acetate (~300 ml) and then a gradient of methanol in chloroform (1 to 3%). The product, a white solid, was reprecipitated from methanol (2 ml)-dichloromethane (7 ml)/hexanes. There was thus obtained methyl (2S)-2-{p-[N-((6RS)-2-methyl-4-oxo-3,4,7,8-tetrahydro-6H-cyclopenta[g]-quinazolin-6-yl)-N-(prop-2-ynyl)amino] benzamido}-4-{1-{N-((1R)-1-(methoxy-carbonyl)ethyl) carbamoylmethyl]tetrazol-5-yl}butyrate as a white solid (0.130 g, 42%), m.p. 228°–230° C.;

NMR Spectrum: (CD$_3$SOCD$_3$) 1.27 (d, J=7.3 Hz, 3H, CHCH$_3$), 2.24 (m, 4H, CHC$\underline{H}_2$CH$_2$), and cyclopenta[g]quinazoline 7-CH$_2$), 2.32 (s, 3H, cyclopenta[g]quinazoline 2-CH$_3$), 2.91 (t, J=7.9 Hz, 2H, CHCH$_2$C$\underline{H}_2$), 2.97–3.20 (m, 3H, cyclopenta[g]quinazoline 8-CH$_2$ and C≡CH), 3.60, 3.64 (2×s, 6H, 2×CO$_2$Me), 3.96 (ABq, J=18.8 Hz, 2H, CH$_2$C≡C), 4.27 (m, 1H, C$\underline{H}$CH$_3$), 4.54 (m, 1H, —C$_6$H$_4$—CONHC$\underline{H}$), 5.21 (s, 2H, NC$\underline{H}_2$CONH), 5.75 (t, J=7.9 Hz, cyclopenta[g]quinazoline 6-CH), 7.00 (d, J=8.7 Hz, 2H, cyclopenta[g]quinazoline 9-H), 7.77 3',5'-ArH), 7.48 (s, 1H, cyclopenta[g]quinazoline 9-H), 7.77 (s, 1H, cyclopenta[g]quinazoline 5-H), 7.79 (d, J=8.6 Hz, 2H, 2', 6'-ArH), 8.55 (d, J=7.5 Hz, 1H, —C$_6$H$_4$—CON$\underline{H}$), 8.97 (d, J=6.9 Hz, 1H, N—CH$_2$CON$\underline{H}$), 12.13 (s, 1H, cyclopenta[g]quinazoline N3-H).

Mass Spectrum: (FAB) m/e 684 [(M+H)$^+$].
Elemental Analysis: Found C, 58.81; H, 5.41; N, 18.05; C$_{34}$H$_{37}$N$_9$O$_7$ 0.5 H$_2$O requires C, 58.95; H, 5.52; N, 18.20%.

(5) (2S)-2-{p-[N-((6RS)-2-Methyl-4-oxo-3,4,7,8-tetrahydro-6H-cyclopenta[g]quinazolin-6-yl)-N-(prop-2-ynyl)amino] benzamido}-4-{1-N-((1R)-1-carboxyethyl) carbamoylmethyl]tetrazol-5-yl}butyric acid To a stirred suspension of methyl (2S)-2-{p-[N-((6RS)-2-methyl-4-oxo-3,4,7,8-tetrahydro-6H-cyclopenta[g]quinazolin-6-yl)-N-(prop-2-ynyl)amino] benzamido}-4-{1-N-((1R)-1-(methoxycarbonyl)ethyl) carbamoylmethyl]tetrazol-5-yl}butyrate (0.085 g, 0.124 mmol) in methanol (2.0 ml) was slowly added 1N aqueous sodium hydroxide (0.5 ml, 0.5 mmol) followed by water (1 ml). Stirring was continued at room temperature for 4 hours, then more 1N aqueous sodium hydroxide (0.25 ml, 0.25 mmol) was added and the reaction mixture was stirred for a further 1 hour at room temperature. The solution was diluted with water (6 ml), acidified to pH ~3.5 wih 1N hydrochloric acid and the precipitated white solid was collected by filtration, washed with water (5 ml), and dried in vacuo over phosphorous pentoxide. There was thus obtained (2S)-2-{p-[N-((6RS)-2-methyl-4-oxo-3,4,7,8-tetrahydro-6 H-cyclopenta [g]quinazolin-6-yl)-N-(prop-2-ynyl)amino] benzamido}-4-{1[N-((1R)-1-carboxyethyl)carbamoyl-methyl]tetrazol-5-yl}butyric acid as a white solid (0.062 g, 77%), m.p. 182–189°

NMR Spectrum: (CD$_3$SOCD$_3$) 1.27 (d, J=7.3 Hz, 3H, CHC$\underline{H}_3$), 2.24 (m, 4H, CHC$\underline{H}_2$CH$_2$ and cyclopenta[g] quinazoline 7-CH$_2$), 2.33 (s, 3H, cyclopenta[g]quinazoline 2-CH$_3$), 2.89–3.25 (m, 5H, CHCH$_2$C$\underline{H}_2$, cyclopenta[g] quinazoline 8-CH$_2$ and C≡CH), 3.96 (ABq, J=19.0 Hz, 2H, CH$_2$C≡C), 4.18 (m, 1H, C$\underline{H}$CH$_3$), 4.46 (m, 1H, —C$_6$H$_4$—CONHC$\underline{H}$), 5.21 (s, 2H, NC$\underline{H}_2$CONH), 5.76 (t, J=8.4 Hz, cyclopenta[g]quinazoline 6-CH), 7.01 (d, J=8.0 Hz, 2H, 3',5'-ArH), 7.49 (s, 1H, cyclopenta[g]quinazoline 9-H), 7.78 (s, 1H, cyclopenta[g]quinazoline 5-H), 7.80 (d, J=8.6 Hz, 2H, 2',6'-ArH), 8.44 (d, J-7.8 Hz, 1H, —C$_6$H$_4$CON$\underline{H}$), 8.86 (d, J=7.2 Hz, 1H, N—CH$_2$CON$\underline{H}$), 12.14 (s, 1H, cyclopenta [g]quinazoline N3-H).

Mass Spectrum: (FAB) m/e 656 [(M+H)$^+$].

Elemental Analysis: Found C, 56.34; H, 5.16; N, 18.27; C$_{32}$H$_{33}$N$_9$O$_7$ 1.5 H$_2$O requires C, 56.30; H, 5.31; N, 18.46%.

Example 17

(2S)-2-{p-[N-((6RS)-2-methyl-4-oxo-3,4,7,8-tetrahydro-6 H-cyclopenta[g]quinazolin-6-yl)-N-(prop-2-ynyl) amino]benzamido}-5-(1 H-1,2,4-triazol-3-ylsulphonyl)pentanoic acid (1) Methyl (2S)-2-[N-(benzyloxycarbonyl)amino]-5-hydroxypentanoate To a stirred solution of α-methyl N-(benzyloxycarbonyl)-L-glutamate (4.0 g, 13.56 mmol) in dry THF (33 ml) cooled to −10° C. and under argon was added triethylamine (2.05 g, 20.34 mmol) followed by ethyl chloroformate (1.83 g, 16.95 mmol). After stirring at −10° C. for 10 minutes, sodium boronhydride (1.54 g, 40.68 mmol) was added in one portion followed by dropwise addition of methanol (40 ml) over a 15 minute period while the temperature was maintained below 0° C. Stirring was continued at 0° C. for 40 minutes and then the reaction mixture was neutralised with 1N aqueous sodium hydroxide. The organic solvents were then removed in vacuo and the residue was extracted with ethyl acetate (2×180 ml). The combined ethyl acetate extracts were washed with saturated aqueous sodium bicarbonate (2×100 ml), water (100 ml), dried (Na$_2$SO$_4$), and concentrated in vacuo to an oily residue. This was purified by column chromatography using a gradient of ethyl acetate in hexanes (50 to 90%) as eluant. There was thus obtained methyl (2S)-2-[N-(benzyloxycarbonyl) amino]-5-hydroxypentanoate (1.98, 52%) as a colourless oil.

NMR Spectrum: (CD$_3$SOCD$_3$) 1.40–1.80 (m, 4H, 3-CH$_2$ and 4-CH$_2$), 3.37 (q(obscured), 2H, J=5.9 Hz, C$\underline{H}_2$OH), 3.62 (s, 3H, CO$_2$Me), 4.02 (m, 1H, 2-CH), 4.47 (t, J=5.2 Hz, CH$_2$O$\underline{H}$, exchangeable with D$_2$O), 5.03 (s, 2H, PhCH$_2$), 7.35 (m, 5H, Ph), 7.77 (d, J=7.7 Hz, 1H, CONH).

Elemental Analysis: Found C, 59.64; H, 6.72; N, 4.98; C$_{14}$H$_{19}$NO$_5$ requires C, 59.78; H, 6.81; N, 4.98%.

(2) Methyl (2S)-2-[N-(benzyloxycarbonyl)amino]-5-(methylsulphonyloxy)-pentanoate To a solution of methyl ((2S)-2-[N-(benzyloxycarbonyl) amino]-5-hydroxy-pentanoate (1.84 g, 6.98 mmol) in dichloromethane (27 ml) cooled to −10° C. under argon was added triethylamine (1.057 g, 10.47 mmol) and then methanesulphonyl chloride (0.99 g, 8.72 mmol) over a 2 minute period. Stirring was continued for 35 minutes while the temperature was maintained below 0° C. The reaction mixture was then diluted with dichloromethane (200 ml) and washed with water (100 ml), 10% aqueous citric acid (2×100 ml), saturated aqueous sodium bicarbonate (100 ml) and dilute brine (100 ml), dried (Na$_2$SO$_4$) and concentrated in vacuo to a yellow oil residue. Purification by column chromatography, on elution with 1:1 v/v ethyl acetate/ hexanes, afforded methyl (2S)-2-{N-(benzyloxycarbonyl) amino]-5-(methylsulphonyloxy)-pentanoate as a colourless viscous oil (2.40 g, 96%);

NMR Spectrum: (CD$_3$SOCD$_3$) 1.72 (m, 4H, 3-CH$_2$ and 4-CH$_2$), 3.15 (s, 3H, OSO$_2$Me), 3.64 (s, 3H, CO$_2$Me), 4.08 (m, 1H, 2-CH), 4.18 (t, J=5.3 Hz, C$\underline{H}_2$OSO$_2$Me), 5.05 (s, 2H, PhCH$_2$), 7.35 (m, 5H, Ph), 7.78 (d, J=7.8 Hz, 1H, CONH).

Mass Spectrum: (FAB) m/e 360 [(M+H)$^+$].

Elemental Analysis: Found C, 50.04; H, 5.84; N, 3.84; S, 8.99;

C$_{15}$H$_{21}$NO$_7$S requires C, 50.13; H, 5.89; N, 3.90; S, 8.92%.

(3) Methyl (2S)-2-[N-(benzyloxycarbonyl)amino]-5-(1H-1, 2,4-triazol-3-ylthio)-pentanoate To a stirred solution of methyl (2S)-2-[N-(benzyloxycarbonyl) amino]-5-(methylsulphonyloxy) pentanoate (2.35 g, 6.54 mmol) in anhydrous DMF (6.5 ml) and under argon was added 1H-1,2,4-triazole-3-thiol (0.86 g, 8.50 mmol) followed by triethylamine (0.86 g, 8.50 mmol). The reaction mixture was stirred at room temperature for 90 hours, then it was diluted with ethyl acetate (200 ml) and the resulting solution was washed with 10% aqueous citric acid (100 ml), brine (100 ml) and water (100 ml), dried (Na$_2$SO$_4$) and concentrated in vacuo to a yellow oily residue. Purification by column chromatography, on gradient elution with ethyl acetate in hexanes (40 to 80%) afforded a gum (1.84 g, 77%) which solidifed on standing at room temperature. There was thus obtained methyl (2S)-2 [N-(benzyloxycarbonyl)-amino]-5-(1 H-1,2,4-triazol-3-ylthio)pentanoate as a white solid, m.p. 99°–100° C.;

NMR Spectrum: 1.63–1.90 (m, 4H, 3-CH$_2$ and 4-CH$_2$), 3.06 (t, J=6.3 Hz, 2H, CH$_2$S—), 3.61 (s, 3H, CO$_2$Me), 4.05 (m, 1H, 2-CH), 5.03 (s, 2H, PhCH$_2$), 7.35 (m, 5H, Ph), 7.80 (d, J=7 8 Hz, 1H, CONH), 8.4 (br s, N=C$\underline{H}$).

Mass Spectrum: (FAB) m/e 365 [(M+H)$^+$].

Elemental Analysis: Found C, 52.95; H, 5.56; N, 15.41; S, 8.83;

C$_{16}$H$_{20}$N$_4$O$_4$S requires C, 52.73; H, 5.53; N, 15.37; S, 8.80%.

(4) Methyl (2S)-[N-(benzyloxycarbonyl)amino]-5-(1H-1,2, 4-triazol-3-ylsulphonyl)pentanoate To a stirred solution of methyl (2S)-2-[N-(benzyloxycarbonyl)amino]-5-(1 H-1,2,4-triazol-3-ylthio)pentanoate (0.660 g, 1.8 mmol) in chloroform (8 ml) cooled to −10° C. and under argon was added a suspension of m-chloroperoxybenzoic acid (technical 80–90%, 0.775 g, ~3.6 mmol) in chloroform (8 ml) (precooled to −10° C.) using chloroform (4 ml) to aid the transfer. Stirring was continued at –10° C. for 5 minutes and then the reaction mixture was allowed to stand at –20° C. for 23 hours. The white solid was filtered off, the filtrate was concentrated in vacuo to a semisolid residue which was purified by column chromatrography using a gradient of ethyl acetate in hexanes (50 to 100%) as eluant. There was thus obtained methyl (2S)-2-[N-(benzyloxy-carbonyl)amino]-5-(1H-1,2,4-triazol-3-ylsulphonyl)pentanoate as a gummy solid (0.410 g, 58%).

NMR Spectrum: 1.63–1.90 (m, 4H, 3-CH$_2$ and 4-CH$_2$), 3.42 (m, 2H, CH$_2$SO$_2$—), 3.61 (s, 3H, CO$_2$Me), 4.06 (m, 1H, 2-CH), 5.03 (s, 2H, PhCH$_2$), 7.36 (m, 5H, Ph), 7.80 (d, J=7.8 Hz, 1H, CONH), 8.9 (s, 1H, N=CH).

Mass Spectrum: (FAB) m/e 397 [(M+H)$^+$].

Elemental Analysis: Found C, 48.65; H, 5.05; N, 13.82; S, 7.84;

C$_{16}$H$_{20}$N$_4$O$_6$S requires C, 48.48; H, 5.09; N, 14.13; S, 8.09%.

(5) Methyl (2S)-2-amino-5-(1H-1,2,4-triazol-3-ylsulphonyl)pentanoate

To a solution of methyl (2S)-2-[N-benzyloxycarbonyl)amino]-5-(1H-1,2,4-triazol-3-ylsulphonyl)pentanoate (0.330 g, 0.83 mmol) in ethanol (24 ml) was added 10% Pd/C (0.350 g). The resulting black mixture was degassed and stirred at 26° C. for 4 hours under hydrogen. More catalyst (0.050 g) was then added and stirring was continued at 26° C. for a further 2 hours. The catalyst was removed by filtration and the filtrate was concentrated in vacuo to a gummy residue which dried in vacuo over phosphorous pentoxide to give a white solid (0.182 g), a mixture of the starting material and methyl (2S)-2-amino-5-(1H-1,2,4-triazol-3-ylsulphonyl)pentanoate (ratio 0.6:1, as estimated by NMR). This was used without further purification.

(6) Methyl (2S)-2-{p-[N-((6RS)-2-methyl-4-oxo-3,4,7,8-tetrahydro-6H-cyclopenta [g]quinazolin-6-yl)-N-(prop-2-ynyl)amino]benzamido}-5-(1H-1,2,4-triazol-3-ylsulphonyl)pentanoate To a stirred solution of methyl (2S)-2-amino-5-(1H-1,2,4-triazol-3-ylsulphonyl)pentanoate (0.182 g, supposedly 0.36 mmol of free amine) in anhydrous DMF (2.5 ml) cooled to 0° C. under argon was added p-[N-((6RS)-2-methyl-4-oxo-3,4,7,8-tetrahydro-6 H-cyclopenta[g]quinazolin-6-yl)-N-(prop-2-ynyl)amino]benzoic acid (0.112 g, 0.30 mmol), prepared as described in Example 13(5), followed by (1H-1,2,3-benzotriazol-1-yloxy-tris[pyrrolidino]-phosphonium hexafluorophosphate[PyBOP (registered trade mark), 0.163 g, 0.315 mmol] and then diisopropylethylamine (0.116 g, 0.9 mmol). A clear solution was obtained after ~1 minute. This was stirred at –0° C. for 5 minutes, the ice-bath was then removed and stirring was continued for a further 3 hours before the reaction mixture being concentrated in vacuo to a gummy residue. This was triturated with dichloromethane (5 ml), the precipitated brown solid was filtered off and the filtrate was concentrated in vacuo to brownish oily residue which was purified by column chromatography using a gradient of methanol in chloroform (2 to 7%) as eluant. The product, still impure, was rechromatographed using 10% methanol in dichloromethane as eluant to give a white solid which was triturated with hexanes, collected by filtration and washed with hexanes. There was thus obtained methyl (2S)-2-{p-[N-((6RS)-2-methyl-4-oxo-3,4,7,8-tetrahydro-6 H-cyclopenta[g]quinazolin-6-yl)-N-(prop-2-ynyl)amino] benzamido}-5-(1H-1,2,4-triazol-3-ylsulphonyl)pentanoate as a white solid (0.050 g, 27%), m.p. 174°–178° C. (softens);

NMR Spectrum: (CD$_3$SOCD$_3$) 1.60–2.00, 2.21 (2×, 6H, 3-CH$_2$ and 4-CH$_2$ and cyclopenta[g]quinazoline 7-CH$_2$, 2.33 (s, 3H, cyclopenta[g]quinazoline 2-CH$_3$), 2.90–3.20 (m, 3H, cyclopenta[g]quinazoline 8-CH$_2$ and C≡CH), 3.44 (m, 2H, CH$_2$SO$_2$—), 3.96 (ABq, J=18.94 Hz, 2H, CH$_2$C≡C), 3.61 (s, 3H, CO$_2$Me), 4.39 (m, 1H, 2-CH), 5.76 (t, J=7.5 Hz, cyclopenta[g]quinazoline 6-CH), 7.02 (d, J=8.0 Hz, 2H, 3',5'-ArH), 7.49 (s, 1H, cyclopenta[g]quinazoline 9-H), 7.75 (d, J=8.9 Hz, 2H, 2',6'-ArH), 7.79 (s, 1H, cyclopenta[g]quinazoline 5-H), 8.45 (d, J=7.4 Hz, 1H, CONH), 8.85 (s, 1H, N=CH), 12.14 (s, 1H, cyclopenta[g] quinazoline N3-H).

Mass Spectrum: (FAB) m/e 618 [(M+H)$^+$].

(7) (2S)-2-{p-[N-((6RS)-2-Methyl-4-oxo-3,4,7,8-tetrahydro-6H-cyclopenta [g]quinazolin-6-yl)-N-(prop-2-ynyl)amino]benzamido}-5-(1H-1,2,4-triazol-3-ylsulphonyl)pentanoic acid To a solution of methyl (2S)-2-{p-[N-((6RS)-2-methyl-4-oxo-3,4,7,8-tetrahydro-6H-cyclopenta [g]quinazolin-6-yl)-N-(prop-2-ynyl)amino]benzamido}-5-(1H-1,2,4-triazol-3-ylsulphonyl)pentanoate (0.038 g, 0.062 mmol) in methanol (1 ml) was slowly added 1N aqueous sodium hydroxide (0.15 ml, 0.15 mmol) followed by water (1 ml). The reaction mixture was stirred at room temperature for 2.5 hours then more 1N aqueous sodium hydroxide (0.10 ml, 0.10 mmol) was added and stirring was continued at room temperature for 1 hour. The solution was then diluted with water (3 ml), acidified to pH ~4 with 1N hydrochloric acid and the precipitated white solid was collected by filtration, washed with water (~3 ml) and dried in vacuo over phosphorous pentoxide. There was thus obtained (2S)-2-{p-[N-((6RS)-2-methyl-4-oxo-3,4,7,8-tetrahydro-6 H-cyclopenta[g]quinazolin-6-yl)-N-(prop-2-ynyl)amino]benzamido}-5-(1H-1,2,4-triazol-3-ylsulphonyl)pentanoic acid as a white solid (0.021 g, 57%), m.p. 180° C. (dec).

NMR Spectrum: (CD$_3$SOCD$_3$) 1.60–2.00, 2.20 (2×m, 6H, 3-CH$_2$ and 4-CH$_2$ and cyclopenta[g]quinazoline 8-CH$_2$), 2.34 (s, 3H, cyclopenta[g]quinazoline 2-CH$_3$), 2.90–3.23 (m, 3H, cyclopenta[g]quinazoline 7-CH$_2$ and C≡CH), 3.40 (m, 2H, CH$_2$SO$_2$—), 3.96 (ABq, J=18.53 Hz, 2H, CH$_2$C≡C), 4.32 (m, 1H, 2-CH), 5.76 (t, J=7.2 Hz, cyclopenta[g]quinazoline 6-CH), 7.02 (d, J=8.3 Hz, 2H, 3',5'-ArH), 7.49 (s, 1H, cyclopenta[g]quinazoline 9-H), 7.77 (d, J=8.9 Hz, 2H, 2',6'-ArH), 7.80 (s, 1H, cyclopenta[g] quinazoline 5-H), 8.32 (d, J=7.7 Hz, 1H, CONH), 8.87 (s, 1H, N=CH), 12.10 (s, 1H, cyclopenta[g]quinazoline N3-H).

Mass Spectrum: (FAB) m/e 604 [(M+H)$^+$].

Elemental Analysis: Found C, 54.92; H, 5.07; N, 15.47; C$_{29}$H$_{29}$N$_7$O$_6$S 1.5 H$_2$O requires C, 55.23; H, 5.11; N, 15.55%.

Example 18

(4R)-4-{N-{N-{p-[N-((6RS)-2-Methyl-4-oxo-3,4,7,8-tetrahydro-6 H-cyclopenta[g]quinazolin-6-yl)-N-(prop-2-ynyl)amino]benzoyl}-L-γ-glutamyl}amino}-4-(tetrazol-5-yl)butyric acid (1) tert-Butyl (4R)-4-(benzyloxycarbonylamino)-4-carbamoylbutyrate A stirred solution of N-benzyloxycarbonyl-D-glutamic acid γ-tert-butyl ester (4.75 g, 14 mmol) and triethylamine (2.0 ml, 14 mmol) in dry THF (28 ml) was cooled to –15° C. under argon and a solution of isobutyl chloroformate (1.92 g, 14 mmol) in THF (11 ml) was added during 5 minutes. After a further 10 minutes at –15° C. gaseous ammonia was bubbled through the mixture for 30 minutes, during which the temperature was kept at –5° to +5° C. The mixture was then allowed to warm to room temperature. The precipitate was removed by filtration and the filtrate evaporated. The residue was dissolved in ethyl acetate (150 ml) and the solution was washed successively with saturated aqueous sodium hydrogen carbonate (2×35 ml), water (35 ml), 10% citric acid solution (35 ml), and water (2×35 ml), then dried (Na$_2$SO$_4$) and evaporated. The residue was dissolved in the minimum volume of dichloromethane and the solution added dropwise to hexane (300 ml) with stirring. The precipitate was collected, washed with hexane and dried to give tert-butyl (4R)-4-(benzyloxycarbonylamino)-4-carbamoylbutyrate (3.638 g, 77%), m.p. 138°–140° C.

NMR Spectrum: (CD$_3$SOCD$_3$) 1.38 (s, 9H, C(CH$_3$)$_3$), 1.70 (m, 1H, β-CH$_2$), 1.85 (m, 1H, β-CH$_2$), 2.22 (t, J=7.8 Hz, 2H, γ-CH$_2$), 3.92 (m, 1H, α-CH), 5.02 (m, 2H, PhC$\underline{H}_2$), 7.07 (s, 1H, α-NH), 7.35 (m, 5H, Ph).

Mass Spectrum: (FAB) m/e 359 [(M+Na)$^+$], 337 [(M+H)$^+$].

Elemental Analysis: Found C, 60.51; H, 7.15; N, 8.24%; C$_{17}$H$_{24}$N$_2$O$_5$ requires C, 60.70; H, 7.19; N, 8.33%.

Optical Rotation: (CHCl$_3$)[α]$_D^{19}$ °4.8° (c=1).

(2) tert-Butyl (4R)-4-(benzyloxycarbonylamino)-4-cyanobutyrate

A solution of phosphorus oxychloride (2.05 g, 13.4 mmol) in dichloromethane (5.5 ml) was added during 20 minutes to a stirred solution of tert-butyl (4R)-4-(benzyloxycarbonylamino)-4-carbamoylbutyrate (3.0 g, 8.9 mmol) in dry pyridine (16 ml) at −5° C. under argon. The mixture was allowed to warm to room temperature and after 25 hours was poured into cold water (110 ml). The products were extracted with ethyl acetate (4×40 ml) and the combined ethyl acetate solution was washed successively with 10% aqueous citric acid solution (4×15 ml) and water (25 ml), then dried (Na$_2$SO$_4$) and evaporated. Toluene (4×25 ml) was added and evaporated and the residue was chromatographed with increasingly polar mixtures of hexane and ethyl acetate (100:0 to 2:1) as eluant to give tert-butyl (4R)-4-(benzyloxycarbonylamino)-4-cyanobutyrate (2.433 g, 86%) as a pale yellow oil.

NMR Spectrum: (CD$_3$SOCD$_3$) 1.39 (s, 9H, C(CH$_3$)$_3$), 1.95 (m, 2H, β-CH$_2$), 2.34 (t, J=7.4 Hz, 2H, γ-CH$_2$), 4.61 (q, 1H, α-CH), 5.08 (s, 2H, PhC$\underline{H}_2$), 7.37 (m, 5H, Ph), 8.21 (d, J=8.0 Hz, 1H, NH).

Mass Spectrum: (FAB) m/e 341 [(M+Na)$^+$], 319 [(M+H)$^+$].

Elemental Analysis: Found C, 63.93; H, 7.03; N, 8.77%; C$_{17}$H$_{22}$N$_2$O$_4$ requires C, 64.13; H, 6.97; N, 8.80%.

Optical Rotation: (CHCl$_3$) [a]$_D^{19}$ °40.5° (c=1).

(3) tert-Butyl (4R)-4-(benzyloxycarbonylamino)-4-(tetrazol-5-yl)butyrate

A mixture of tert-butyl (4R)-4-(benzyloxycarbonylamino)-4-cyanobutyrate (1.53 g, 4.8 mmol), ammonium chloride (0.28 g, 5.2 mmol), sodium azide (0.345 g, 5.3 mmol) and dry DMF (6 ml) was stirred and heated at 90°–95° C. under argon for 20 hours. The mixture was cooled and concentrated and the residue partitioned between ice-cooled water (40 ml) and ethyl acetate (30 ml) with the pH of the aqueous phase being adjusted to 3 by the addition of 10% aqueous citric acid solution (ca. 10 ml). The aqueous layer was extracted with further ethyl acetate (3×30 ml) and the combined organic solution washed with water (4×25 ml), dried (MgSO$_4$) and evaporated. A solution of the residue in dichloromethane (3 ml) was added dropwise to stirred hexane (20 ml) and the precipitate was collected, washed with hexane and dried to give tert-butyl (4R)-4-(benzyloxycarbonylamino)-4-(tetrazol-5-yl)butyrate (1.462 g, 84%), m.p. 99°–101° C.

NMR Spectrum: (CD$_3$SOCD$_3$) 1.39 (s, 9H, C(CH$_3$)$_3$C), 2.03, 2.15 (2×m, 2H, β-CH$_2$), 2.31 (m, 2H, γ-CH$_2$), 5.04 (m, 3H, α-CH, PhC$\underline{H}_2$), 7.36 (m, 5H, Ph), 7.97 (d, J=8.0 Hz, 1H, NH).

Mass Spectrum: (FAB) m/e 384 [(M+Na)$^+$], 362 [(M+H)$^+$].

Elemental Analysis: Found C, 56.44; H, 6.44; N, 19.38%; C$_{17}$H$_{23}$N$_5$O$_4$ requires C, 56.50; H, 6.42; N, 19.38%.

Optical Rotation: (CHCl$_3$) [α]$_D^{18}$°34.0° (c=1).

(4) tert-Butyl (4R)-4-amino-4-(tetrazol-5-yl)butyrate

A solution of tert-butyl (4R)-4-(benzyloxycarbonylamino)-4-(tetrazol-5-yl)-butyrate (1.2 g, 3.32 mmol) in ethanol (77 ml) was stirred with 10% Pd-C (0.166 g) under a hydrogen atmosphere at ambient temperature for 16 hours. The catalyst was removed by filtration and the filtrate evaporated. Dichloromethane was added to the residue and evaporated and the resulting solid was triturated with hexane and dried to give tert-butyl (4R)-4-amino-4-(tetrazol-5-yl)butyrate (0.687 g, 91%), m.p. 175° C. (decomp.).

NMR Spectrum: (CD$_3$SOCD$_3$) 1.38 (s, 9H, C(CH$_3$)$_3$C), 2.07 (m, 2H, β-CH$_2$), 2.26 (m, 2H, γ-CH$_2$), 4.44 (dd, J=6.2, 7.7 Hz, 1H, α-CH), 8.28 (br. s, 3H, NH$_3$+).

Mass Spectrum: (FAB) 250 [(M+Na)$^+$], 228 [(M+H)$^+$].

(5) tert-Butyl (4R)-4-{N-[N-(benzyloxycarbonyl)-α-tert-butyl-(S)-γ-glutamyl]amino}-4-(tetrazol-5-yl)butyrate A stirred solution of N-(benzyloxycarbonyl)-L-glutamic acid α-tert-butyl ester (0.891 g, 2.64 mmol) in dry THF (10 ml) was cooled to −20° C. under argon and 4-methylmorpholine (0.27 g, 2.64 mmol) and isobutyl chloroformate (0.36 g, 2.64 mmol) were added successively. After 10 minutes at −20° C., solid tert-butyl (4R)-4-amino-4-(tetrazol-5-yl)butyrate (0.60 g, 2.64 mmol) and further THF (5 ml) were added. After a further 15 minutes at −20° C., the mixture was stirred at room temperature for 4.5 hours. It was then filtered and the filtrate was concentrated. A solution of the residual syrup in ethyl acetate (100 ml) was washed successively with 10% aqueous citric acid solution (50 ml) and half-saturated brine (3×20 ml), then dried (MgSO$_4$) and evaporated. Column chromatography of the residue with increasingly polar mixtures of dichloromethane and ethanol (100:0 to 90:10 v/v), followed by trituration with hexane, gave tert-butyl (4R)-4-{N-[N-(benzyloxycarbonyl)-α-tert-butyl-(S)-γ-glutamyl]amino -4-(tetrazol-5-yl)butyrate (0.948 g, 66%), m.p. 143°–145° C.

NMR Spectrum: (CD$_3$SOCD$_3$) 1.38, 1.39 (2×s, 18H, C(CH$_3$)$_3$C), 1.81, 1.99, 2.13, 2.28 (4×m, 8H, L-glu β-CH$_2$, L-glu γ-CH$_2$, β'-CH$_2$, γ'-CH$_2$), 3.90 (m, 1H, L-gluα-CH), 5.03 (m, 2H, PhC$\underline{H}_2$), 5.17 (m, 1H, α'-CH), 7.35 (m, 5H, Ph), 7.58 (d, J=7.7 Hz, 1H, L-glu NH), 8.43 (d, J=7.9 Hz, 1H, α'-NH), 13.6 (br., tetrazole NH).

Mass Spectrum: (FAB) m/e 569 [(M+Na)$^+$], 547 [(M+H)$^+$].

Elemental Analysis: Found C, 57.07; H, 6.99; N, 15.18%; C$_{26}$H$_{38}$N$_6$O$_7$ requires C, 57.13; H, 7.01; N, 15.37%.

(6) tert-Butyl (4R)-4-[N-(α-tert-butyl-(S)-γ-glutamyl)amino]-4-(tetrazol-5-yl)butyrate A solution of tert-butyl (4R)-4-{N-[N-(benzyloxycarbonyl)-αtert-butyl-(S)-γ-glutamyl]amino}-4-(tetrazol-5-yl)butyrate (0.320 g, 0.585 mmol) in ethanol (35 ml) was stirred with 10% Pd-C (0.12 g) under a hydrogen atmosphere at ambient temperature. After 16 hours further 10% Pd-C. (0.09 g) was added and the mixture was stirred under hydrogen for a further 6 hours. It was then filtered through Celite and the filtrate was evaporated. Several portions of dichloromethane were added and evaporated to leave tert-butyl (4R)-4-[N-(α-tert-butyl-(S)-γ-glutamyl)

amino]-4-(tetrazol-5-yl)butyrate as a crisp, colourless glass which was dried over phosphorus pentoxide and used without further purification. Yield 0.24 g; m.p. 92°–94° C.

NMR Spectrum: (CD$_3$SOCD$_3$) 1.38, 1.43, 1.45 (3×s, 18H, C(CH$_3$)$_3$C), 1.91., 2.03, 2.19, 2.28 (4×m, 8H, L-glu β-CH$_2$, L-glu γ-CH$_2$, β'-CH$_2$, γ'-CH$_2$), 3.76 (t, J=6.4 Hz, 1H, L-glu α-CH), 5.08 (m, 1H, α'-CH), 6.1 (br., 3H, NH$_3$+), 8.29 (d, J=8.4 Hz, 1H, CONH). Additional minor signals (e.g. 8.21, equivalent to ca. 0.2H) suggest impurities were present.

Mass Spectrum: (FAB) m/e 413 [(M+Na)$^+$].

(7) tert-Butyl (4R)-4-{N-{N-{p-[N-((6RS)-2-methyl-4-oxo-3,4,7,8-tetrahydro-6H-cyclopenta [g]quinazolin-6-yl)-N-(prop-2-ynyl)amino]benzoyl}-α-tert-butyl-L-γ-glutamyl}amino}-4-(tetrazol-5-yl)butyrate (1H-1,2,3-Benzotriazol-1-yloxy)-tris(pyrrolidino) phosphonium hexafluorophosphate (0.30 g, 0.578 mmol) and N,N-diisopropylethylamine (0.30 ml, 1.7 mmol) were added successively to a stirred, cooled (ice-water bath) mixture of p-[N-((6RS)-2-methyl-4-oxo-3,4,7,8-tetrahydro-6H-cyclopenta[g]quinazolin-6-yl)-N-(prop-2-ynyl)amino] benzoic acid (0.190 g, 0.50 mmol), prepared as described in Example 4(4), tert-butyl (4R)-4-[N-(α-tert-butyl-(S)-γ-glutamyl) amino]-4-(tetrazol-5-yl)butyrate (0.23 g, 0.57 mmol) and dry DMF (3 ml) under argon. After 5 minutes the mixture was allowed to come to room temperature, and after a further 2.5 hours it was partitioned between ethyl acetate (75 ml) and 10% aqueous citric acid solution (75 ml). The aqueous layer was extracted with ethyl acetate (2×50 ml) and the combined ethyl acetate solution washed successively with 10% citric acid (75 ml) and half-saturated brine (4×25 ml), then dried (Na$_2$SO$_4$) and evaporated. The residue was chromatographed twice with increasingly polar mixtures of dichloromethane and ethanol. The more polar product was isolated as a glass which was triturated with hexane, then dissolved in dichloromethane (5 ml). The solution was added to stirred hexane (30 ml) and the resulting precipitate collected, washed with hexane and dried. There was thus obtained tert-butyl (4R)-4-{N-{N-{p-[N-((6RS)-2-methyl-4-oxo-',3,4,7,8-tetrahydro-6H-cyclopenta[g]quinazolin-6-yl)-N-(prop-2-ynyl)amino]benzoyl}-α-tert-butyl-L-γ-glutamyl}amino}-4-(tetrazol-5-yl)butyrate (0.213 g, 55%), m.p. 154°–156° C.

NMR Spectrum: (CD$_3$SOCD$_3$) 1.37, 1.38, 1.41 (3×s, 18H, (CH$_3$)$_3$C), 1.94, 2.08, 2.24 (3×m, 9H, L-glu β-CH$_2$, L-glu γ-CH$_2$, β'-CH$_2$, γ'-CH$_2$, cyclopenta[g]quinazoline C7-H), 2.33 (s, 3H, C2-CH$_3$), 2.5 (m, presumed 1H, coincides with solvent signal, cyclopenta[g]quinazoline C7-H), 3.02 (m, 1H, cyclopenta[g]quinazoline C8-H), 3.13 (m, 2H, C≡CH, cyclopenta[g]quinazoline C8-H), 3.84 (m, 1H, CH$_2$C≡C), 4.10 (m, 1H, CH$_2$C≡C), 4.28 (m, 1H, L-glu α-CH), 5.15 (m, 1H, α'-CH), 5.76 (t, J=8 Hz, 1H, cyclopenta [g]quinazoline C6-H), 7.02 (d, J=9.0 Hz, 2H, 3',5'-ArH), 7.49 (s, 1H, cyclopenta[g]quinazoline C9-H), 7.81 (m, 3H, 2',6'-ArH, cyclopenta[g]quinazoline C5-H), 8.40 (m, 2H, L-glu NH, α'-NH), 12.14 (s, 1H, cyclopenta[g]quinazoline N3-H).

Mass Spectrum: (FAB) m/e 790 [(M+Na)$^+$].

Elemental Analysis: Found C, 59.67; H, 6.43; N, 16.36; C$_{40}$H$_{49}$N$_9$O$_7$ requires C, 60.03; H, 6.62; N, 15.75%.

(8) (4R)-4-{N-{N-{p-[N-((6RS)-2-Methyl-4-oxo-3,4,7,8-tetrahydro-6H-cyclopenta[g]quinazolin-6-yl)-N-(prop-2-ynyl)amino]benzoyl}-L-γ-glutamyl}amino}-4-(tetrazol-5-yl)butyric acid tert-Butyl (4R)-4-{N-{N-{p-[N-((6RS)-2-methyl-4-oxo-3,4,7,8-tetrahydro-6H-cyclopenta[g]quinazolin-6-yl)-N-(prop-2-ynyl)amino]benzoyl}-α-tert-butyl-L-γ-glutamyl}amino}-4-(tetrazol-5-yl)butyrate (0.100 g, 0.130 mmol) was added to a stirred, cooled (ice-water bath) mixture of trifluoroacetic acid (7.9 ml), thioanisole (0.44 ml, 3.7 mmol), ethanedithiol (0.22 ml, 2.6 mmol) and water (0.22 ml). After 15 minutes the mixture was brought to room temperature and stirred in the dark for a further 1 hour. It was then evaporated and the residue triturated with diethyl ether. The resulting solid was dissolved in 0.5M aqueous sodium hydrogen carbonate (12 ml) and the solution was washed with dichloromethane (5×5 ml), using a centrifuge to assist separation into two layers. The aqueous solution was filtered through a cellulose nitrate membrane filter (0.65 lm pore size) and acidified to pH 3.5 by addition of 1M hydrochloric acid, whilst stirring and cooling in ice. The resulting suspension was centrifuged and the precipitate washed once by resuspension and centrifugation, then collected by filtration further washed with water, diethyl ether and dichloromethane in succession, then dried. There was thus obtained (4R)-4-{N-{N-{p-[N-((6RS)-2-methyl-4-oxo-3,4,7,8-tetrahydro-6H-cyclopenta[g]quinazolin-6-yl)-N-(prop-2-ynyl)amino]benzoyl}-L-γ-glutamyl}amino}-4-(tetrazol-5-yl)butyric acid (0.045 g, 53%), m.p. 175°–177° C.

NMR Spectrum: 1.95, 2.1–2.4 (2×m), 2.33 (s) (total 12H, L-glu β-CH$_2$, L-glu γ-CH$_2$, β'-CH$_2$, γ'-CH$_2$, cyclopenta[g] quinazoline C7-H, C2-CH$_3$), 2.5 (m, presumed 1H, coincides with solvent signal, cyclopenta[g]quinazoline C7-H), 3.02 (m, 1H, cyclopenta[g]quinazoline C8-H), 3.14 (m, 2H, C≡CH, cyclopenta[g]quinazoline C8-H), 3.84 (m, 1H, CH$_2$C≡C), 4.10 (m, 1H, CH$_2$C≡C), 4.41 (m, 1H, L-glu α-CH), 5.19 (m, 1H, α'-CH), 5.77 (t, J=8 Hz, 1H, cyclopenta [g]quinazoline C6-H), 7.03 (d, J=9.0 Hz, 2H, 3',5'-ArH), 7.49 (s, 1H, cyclopenta[g]quinazoline C9-H), 7.81 (m, 3H, 2',6'-ArH, cyclopenta[g]quinazoline C5-H), 8.44 (d, J=7.8 Hz, 1H), 8.55 (d, J=7.7 Hz, 1H) (L-glu NH, α'-NH), 12.15 (s, 1H, cyclopenta[g]quinazoline N3-H); impurity signals: 1.23 (s), 1.38 (s), 1.42 (s), 1.65 (s), 1.69 (s) (total equivalent to ca. 1.7H), 8.35 (ca. 0.2H).

Mass Spectrum: (FAB) m/e 678 [(M+Na)$^+$].

Elemental Analysis: Found C, 56.71; H, 5.42; N, 18.28; C$_{32}$H$_{33}$N$_9$O$_7$ 1.4 H$_2$O requires C, 56.45; H, 5.30; N, 18.51%.

Example 19

N-{N-{p-[N-((6RS)-2-methyl-4-oxo-3,4,7,8-tetrahydro-6H-cyclopenta[g]quinazolin-6-yl)-N-(prop-2-ynyl)amino]benzoyl}-L-γ-glutamyl}-D-alanine (1) Di-tert-butyl N-{N-{p-[N-((6RS)-2-methyl-4-oxo-3,4,7,8-tetrahydro-6H-cyclopenta [g]quinazolin-6-yl)-N-(prop-2-ynyl)amino]benzoyl}-L-γ-glutamyl}-D-alaninate To a stirred solution of di-tert-butyl L-γ-glutamyl-D-alaninate (0.171 g, 0.52 mmol), prepared as described in U.K. Patent Application GB 2,253,849A, in anhydrous DMF (3.5 ml) cooled to 0° C. was added p-[N-((6RS)-2-methyl-4-oxo-3,4,7,8-tetrahydro-6H-cyclopenta[g]quinazolin-6-yl)-N-(prop-2-ynyl)amino] benzoic acid (0.150 g, 0.40 mmol), prepared as described in Example 13(5), followed by diethyl phosphorocyanidate (0.143 g, 0.88 mmol) and triethylamine (0.089 g, 0.88 mmol) (a clear solution was obtained after a few seconds). Stirring was continued at 0° C. for 10 minutes under argon; the ice-bath was then removed and the reaction mixture was stirred for a further 2 hours before being partitioned between ethyl acetate (100 ml) and water (100 ml). The two layers were separated and the aqueous layer was extracted with ethyl acetate (150 ml) and dichloromethane (70 ml). The organic extracts were combined and washed with 10% aqueous citric acid (100 ml), saturated aqueous bicarbonate (100 ml) and dilute brine (100 ml), dried (Na$_2$SO$_4$) and concentrated in vacuo to a gummy residue. Purification by column chromatography, on elution with ethyl acetate (~200 ml) and then 2% methanol in chloroform afforded a pale yellow solid. This was rechromatographed using a gradient of methanol in ethyl acetate (0 to 4%) as eluant. The product, a white solid, was reprecipiated from dichloromethane (~5 ml)/hexanes. There was thus obtained di-tert-butyl N-{N-{p-[N-((6RS)-2-methyl-4-oxo-3,4,7,8-tetrahydro-6 H-cyclopenta[g]quinazolin-6-yl)-N-(prop-2-ynyl) amino]-benzoyl}-L-γ-glutamyl}-D-alaninate as a white solid (0.195 g, 71%), m.p. 145°–148° C. (softens);

NMR Spectrum: (CD$_3$SOCD$_3$) 1.20 (d, J=7.3 Hz, 3H, ala-CH$_3$), 1.38, 1.41 (2×s, 18H, 2×C(CH$_3$)$_3$), 1.80–2.28 (m, 6H, glu β-CH$_2$, glu γ-CH$_2$ and cyclopenta[g]quinazoline 7-CH$_2$), 2.33 (s, 3H, cyclopenta[g]quinazoline 2-CH$_3$), 2.97, 3.13 (2×m, 3H, cyclopenta[g]quinazoline 8-CH$_2$ and C≡CH), 3.95 (ABq, J=19.3 Hz, 2H, CH$_2$C≡C), 4.09 (m(obscured), 1H, ala α-CH), 4.26 (m, 1H, glu α-CH), 5.75 (t, J=8.1 Hz, 1H, cyclopenta[g]quinazoline 6-CH), 7.01 (d, J=8.9 Hz, 2H, 3',5'-ArH), 7.48 (s, 1H, cyclopenta[g] quinazoline 9-H), 7.79 (d, J=8.4 Hz, 3H, 2',6'-ArH and cyclopenta[g]quinazoline 5-H), 8.21 (d, J=7.0 Hz, 1H, ala NH), 8.35 (d, J=7.3 Hz, 1H, glu NH), 12.10 (s, 1H, cyclopenta[g]quinazoline N3-H).

Mass Spectrum: (FAB) m/e 708 [(M+Na)$^+$].

Elemental Analysis: Found C, 65.76; H, 6.99; N, 9.80; C$_{38}$H$_{47}$N$_5$O$_7$ 0.5 H$_2$O requires C, 65.69; H, 6.96; N, 10.07%.

(2) N-{N-{-p-[N-((6RS)-2-methyl-4-oxo-3,4,7,8-tetrahydro-6H-cyclopenta[g] quinazolin-6-yl)-N-(prop-2-ynyl)amino]benzoyl } -L-γ-glutamyl}-D-alanine A solution of di-tert-butyl N-{N-{p-[N-((6RS)-2-methyl-4-oxo-3,4,7,8-tetrahydro-6 H-cyclopenta[g]quinazolin-6-yl)-N-(prop-2-ynyl)amino] benzoyl}-L-γ-glutamyl}-D-alaninate (0.138 g, 0.2 mmol), in trifluoroacetic acid (7 ml) was stirred at room temperature for 1.25 hours with protection from the light. The trifluoroacetic acid was then removed in vacuo to give a yellowish residue which triturated with ether. The precipitated white solid was collected by filtration, washed with ether, dried in vacuo over phosphorous pentoxide and then suspended in water (6.5 ml). To this suspension 1N aqueous sodium hydroxide (1 ml) was added to give a clear solution which was stirred at room temperature for 10 minutes and then acidified to pH ~4 with 1N hydrochloric acid. The precipitated white solid was collected by filtration, washed with water (~5 ml) and dried in vacuo over phosphorous pentoxide. There was thus obtained N-{N-{p-[N- ((6RS)-2-methyl-4-oxo-3,4,7,8-tetrahydro-6 H-cyclopenta[g]quinazolin-6-yl)-N-(prop-2-ynyl)amino] benzoyl}-L-γ-glutamyl}-D-alanine (0.083 g, 73%) as a white solid, m.p. 185° C. (dec);

NMR Spectrum: (CD$_3$SOCD$_3$) 1.23 (d, J=7.3 Hz, 3H, ala -CH$_3$), 1.83–2.28 (m, 6H, glu β-CH$_2$, glu γ-CH$_2$ and cyclopenta[g]quinazoline 7-CH$_2$), 2.33 (s, 3H, cyclopenta [g]quinazoline 2-CH$_3$), 2.97, 3.15 (2×m, 3H, cyclopenta[g] quinazoline 8-CH$_2$ and C≡CH), 3.96 (ABq, J=19.0 Hz, 2H, CH$_2$C≡C), 4.18 (m(obscured), 1H, ala α-CH), 4.35 (m, 1H, glu α-CH), 5.76 (t, J=8.1 Hz, 1H, cyclopenta[g]quinazoline 6-CH), 7.02 (d, J=8.9 Hz, 2H, 3',5'-ArH), 7.49 (s, 1H, cyclopenta[g]quinazoline 9-H), 7.81 (d, J=8.5 Hz, 3H, 2',6'-ArH and cyclopenta[g]quinazoline 5-H), 8.17 (d, J=7.0 Hz, 1H, ala NH), 8.33 (d, J=7.4 Hz, 1H, glu NH), 12.10 (s, 1H, cyclopenta[g]quinazoline N3-H).

Mass Spectrum: (FAB) m/e 574 [(M+H)$^+$].

Elemental Analysis: Found C, 59.93; H, 5.72; N, 11.68; C$_{30}$H$_{31}$N$_5$O$_7$ 1.5 H$_2$O requires C, 59.99; H, 5.71; N, 11.66%.

Example 20

Formulation

The following illustrate representative pharmaceutical dosage forms containing a cyclopentaquinazoline of formula (I), particularly in pharmaceutically acceptable salt form, for therapeutic or prophylactic use in humans:

|  | mg/tablet |
|---|---|
| (a) Tablet I | |
| Cyclopentaquinazoline salt | 100 |
| Lactose Ph.Eur | 182.75 |
| Croscarmellose sodium | 12.0 |
| Maize starch paste (5% w/v paste) | 2.25 |
| Magnesium stearate | 3.0 |
| (b) Tablet II | |
| Cyclopentaquinazoline salt | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | |
| Cyclopentaquinazoline salt | 1.0 |
| Lactose Ph.Eur | 93.25 |
| Croscarmellose sodium | 4.0 |
| Maize starch paste (5% w/v paste) | 0.75 |
| Magnesium stearate | 1.0 |
| (d) Capsule | mg/capsule |
| Cyclopentaquinazoline salt | 10.0 |
| Lactose Ph.Eur | 488.5 |
| Magnesium stearate | 1.5 |

| | (50 mg/ml) |
|---|---|
| (e) Injection I | |
| Cyclopentaquinazoline salt | 5.0% w/v |
| 1M Sodium hydroxide solution | 15.0% w/v |
| 0.1M Hydrochloric acid (to adjust pH to 7.6) | |
| Polyethylene glycol 400 | 4.5% w/v |
| Water for injection to 100% | |

| | (10 mg/ml) |
|---|---|
| (f) Injection II | |
| Cyclopentaquinazoline salt | 1.0% w/v |
| Sodium phosphate BP | 3.6% w/v |
| 0.1M Sodium hydroxide solution | 15.0% w/v |
| Water for injection to 100% | |

| | (1 mg/ml buffered to pH 6) |
|---|---|
| (g) Injection III | |
| Cyclopentaquinazoline salt | 0.1% w/v |
| Sodium phosphate BP | 2.26% w/v |
| Citric acid | 0.38% w/v |
| Polyethylene glycol 400 | 3.5% w/v |
| Water for injection to 100% | |

The above formulations may be prepared by conventional procedures well known in the pharmaceutical art. The tablets (a) to (c) may be enteric coated by conventional means, for example with a coating of cellulose acetate phthalate.

We claim:

1. A cyclopentaquinazoline of the formula (I):

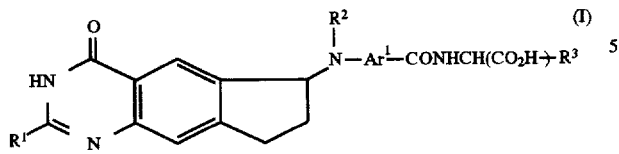

wherein $R^1$ is hydrogen, amino, $C_{1-4}$ alkyl, $C_{1-4}$ alkoxy, $C_{1-4}$ hydroxyalkyl or $C_{1-4}$ fluoroalkyl;

wherein $R^2$ is hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl;

$Ar^1$ is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy; and wherein $R^3$ is a group of the formula:

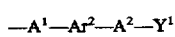

in which $A^1$ is a bond between the α-carbon atom of the group —CONHCH(CO$_2$H)— and $Ar^2$ or is a $C_{1-2}$ alkylene group;

$Ar^2$ is phenylene, tetrazoldiyl, thiophenediyl, thiazolediyl, pyridinediyl or pyrimidinediyl which in the case of phenylene may optionally bear one or two substituents on the ring selected from halogeno, nitro, $C_{1-4}$ alkyl and $C_{1-4}$ alkoxy;

$A^2$ is a $C_{1-3}$ alkylene or $C_{2-3}$ alkenylene group; and $Y^1$ is carboxy, tetrazol-5-yl, N-($C_{1-4}$ alkylsulphonyl)carbamoyl, N-(phenylsulphonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulphinyl or tetrazol-5-ylsulphonyl; or $Y^1$ is a group of the formula:

—CON(R)CH(Y$^2$)Y$^3$ in which R is hydrogen, $C_{1-4}$ alkyl, $C_{3-4}$ alkenyl or $C_{3-4}$ alkynyl;

$Y^2$ is carboxy, tetrazol-5-yl, N-($C_{1-4}$ alkylsulphonyl)carbamoyl, N-(phenylsulphonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulphinyl or tetrazol-5-ylsulphonyl; and $Y^3$ is the residue of a naturally occurring amino acid NH$_2$CH(CO$_2$H)Y$^3$; or $Y^3$ is a group of the formula:

—A$^4$—CO$_2$H in which $A^4$ is a $C_{2-6}$ alkylene group other than ethylene; wherein $R^3$ is a group of the formula:

—A$^5$—CON(R)CH(Y$^4$)Y$^5$ in which $A^5$ is a $C_{1-6}$ alkylene group and R is as defined above;

$Y^4$ is carboxy, tetrazol-5-yl, N-($C_{1-4}$ alkylsulphonyl)carbamoyl, N-(phenylsulphonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulphinyl or tetrazol-5-ylsulphonyl; and $Y^5$ is the residue of a naturally occurring amino acid NH$_2$CH(CO$_2$H)Y$^5$ provided that when R is hydrogen and $Y^4$ is carboxy it is not the residue of glutamic acid; or $Y^5$ is a group of the formula:

—A$^4$—CO$_2$H in which $A^4$ is as defined above; or $Y^5$ is a group of the formula:

—A$^6$—Ar$^3$—A$^7$—Y$^6$ in which $A^6$ is a bond between the α-carbon atom of the group —A$^5$—CON(R)CH(Y$^4$)— and $Ar^3$ or is a $C_{1-2}$ alkylene group;

$Ar^3$ is phenylene, tetrazoldiyl, thiophenediyl, thiazolediyl, pyridinediyl or pyrimidinediyl which in the case of phenylene may optionally bear one or two substituents on the ring selected from halogeno, nitro, $C_{1-4}$ alkyl and $C_{1-4}$ alkoxy;

$A^7$ is a $C_{1-3}$ alkylene or $C_{2-3}$ alkenylene group; and $Y^6$ is carboxy, tetrazol-5-yl, N-($C_{1-4}$ alkylsulphonyl)carbamoyl, N-(phenylsulphonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulphinyl or tetrazol-5-ylsulphonyl; or wherein $R^3$ is a group of the formula:

—A$^8$—X—Ar$^4$ in which $A^8$ is a $C_{1-4}$ alkylene group;

X is sulphinyl, sulphonyl or methylene;

and $Ar^4$ is 1,2,3-triazol-4-yl, 1,2,4-triazol-3-yl or, except when X is methylene, tetrazol-5-yl;

the compound (I) optionally being in the form of a pharmaceutically acceptable salt or ester.

2. A cyclopentaquinazoline according to claim 1, wherein $R^3$ is a group of the formula —A$^1$—Ar$^2$—A$^2$—Y$^1$ in which $A^1$ is a bond or is methylene or ethylene, $Ar^2$ is phenylene, thiophenediyl or tetrazoldiyl, $A^2$ is methylene, ethylene or trimethylene and $Y^1$ is carboxy or tetrazol-5-yl.

3. A cyclopentaquinazoline according to claim 1, wherein $R^3$ is a group of the formula —A$^5$—CON(R)CH(Y$^4$)—A$^6$—Ar$^3$—A$^7$—Y$^6$ in which $A^5$ is methylene or ethylene, R is hydrogen or methyl, $Y^4$ is carboxy or tetrazol-5-yl, $A^6$ is a bond or is methylene or ethylene, $Ar^3$ is phenylene, thiophenediyl or tetrazoldiyl, $A^7$ is methylene, ethylene or trimethylene and $Y^6$ is carboxy or tetrazol-5-yl.

4. A cyclopentaquinazoline according to claim 1, wherein $R^1$ is hydrogen, amino, hydroxymethyl or methyl;

wherein $R^2$ is hydrogen, methyl, ethyl, propyl, prop-2-enyl, prop-2-ynyl, 2-hydroxyethyl, 2-fluoroethyl, 2-bromoethyl or 2-cyanoethyl; and wherein $Ar^1$ is 1,4-phenylene which may optionally bear one or two substituents selected from the group consisting of fluoro and chloro or $Ar^1$ is thiophene-2,5-diyl, thiazole-2,5-diyl or pyridine-2,5-diyl.

5. A cyclopentaquinazoline according to claim 1, wherein $R^1$ is amino, hydroxymethyl or methyl;

wherein $R^2$ is methyl, ethyl or prop-2-ynyl; and wherein Ar¹ is 1,4-phenylene, 2-fluoro-1,4-phenylene, 2,6-difluoro-1,4-phenylene or pyridine-2,5-diyl.

6. A cyclopentaquinazoline according to claim 1,
   wherein R¹ is methyl;
   wherein R² is methyl or prop-2-ynyl;
   wherein Ar¹ is 1,4-phenylene or 2-fluoro-1,4-phenylene; and
   wherein R³ is p-carboxymethylphenyl, 2-(1-carboxymethyltetrazol-5-yl)ethyl, 2-(2-carboxymethyltetrazol-5-yl)ethyl or 2-(N-[p-carboxymethyl-α-carboxybenzyl]-carbamoyl)ethyl.

7. A cyclopentaquinazoline being:
   2-{p-[N-methyl-N-(2-amino-4-oxo-3,4,7,8-tetrahydro-6 H-cyclopenta(g)quinazolin-6-yl)amino]benzamido}-4-(1- or 2-carboxymethyltetrazol-5-yl)butyric acid,
   2-{p-[N-ethyl-N-(2-amnino-4-oxo-3,4,7,8-tetrahydro-6 H-cyclopenta(g)quinazolin-6-yl)-amino]benzamido}-4-(1- or 2-carboxymethyltetrazol-5-yl)butyric acid,
   2-{p-[N-(prop-2-ynyl)-N-(2-amino-4-oxo-3,4,7,8-tetrahydro-6 H-cyclopent(g)-quinazolin-6-yl)amino]benzamido}-4-(1- or 2-carboxymethyltetrazol-5-yl)butyric acid,
   2-{p-[N-methyl-(2-hydroxymethyl-4-oxo-3,4,7,8-tetrahydro-6 H-cyclopent(g)-quinazolin-6-yl)amino]benzamido}-4-(1- or 2-carboxymethyltetrazol-5-yl)butyric acid,
   2-{p-[N-ethyl-N-(2-hydroxymethyl-4-oxo-3,4,7,8-tetrahydro-6 H-cyclopenta(g)-quinazolin-6-yl)amino]benzamido}-4-(1- or 2-carboxymethyltetrazol-5-yl)butyric acid,
   2-{p-[N-prop-2-ynyl)-N-(2-hydroxymethyl-4-oxo-3,4,7,8-tetrahydro-6 H-cyclopenta(g)-quinazolin-6-yl)amino]benzamido}-4-(1- or 2-carboxymethyltetrazol-5-yl)butyric acid,
   2-{p-[N-methyl-N-(2-methyl-4-oxo-3,4,7,8-tetrahydro-6 H-cyclopenta(g)quinazolin-6-yl)amino]benzamido}-4-(1- or 2-carboxymethyltetrazol-5-yl)butyric acid,
   2-{p-[N-ethyl-N-(2-methyl-4-oxo-3,4,7,8-tetrahydro-6 H-cyclopenta(g)quinazolin-6-yl)amino]benzamido}-4-(1- or 2-carboxymethyltetrazol-5-yl)butyric acid,
   2-{p-[N-(prop-2-ynyl)-N-(2-methyl-4-oxo-3,4,7,8-tetrahydro-6 H-cyclopenta(g)-quinazolin-6-yl)amino]benzamido}-4-(1- or 2-carboxymethyltetrazol-5-yl)butyric acid,
   2-{o-fluoro-p-[N-methyl-N-(2-amino-4-oxo-3,4,7,8-tetrahydro-6 H-cyclopenta(g)-quinazolin-6-yl)amino]benzamido}-4-(1- or 2-carboxymethyltetrazol-5-yl)butyric acid,
   2-{o-fluoro-p-[N-ethyl-N-(2-amino-4-oxo-3,4,7,8-tetrahydro-6 H-cyclopenta(g)-quinazolin-6-yl)amino]benzamido}-4-(1- or 2-carboxymethyltetrazol-5-yl)butyric acid,
   2-{o-fluoro-p-[N-(prop-2-ynyl)-N-(2-amino-4-oxo-3,4,7,8-tetrahydro-6 H-cyclopenta(g)quinazolin-6-yl)amino]benzamido}-4-(1- or 2-carboxymethyltetrazol-5-yl)butyric acid,
   2-{o-fluoro-p-[N-methyl-N-(2-hydroxymethyl-4-oxo-3,4,7,8 - t e t r a h y d r o - 6 H-cyclopenta(g)quinazolin-6-yl)amino]benzamido}-4-(1- or 2-carboxymethyltetrazol-5-yl)butyric acid,
   2-{o-fluoro-p-[N-ethyl-N-(2-hydroxymethyl-4-oxo-3,4,7,8-tetrahydro-6 H-cyclopenta(g)quinazolin-6-yl)amino]benzamido}-4-(1- or 2-carboxymethyltetrazol-5-yl)butyric acid,
   2-{o-fluoro-p-[N-(prop-2-ynyl)-N-(2-hydroxymethyl-4-oxo-3,4,7,8-tetrahydro-6 H-cyclopenta(g)quinazolin-6-yl)amino]benzamido}-4-(1- or 2-carboxymethyltetrazol-5-yl)butyric acid,
   2-{o-fluoro-p-[N-methyl-N-(2-methyl-4-oxo-3,4,7,8-tetrahydro-6 H-cyclopenta(g)-quinazolin-6-yl)amino]benzamido}-4-(1- or 2-carboxymethyltetrazol-5-yl)butyric acid,
   2-{o-fluoro-p-[N-ethyl-N-(2-methyl-4-oxo-3,4,7,8-tetrahydro-6 H-cyclopenta(g)-quinazolin-6-yl)amino]benzamido}-4-(1- or 2-carboxymethyltetrazol-5-yl)butyric acid,
   2-{o-fluoro-p-[N-(prop-2ynyl)-N-(2-methyl-4-oxo-3,4,7,8-tetrahydro-6 H-cyclopenta(g)quinazolin-6-yl)amino]benzamido}-4-(1- or 2-carboxymethyltetrazol-5-yl)butyric acid;

or a pharmaceutically acceptable salt or ester thereof.

8. A process for the manufacture of a cyclopentaquinazoline of the formula (I) according to claim 1 which comprises:

(a) the reaction of an acid of the formula (II):

$$R^4\text{-N}\cdots\text{C(O)}\text{-Ar-}\overset{R^2}{\underset{|}{N}}-Ar^1-CO_2H \quad (II)$$

or a reactive derivative thereof with the terminal amino group of a compound of the formula:

$$NH_2CH(CO_2H)\text{---}R^3$$

wherein R¹, R², R³ and Ar¹ have the meanings stated in claim 1 and any amino group in R³ and Ar¹ is protected by a conventional protecting group, any amino group in R¹, any hydroxy group in R¹, R², R³ and Ar¹ and the carboxy group or groups in NH₂CH(CO₂H)—R³ may be protected by a conventional protecting group or alternatively such an amino, hydroxy or carboxy group need not be protected; and wherein R⁴ is hydrogen or a protecting group;

(b) the reaction of a compound of the formula (III):

$$R^4\text{-N}\cdots\text{C(O)}\text{-Ar-}Z \quad (III)$$

or the reductive amination of a compound of the formula (IIIA):

$$R^4\text{-N}\cdots\text{C(O)}\text{-Ar-}=O \quad (IIIA)$$

with a compound of the formula:

$$NH(R^2)\text{---}Ar^1\text{---}CONHCH(CO_2H)\text{---}R^3$$

wherein R¹, R², R³, R⁴ and Ar¹ have the meanings stated under (a) above and any amino group in R³ and Ar¹ is protected by a conventional protecting group, the carboxy group or groups in NH(R²)—Ar¹—CONHCH(CO₂H)—R³ are protected by a conventional protecting group and any amino group in R¹ and any hydroxy group in R¹, R², R³ and Ar¹ may be protected by a conventional protecting group or alternatively such an amino or hydroxy group need not be protected; and wherein Z is a displaceable group;

(c) the alkylation of an amine of the formula (IV):

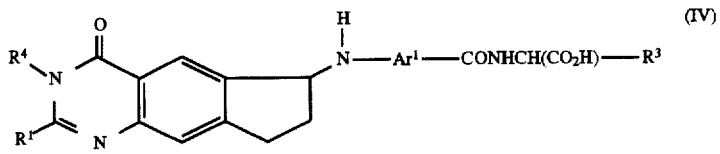

with an alkylating agent of the formula:

wherein $R^1$, $R^2$, $R^3$, $R^4$ and $Ar^1$ have the meanings stated under (a) above and any amino group in $R^1$, $R^3$ and $Ar^1$ is protected by a conventional protecting group; and wherein Z is a displaceable group; or (d) when the cyclopentaquinazoline has a group $R^2$ whose attachment to the nitrogen atom to which it is bonded is through a methylene group, the reductive amination with an amine of the formula (IV) as described under (c) above of a compound of the formula:

wherein $R^8$ is a group such that $R^8$—$CH_2$ corresponds to $R^2$;

and thereafter, where appropriate, in any of (a) to (d), any undesired protecting group, including any protecting group $R^4$, is removed by conventional means and/or in any of (a) to (d) the compound of formula (I) is converted to a pharmaceutcially acceptable salt or ester form thereof.

9. A cyclopentaquinazoline of the formula (IIIA):

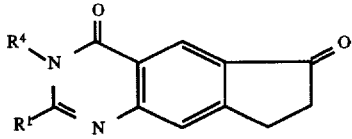

wherein $R^1$ is hydrogen, amino, $C_{1-4}$ alkyl, $C_{1-4}$ alkoxy, $C_{1-4}$ hydroxyalkyl or $C_{1-4}$ fluoroalkyl; and wherein $R^4$ is hydrogen or a protecting group.

10. A cyclopentaquinazoline according to claim 9, wherein $R^1$ is hydrogen, amino, hydroxymethyl or methyl.

11. A cyclopentaquinazoline according to claim 9, wherein $R^4$ is a pivaloyloxymethyl group.

12. A pharmaceutical composition comprising a cyclopentaquinazoline according to claim 1 together with a pharmaceutically acceptable diluent or carrier.

13. A method for aiding regression and palliation of cancer in a patient in need of such treatment which comprises administering to said patient an effective amount of a cyclopentaquinazoline according to any of claim 1.

* * * * *

UNITED STATES PATENT AND TRADEMARK OFFICE
CERTIFICATE OF CORRECTION

PATENT NO. : 5,747,499
DATED : May 5, 1998
INVENTOR(S) : Bavetsias, et. al.

It is certified that error appears in the above-identified patent and that said Letters Patent is hereby corrected as shown below:

Title page, item [73], Assignee: should read --British Technology Group Limited, London, England and Zeneca Limited, London, England--.

Signed and Sealed this

Twelfth Day of January, 1999

Attest:

Attesting Officer

*Acting Commissioner of Patents and Trademarks*